US012661484B2

(12) United States Patent
Patil et al.

(10) Patent No.: US 12,661,484 B2
(45) Date of Patent: Jun. 23, 2026

(54) GUIDEWIRE WITH CONDUCTIVE ELEMENT

(71) Applicants: Asahi Intecc Co., Ltd., Seto (JP);
Pathways Medical Corporation, Santa Clara, CA (US)

(72) Inventors: Nitin Patil, Danville, CA (US); Minoru Ogawa, Seto (JP); Philip R. Houle, Sunnyvale, CA (US)

(73) Assignees: ASAHI INTECC CO., LTD., Seto (JP); PATHWAYS MEDICAL CORPORATION, Santa Clara, CA (US)

( * ) Notice: Subject to any disclaimer, the term of this patent is extended or adjusted under 35 U.S.C. 154(b) by 1234 days.

(21) Appl. No.: 17/457,844

(22) Filed: Dec. 6, 2021

(65) Prior Publication Data

US 2022/0181827 A1     Jun. 9, 2022

Related U.S. Application Data

(60) Provisional application No. 63/122,430, filed on Dec. 7, 2020.

(51) Int. Cl.
   *A61M 25/09*     (2006.01)
   *H01R 107/00*     (2006.01)

(52) U.S. Cl.
   CPC ... *A61M 25/09* (2013.01); *A61M 2025/09075* (2013.01); *A61M 2025/09108* (2013.01); *A61M 2205/0233* (2013.01); *H01R 2107/00* (2013.01)

(58) Field of Classification Search
   CPC .......... A61M 2205/0233; A61M 25/09; A61M 2025/09075; A61M 2025/09108;
   (Continued)

(56)          References Cited

U.S. PATENT DOCUMENTS 5,425,364 A  *  6/1995  Imran ..................... A61N 1/056
                                                      600/374
6,032,061 A  *  2/2000  Koblish ................ A61L 29/085
                                                      607/116
              (Continued)

FOREIGN PATENT DOCUMENTS

JP        2000-508564 A        7/2000
JP        2003-225312 A        8/2003
              (Continued)

*Primary Examiner* — Sean P Dougherty
(74) *Attorney, Agent, or Firm* — Oliff PLC

(57)          ABSTRACT

Multiple approaches to incorporating multiple conductors on a guidewire by building the multiple conductor traces of variable sizes and material compositions on separate insulating layers are described. The approaches described in the invention facilitate ease of assembly of sensors to the guidewire or catheter element. This approach is particularly useful in scenarios where electrical or mechanical properties of the device need to be altered in specific sections to either enhance device performance and reliability (e.g. selective abrasion resistance), or facilitate ease of assembly (e.g. soldering or connection ease), or in some instances achieve desired electrical characteristics (e.g. impedance). The desired properties are incorporated into the same device requiring an innovative approach to forming signal wires in an otherwise tight space without impacting the primary mechanical performance of the devices.

19 Claims, 46 Drawing Sheets

(58) Field of Classification Search
CPC .......... A61M 2025/0002; A61M 2025/09183; H01R 2107/00; A61B 5/287; A61B 5/027; A61B 5/6851
See application file for complete search history.

(56) References Cited

U.S. PATENT DOCUMENTS

| | | | | |
|---|---|---|---|---|
| 6,106,486 | A * | 8/2000 | Tenerz | .................. A61M 25/09 604/529 |
| 6,445,069 | B1 * | 9/2002 | Ling | ...................... H01L 24/13 257/E21.174 |
| 8,491,484 | B2 * | 7/2013 | Lewis | ................. A61B 5/6851 600/467 |
| 9,734,938 | B2 * | 8/2017 | Kassab | ............... A61B 5/0538 |
| 2006/0074318 | A1 * | 4/2006 | Ahmed | .................... A61B 8/12 600/561 |
| 2010/0280330 | A1 * | 11/2010 | Samuelsson | ........... A61B 5/062 600/300 |
| 2012/0143298 | A1 * | 6/2012 | Just | ................... A61B 18/1492 607/122 |
| 2013/0096455 | A1 * | 4/2013 | Kassab | .................. H01B 7/048 174/113 C |
| 2013/0116528 | A1 * | 5/2013 | Boye | ...................... A61B 5/026 600/373 |
| 2016/0309586 | A1 * | 10/2016 | Patil | .................... H05K 3/4644 |
| 2018/0093078 | A1 * | 4/2018 | Patil | .................... A61B 5/1076 |
| 2020/0060577 | A1 * | 2/2020 | Kassab | ............. A61B 5/02055 |
| 2020/0324081 | A1 * | 10/2020 | Seretse | ................. H05K 1/181 |
| 2022/0111182 | A1 * | 4/2022 | Patil | ............... A61M 25/09041 |

FOREIGN PATENT DOCUMENTS

| | | | | |
|---|---|---|---|---|
| JP | 2006-501866 A | | 1/2006 | |
| JP | 2019-527104 A | | 9/2019 | |
| TW | 201417641 A | | 5/2014 | |
| WO | WO-0136034 A2 * | | 5/2001 | ............ A61M 25/09 |
| WO | WO-2014106158 A1 * | | 7/2014 | ........... A61B 5/0215 |
| WO | WO-2015113044 A1 * | | 7/2015 | ........... A61B 5/6851 |
| WO | WO-2018017731 A1 * | | 1/2018 | ........... A61M 25/09 |

* cited by examiner

GUIDEWIRE WITH CONDUCTIVE ELEMENT

CROSS-REFERENCE OF RELATED APPLICATIONS

This application submits a claim to United States Patent and Trademark Office for a history of a priority to No. 63/122,430 filed on Dec. 7, 2020. The entirety of the application is incorporated herein by reference.

TECHNICAL FIELD

The present invention relates to guidewires having sensors, and methods and apparatus for assembly of guidewires having multiple sensors incorporated within or along the body of the guidewire. In particular, the present invention relates to guidewires incorporating a pressure sensor within or along the body of the guidewire, and relates to methods and apparatus for assembly of the guidewires.

BACKGROUND ART

Guidewires may have a number of sensors or sensor assemblies integrated directly into the guidewire. Such sensor-equipped guidewires may be adapted for measuring various physiological parameters within a patient's body. For instance, sensors typically have one or more cables passed through the guidewire for electrically coupling a sensor element to an electronic assembly.

Guidewires are generally comprised of a hypotube and coiled segment about a core wire which may extend through a length or a partial length of the guidewire. The guidewire core may be fabricated from stainless steel or Nitinol with the coiled segment fabricated from a wire or braid which provide for flexibility, pushability, and kink resistance to the guidewire. Nitinol wire, used by itself or braided with stainless steel, may further help to increase flexibility and allow the wire to spring back into shape.

Moreover, guidewires have a standard diameter of 0.014 in. and consequently accommodating certain types of sensors or having multiple sensors may be limited by a relatively small space provided by the guidewire. Moreover, guidewires are typically used for insertion into and advancement through the vasculature which can present an extremely tortuous pathway. Thus, the guidewire and any sensors or electrodes along the guidewire may experience relatively large stresses as the guidewire is pushed, pulled, or torqued over a passageway having numerous curves and bends.

Guidewires incorporating one or more electrodes along their length may present additional challenges to guidewire construction and use. For instance, the presence of a plurality of electrodes along the guidewire may require additional conductive wiring passed through the length of the guidewire. Because of the limited space and flexibility required from guidewires, any sensors and/or electrodes positioned along their length are desirably correspondingly constructed.

Consequently, there is a need for guidewire designs which provide for effective construction of a guidewire incorporating one or more electrodes and/or sensors along the length.

SUMMARY OF INVENTION

The present disclosure provides a guidewire including: a guidewire core; a first insulating layer disposed on a surface of the guidewire core; multiple first conductive traces arranged spaced apart from each other in a side direction of the guidewire core and disposed on a surface of the first insulating layer and along a length direction of the guidewire core; and multiple connection sections disposed on at least one of both end sides in a length direction of the multiple first conductive traces and electrically connected with an electronic component, wherein ends of the multiple first conductive traces having the multiple connection sections are arranged in parallel to the length direction of the guidewire core, and the multiple connection sections are arranged in a straight line parallel to a longitudinal axis of the guidewire core.

Furthermore, there is provided a second insulating layer that covers the multiple first conductive traces and the first insulating layer, wherein the multiple connection sections may be each configured to include an inner opening that is opened on the second insulating layer so as to reach a corresponding first conductive trace.

The end of at least one conductive trace may be formed extending in a circumferential direction of the guidewire core so as to be located ahead of the end of the other adjacent conductive trace in the length direction of the guidewire core via a gap.

A conductive band made of a conductive material is arranged so as to cover at least a portion of the inner opening of the connection section, a conductive connection member is disposed on the inner opening, the connection section is electrically connected with the conductive band via the conductive connection member, and the conductive band and the conductive connection member may be made of different conductive materials.

The multiple conductive bands each have an outer opening penetrating the conductive band in a thickness direction and arranged so as to overlap with the inner opening, and the conductive connection member for electrically connecting the conductive band with the connection section may be disposed inside the outer opening.

The outer opening and the inner opening may be arranged so as to overlap with each other while being offset from each other in the length direction of the guidewire core.

An area of the inner opening may be larger than an area of the outer opening.

The outer opening may be formed into a rectangular shape in plan view.

The outer opening may be formed into, in plan view, a notched shape, where at least one of the both ends in the width direction of the conductive band is opened.

The outer opening may be formed into, in plan view, an inverse tapered shape that gradually widens from a position opened on one of both ends in a width direction of the conductive band toward a side located at a position deviating in the width direction of the conductive band.

The multiple connection sections may be each disposed on a proximal end side of both end sides in a length direction of each of the multiple first conductive traces.

Each outer opening may be formed on the both end sides in the width direction of the conductive band.

The conductive band and the conductive connection member may be made of conductive materials.

The conductive connection member may be made of an anisotropic conductive material that forms a conductive path in the thickness direction of the conductive band by a pressure applied in the thickness direction of the conductive band and that is more elastically deformable than solders.

The conductive band may include the conductive connection member that is made of the anisotropic conductive material and arranged so as to fill insides of the outer opening and the inner opening and cover the second insulating layer, and a C-shaped member that is made of a conductive material and disposed outside the conductive connection member.

The conductive band made of the conductive material is arranged so as to cover at least a portion of the inner opening of the connection section, the connection section is electrically connected with the conductive band via the conductive connection member disposed inside the inner opening, and the conductive band and the conductive connection member may be integrally formed.

A conductive wire wound around an outer circumferential surface of the second insulating layer is provided, and both ends of the conductive wire may be fixed to the first conductive trace via the inner opening.

In the first conductive trace, a region to which one end of the conductive wire is fixed has a metal layer of gold or a gold alloy and a barrier metal layer preventing diffusion between the metal layer and conductive traces, and the conductive wire may be made of gold, a gold alloy, or aluminum.

The multiple connection sections may be disposed on the distal end side of the both end sides in the length direction of the multiple first conductive traces.

Furthermore, the guidewire includes: multiple second conductive traces disposed on the surface of the second insulating layer; a third insulating layer arranged so as to cover the multiple second conductive traces and the second insulating layer; the multiple second connection sections arranged in a straight line parallel to a longitudinal axis of the guidewire core on at least one of both end sides in a length direction of the multiple second conductive traces and electrically connected with the electronic component, and configured to include a second inner opening opened on the third insulating layer so as to reach a corresponding second conductive trace; and a second conductive band formed in the circumferential direction of the guidewire core so as to cover at least one of the multiple second connection sections, wherein the second connection section covered by the second conductive band may be electrically connected with the second conductive band via the conductive connection member disposed on the second inner opening.

The multiple connection sections are disposed on the distal end side of the both end sides in the length direction of the multiple first conductive traces, the conductive band made of the conductive material is arranged so as to cover at least a portion of the inner opening, the connection section is electrically connected with the conductive band via the conductive connection member disposed in the inner opening, and the conductive band may be electrically connected with a printed wiring board equipped with the electronic component via a conductive connection member for a substrate.

The printed wiring board has a flexible substrate member located on the conductive band side and a rigid substrate member located on a distal end side of the flexible substrate member, and the electronic component may be disposed on the rigid substrate member.

The rigid substrate member has an accommodation section for accommodating and mounting the electronic component, and the rigid substrate member may be disposed on the distal end side of the guidewire core.

The multiple first conductive traces may include at least one group consisting of the multiple first conductive traces whose lengths are equal.

The multiple first conductive traces constituting the group may be formed as a point-symmetrical pair.

At least one of the multiple first conductive traces constituting the group may have a meandering section so as to have the same length as of the other first conductive trace in the group.

In an aspect according to the present disclosure, there is provided a guidewire including: a guidewire core; a first insulating layer disposed on a surface of the guidewire core; multiple first conductive traces arranged spaced apart from each other in a side direction of the guidewire core and disposed on a surface of the first insulating layer and along a length direction of the guidewire core; a second insulating layer that covers the multiple first conductive traces and the first insulating layer; multiple connection sections disposed on at least one of both end sides in a length direction of the multiple first conductive traces and electrically connected with an electronic component, and including an inner opening that is opened on the second insulating layer so as to reach a corresponding first conductive trace; conductive bands formed in a circumferential direction so as to cover the multiple connection sections and the second insulating layer; an outer opening penetrating the multiple conductive bands in a thickness direction and arranged so as to overlap with the inner opening; and a conductive connection member disposed inside the outer opening and the inner opening to electrically connect the conductive bands with the connection sections.

The outer opening and the inner opening may be arranged so as to overlap with each other while being offset from each other in the length direction of the guidewire core.

An area of the inner opening may be larger than an area of the outer opening.

The outer opening may be formed into a rectangular shape in plan view.

The outer opening may be formed into, in plan view, a notched shape, where an end side of the conductive band is opened.

The outer opening may be formed into, in plan view, an inverse tapered shape that gradually widens from a position opened on one of both ends in a width direction of the conductive band toward a side located at a position deviating in the width direction of the conductive band.

Each outer opening may be formed on the both end sides in the width direction of the conductive band.

The conductive band and the conductive connection member may be made of conductive materials.

The conductive connection member may be made of an anisotropic conductive material that forms a conductive path in the thickness direction of the conductive band by a pressure applied in the thickness direction of the conductive band.

Furthermore, the guidewire includes: multiple second conductive traces disposed on the surface of the second insulating layer; a third insulating layer arranged so as to cover the multiple second conductive traces and the second insulating layer; multiple second connection sections arranged in a straight line parallel to a longitudinal axis of the guidewire core on at least one of both end sides in a length direction of the multiple second conductive traces and electrically connected with an electronic component, and configured to include a second inner opening opened on the third insulating layer so as to reach a corresponding second conductive trace; and a second conductive band formed in the circumferential direction of the guidewire core so as to cover at least one of the multiple second connection sections, wherein the second connection section covered by the second conductive band may be electrically connected with the second conductive band via the conductive connection member disposed on the second inner opening.

The multiple first conductive traces include at least one group consisting of the multiple first conductive traces whose lengths are equal.

The multiple first conductive traces constituting the group may be formed as a point-symmetrical pair.

At least one of the multiple first conductive traces constituting the group may have a meandering section so as to have the same length as of the other first conductive trace in the group.

In yet another aspect according to the present invention, there is provided a guidewire including: a guidewire core; a first insulating layer disposed on a surface of the guidewire core; multiple first conductive traces arranged spaced apart from each other in a side direction of the guidewire core and disposed on a surface of the first insulating layer and along a length direction of the guidewire core; a second insulating layer that covers the multiple first conductive traces and the first insulating layer; multiple connection sections disposed on at least one of both end sides in a length direction of the multiple first conductive traces, and including an inner opening that is opened on the second insulating layer so as to reach the multiple first conductive traces; and a conductive member that is formed so as to cover the first conductive traces and the second insulating layer via at least one of the multiple connection sections, in which a conductive path is formed in a thickness direction by a pressure applied in the thickness direction.

Furthermore, an electronic component electrically connected with the multiple connection sections is provided, and an electrical connection component as the electronic component has multiple pressing sections corresponding to the multiple first conductive traces, and the electrical connection component may be electrically connected with the multiple first conductive traces by pushing each pressing section against the conductive member.

The conductive member may be made of an anisotropic conductive material that is more elastically deformable than solders.

A conductive band that covers a surface of the conductive member may be provided.

The present disclosure can also be applied to a long medical equipment including the guidewire configured as described above.

In another aspect according to the present disclosure, there is provided a guidewire manufacturing method including: providing a guidewire core; forming a first insulating layer on a surface of the guidewire core; forming multiple first conductive traces arranged along a length direction of the guidewire core on a surface of the first insulating layer; forming multiple connection sections so as to be arranged in a straight line parallel to a longitudinal axis of the guidewire core on at least one of both end sides in a length direction of the multiple first conductive traces; placing an electronic component on a distal side of the guidewire core; and electrically connecting the first conductive traces with the electronic component via inner openings of the connection sections.

In another aspect according to the present disclosure, there is provided a guidewire manufacturing method including: providing a guidewire core; forming a first insulating layer on a surface of the guidewire core; forming multiple first conductive traces arranged along a length direction of the guidewire core on a surface of the first insulating layer; forming a second insulating layer that covers the multiple first conductive traces and the first insulating layer; forming multiple connection sections including an inner opening opened on the second insulating layer so as to reach each of the multiple first conductive traces, on at least one of both end sides in a length direction of the multiple first conductive traces; disposing a conductive band, having an outer opening, on a surface of the second insulating layer such that the outer opening and the inner opening overlap with each other; forming a conductive connection member for electrically connecting the conductive band with a connection section corresponding to the conductive band, inside the outer opening and the inner opening; disposing an electronic component on a distal end side of the guidewire core; and electrically connecting the electronic component with the conductive band.

In yet another aspect according to the present disclosure, there is provided a guidewire manufacturing method including: providing a guidewire core; forming a first insulating layer on a surface of the guidewire core; forming multiple first conductive traces arranged along a length direction of the guidewire core on a surface of the first insulating layer; forming a second insulating layer that covers the multiple first conductive traces and the first insulating layer; forming multiple connection sections including an inner opening opened on the second insulating layer so as to reach each of the multiple first conductive traces, on at least one of both end sides in a length direction of the multiple first conductive traces; forming a conductive member that is arranged so as to cover the first conductive traces located inside the inner opening of the connection section and the second insulating layer, in which a conductive path is formed in a thickness direction by a pressure applied in the thickness direction; disposing an electronic component on a distal end side of the guidewire core; and electrically connecting the electronic component with the conductive member.

Guidewires may incorporate a number of different sensors within or along a body of the guidewire. One particular variation may incorporate a pressure sensor optionally with one or more electrodes along the body of a guidewire or at the distal end of the guidewire. A guidewire having one or more electrodes integrated directly along the guidewire body may have a proximal coil attached to an electrode assembly having one or more electrodes and a distal coil attached to a distal end of the electrode assembly. A guidewire core may extend through a length of a guidewire assembly and may extend partially or entirely through the electrode assembly.

One variation for assembling the guidewire assembly may generally include providing a core wire having a tapered distal section, securing a sensor package having one or more conductive wires to the core wire by passing the core wire through a wire receiving channel defined through or along a sensor package, securing the one or more conductive wires to the core wire, and then encasing the one or more conductive wires and the core wire.

One example of a method of forming the guidewire assembly may generally include providing a guidewire core, disposing an insulating layer upon a surface of the guidewire core, and printing one or more conductive traces directly upon a surface of the insulating layer.

Another example of the method of forming the guidewire assembly may generally include providing the guidewire core, disposing the insulating layer upon the surface of the guidewire core, and disposing an aerosolized conductive ink upon a surface of the insulating layer to form one or more conductive traces.

Yet another example of the method of forming the guidewire assembly may generally include providing a guidewire core, disposing an insulating layer upon a surface of the guidewire core, disposing a conductive layer upon a surface of the insulating layer, and removing portions of the conductive layer such that one or more conductive traces are formed upon the insulating layer.

In forming the guidewire assembly, the pressure sensor packaging, in one variation, may generally comprise a sensor casing which may form a cylindrically shaped housing which encloses or supports the components of the pressure sensor secured within. The sensor casing may define a sensing window along a side surface of the casing, which exposes the pressure sensor within to a fluid environment. A sensor core may be secured within the sensor casing, which connects to a flex circuit which may extend from a proximal end of the sensor casing for connection to a controller or processor via one or more conductors extending through the guidewire length. The conductive traces or wires along the flex circuit may be attached directly to one or more corresponding conductive wires which may extend proximally through the guidewire body for electrical connection to a controller or processor.

Another variation includes a configuration where the flex circuit extends proximally from the sensor casing but instead of being directly attached to the one or more conductive wires, the flex circuit may be electrically connected to one or more conductive ring elements which in turn are electrically connected to the one or more conductive wires. The ring elements may be aligned coaxially and adjacent to one another, and the number of the elements used may depend upon the number of electrical connections desired. The one or more conductive wires may be selectively coupled electrically to a particular pad or trace on the flex circuit so that each ring element is electrically connected to a single pad or trace. Each ring element may then be electrically coupled to a selective conductive wire along an inner diameter of the ring element leaving the remainder of the ring element available for electrical connection to another conductor or component, if so desired.

The sensor casing may define a longitudinal passageway through the entire casing to allow for passage of a guidewire core therethrough. The casing may further define a distal opening into which a distal end of the guidewire may be positioned and secured to extend from the distal end of the casing with the guidewire core extending longitudinally through the casing adjacent or beneath the flex circuit, pressure sensor, and sensing window. The sensor core is shown secured within the casing adjacent to the flex circuit which extends proximally from the casing.

In yet another variation for electrically coupling elements within or along a guidewire, a guidewire assembly may have a conductive ink printed upon a polymer substrate to form a subassembly for carrying signals from one end to the other end of the guidewire or catheter. Using conductive traces directly upon a device substrate and then insulating the traces by a dielectric material eliminates the need to have conductive wires and associated processing and handling of the same.

A polymer layer (e.g., PET, PTFE, etc.) may be coated over the guidewire core via heat shrink to provide an insulating substrate. The polymer layer may be coated or laid upon the entirety of the guidewire core or a portion of the distal end may remain uncoated for securement of a pressure sensor assembly. The one or more conductive traces (e.g., nano silver, nano gold, nano copper, etc.) may then be printed directly upon the polymer layer such that the traces extend from one or more corresponding distal pads to one or more corresponding proximal pads.

Because these one or more conductive traces are printed directly upon the polymer layer, they may be configured in a number of different patterns. Once the one or more conductive traces have been printed upon the polymer layer, the traces may then be insulated. One variation for insulating the traces may involve masking the ends of the traces that will need to remain exposed to form pads for electrical connections and then depositing another layer of polymer upon the conductive traces. For instance, another heat shrink tubing or layer may be used or another layer of polymer (such as PTFE, parylene, etc.) may be deposited upon the exposed conductive traces using, e.g., physical vapor deposition, dip coating, etc.

In yet another variation, a conductive coating can be applied over a dielectric coating either by a bulk metallization process such as physical vapor deposition (PVD), or by electro plating, electroless plating, printing a wider metal layer using a conductive ink on top of the dielectric layer, etc. Such a metal layer can provide EM shielding and thus eliminate or reduce noise and increase system signal to noise ratio (SNR).

Another variation for insulating the traces may involve printing a dielectric polymer directly upon the conductive traces using polymer inks. In the case of using the polymer inks to directly print upon the conductive traces, the printing process may be used to selectively print the polymer inks to create the insulating layer while exposing portions of the conductive traces to form conductive pads for electrical coupling to components.

Regardless of which method is used, the resulting guidewire core and polymer layer may be coupled with the pressure sensor assembly. The one or more ring elements may be electrically coupled along portions of their inner diameter to a corresponding pad exposed along the flex circuit and a second portion along the one or more ring elements may be electrically coupled to a corresponding pad of the conductive traces disposed upon the polymer layer to electrically couple the pressure sensor assembly (or any other component). A distal coil tip may then be attached to the distal end of the sensor casing and the polymers may be reflowed or molded over the guidewire core along the central section, the distal coil or tip along the distal section, and the remainder of the guidewire core along the proximal section as well as the portions between the electrodes (if utilized).

Another variation of the assembly method includes a polymer layer formed separately prior to being disposed upon the guidewire core. The conductive traces may be printed directly upon an outer layer of the polymer along with their corresponding exposed pads extending over the length of the polymer layer. The insulating layer may be likewise printed directly upon the conductive traces. With a pre-printed polymer layer, the guidewire core may be inserted into the polymer layer and bonded with any number of suitable adhesives, e.g., cyanoacrylate, etc. The pressure sensor assembly may then be secured to the guidewire core and the flex circuit may be electrically coupled directly to the exposed pads at attachments to complete the electrical connection. In yet another variation for printing the conductive traces, a polymer tube may be disposed upon the guidewire core and the one or more conductive traces may be printed upon an outer layer of the tube. The conductive ink may then be used to print circular rings upon the polymer tube such that the rings coincide with exposed regions of the conductive traces so that the pressure sensor assembly flex circuit, or any other component, may be electrically coupled to the conductive traces via connection to the circular rings.

Because the circular rings are printed circumferentially around the tube, the exposed regions may be offset longitudinally from one another to allow for the rings to be printed around the entire tube circumference. Also, there is preferably adequate longitudinal spacing between the exposed regions to allow for the rings to be printed coaxially relative to one another without interference. In other variations, partial circumferential rings may be printed than full circumferential rings.

Yet another variation for creating the conductive traces may have a first insulating polymer layer (e.g., PARYLENE (Specialty Coating Systems, Inc., Indianapolis, Ind.), TEF-LON (E. I. Du Pont De Nemours, Wilmington, Del.), polyimide, etc.) disposed upon an outer surface of the guidewire core. A second conductive polymer layer (gold, silver, copper, etc.) having a conductive material may then be coated upon the first polymer layer using any number of processes such as, e.g., electroless deposition, physical vapor deposition, etc. The thickness of the conductive layer is dependent on the application and is often determined considering both electrical requirements (current carrying capacity) and mechanical requirements of the device (e.g. stiffness). This second conductive layer may be separated into discrete conductive elements using, e.g., laser micro machining, photochemical etching, etc.

The entire assembly can then be insulated using a dielectric insulating polymer either in the form of a coating or heat shrink (e.g. Teflon, PET, etc.) depending on the application. Depending on the application several discrete conductive elements can be formed. Also depending on the application various connecting terminal sizes and shapes can be formed at either ends to facilitate connecting to the discrete conductive elements so formed. Such a construction technique helps achieve several discrete conductive elements directly on the device thereby eliminating the need to remove materials to accommodate separate conducing wires or make the device hollow to accommodate conductive wires or elements. Therefore, the intended device performance is greatly enhanced and manufacturing costs are reduced.

DESCRIPTION OF EMBODIMENTS

In the present disclosure, conductive traces are formed on a guidewire core, and multiple electrical connection sections are individually provided on both end sides in a length direction of the conductive traces. The multiple electrical connection sections are arranged in a straight line in a longitudinal axis of the guidewire core. The case where the multiple electrical connection sections are arranged in a straight line includes not only a case where the multiple electrical connection sections are aligned exactly in one straight line, but also a case where the multiple electrical connection sections are arranged along substantially the same straight line. The case where the multiple electrical connection sections are arranged along substantially the same straight line includes e.g. a case where the multiple electrical connection sections are arranged along one direction within a predetermined rectangular range.

In the present disclosure, the multiple conductive traces are electrically connected with at least one sensor disposed on a guidewire via the multiple electrical connection sections. For example, the sensor measures parameters such as a pressure, a temperature, and a flow rate in a body tissue into which the guidewire is inserted. The sensor physically or chemically measures these parameters or other parameters. Signals measured by the sensor are output to a measurement device placed outside the guidewire, via the conductive traces.

In the present disclosure, a guidewire will be explained as an example of a long medical equipment. However, the present disclosure can be applied not only to the guidewire but also to a catheter. For example, the present disclosure can also be applied to a balloon catheter, a microcatheter, a cardiac catheter, a pulmonary artery catheter, an angiographic catheter, a urethral catheter, a gastrointestinal catheter, or the like.

Note that, the present disclosure includes not only the embodiments described below but also variations. A portion of a configurations described in one embodiment will be able to be replaced with a configuration described in another embodiment. A configurations of one embodiment will be able to include a configuration of another embodiment.

Figure 1:
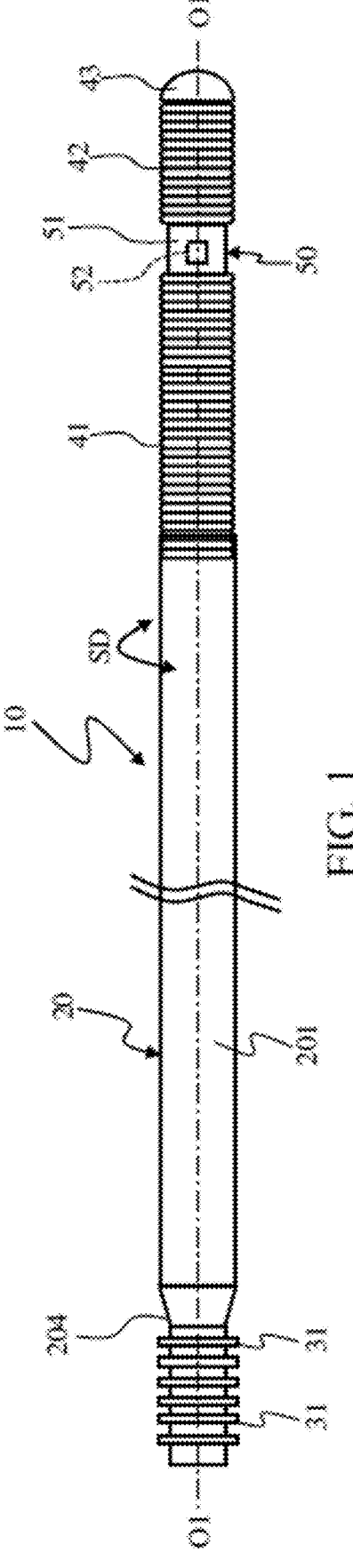
FIG. 1 is a front view of a guidewire having a sensor.
Figure 2:
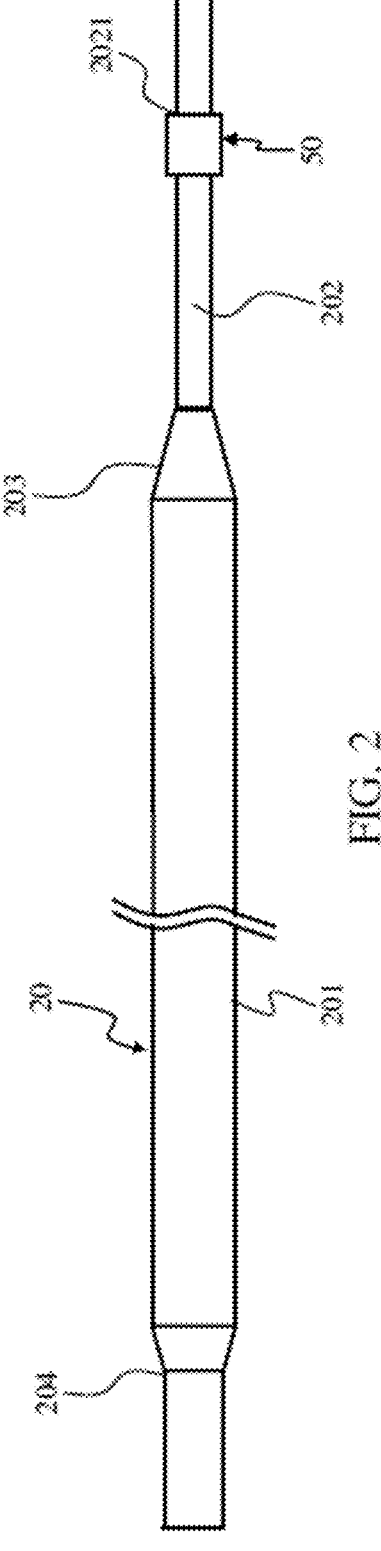
FIG. 2 is a front view of a guidewire core to which the sensor is attached.

FIG. 1 illustrates a whole of a guidewire 10 in which a sensor 52 is attached to a conductive trace. FIG. 2 is a front view of a guidewire core 20 to which the sensor 52 is attached. The guidewire 10 includes e.g. the guidewire core 20 and a sensor assembly 50 disposed on a distal end side of the guidewire core 20. In the present disclosure, a proximal end side of the guidewire 10 is referred to as a proximal end side or a butt side, and a distal end side of the guidewire 10 is referred to as a distal end side in some cases. The guidewire core 20 is formed by assembling coil bodies 41 and 42 and respective ring electrodes 31 onto the guidewire core 20 illustrated in FIG. 2. The coil bodies 41 and 42 are fixed to a small-diameter section 202 of the guidewire core 20 using a fixing material. A distal end tip 43 located on the distal end of the guidewire core 20 is formed in an almost hemispherical shape by a fixation member that fixes a distal end of the small-diameter section 202 of the guidewire core 20 with a distal end of a coil body 42. For example, a brazing material or an adhesive can be used for the fixing material.

The guidewire core 20 is made of e.g. Nitinol or stainless steel. The guidewire core 20 includes a large-diameter section 201 on the butt side, the small-diameter section 202 located on the distal end side of the large-diameter section 201, and a tapered section 203 located between the large-diameter section 201 and the small-diameter section 202. A sensor attachment section 2021 is formed on the distal end side of the small-diameter section 202 as illustrated in FIG. 2. An external connection section 204 is formed on the proximal end side of the large-diameter section 201. The multiple ring electrodes 31 as an example of conductive bands 30 are disposed on the external connection section 204. The conductive bands 30 will be described below. The ring electrodes 31 are components for electrically connecting the guidewire 10 to an external circuit not illustrated in the figure.

The tapered section 203 is formed so as to gradually decrease in diameter such that smooth connection from the distal end side of the large-diameter section 201 to the proximal end side of the small-diameter section 202 is achieved. The multiple coil bodies 41 and 42 are disposed outside the small-diameter section 202. The sensor assembly 50 is disposed between the coil body 41 on the proximal end side and the coil body 42 on the distal end side. The coil bodies 41 and 42 are made of e.g. stainless steel, platinum (Pt), a platinum-iridium alloy (Pt/Ir), or the like. As described below, the guidewire core 20 may have one coil body. Another example of arrangement for the sensor assembly 50 will be described below.

As described below, multiple conductive traces 22 are formed spaced apart from each other in the side direction (SD direction in FIG. 1) on the outside of the guidewire core 20 from the sensor attachment section 2021 to the external connection section 204. The multiple conductive traces 22 have multiple electrical connection sections 24 described below in FIG. 3 on both the sensor attachment section 2021 and the external connection section 204. The side direction of the guidewire core 20 refers to e.g. a circumferential direction of the guidewire core 20, as indicated as an SD direction in FIG. 1. The cross section of the guidewire core 20 is not only a circular shape but also an oval or polygonal shape. In order to make it clear that the cross-sectional shape of the guidewire core 20 is not limited to a circular shape, the lateral direction of the guidewire core 20 is referred to as a side direction.

The "length direction of the guidewire core 20" means e.g. a direction of a central axis O1-O1 of the guidewire core 20 illustrated in FIG. 1. A central axis of the guidewire 10 substantially coincide with the central axis of the guidewire core 20. Thus, the length direction of the guidewire core 20 is substantially identical with a length direction of the guidewire 10. The longitudinal sectional view refers to a sectional view taken along the length direction of the guidewire 10.

Figure 3:
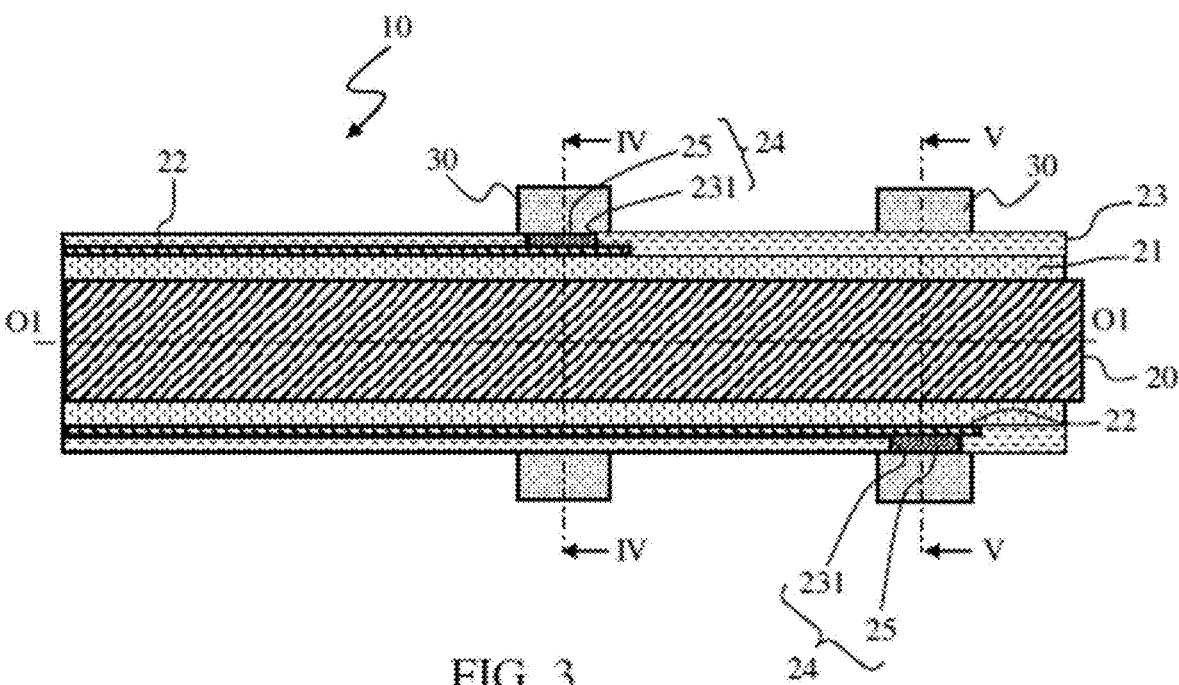
FIG. 3 is a longitudinal sectional view illustrating a state that conductive traces and conductive bands are electrically connected.

FIG. 3 is a longitudinal sectional view illustrating a state that conductive traces and conductive bands are electrically connected. The structure of FIG. 3 can be applied to either the distal end side or the proximal end side of the guidewire 10. The structure illustrated in FIG. 3 may be provided on both the distal end side and the proximal end side of the guidewire 10.

Figure 6:
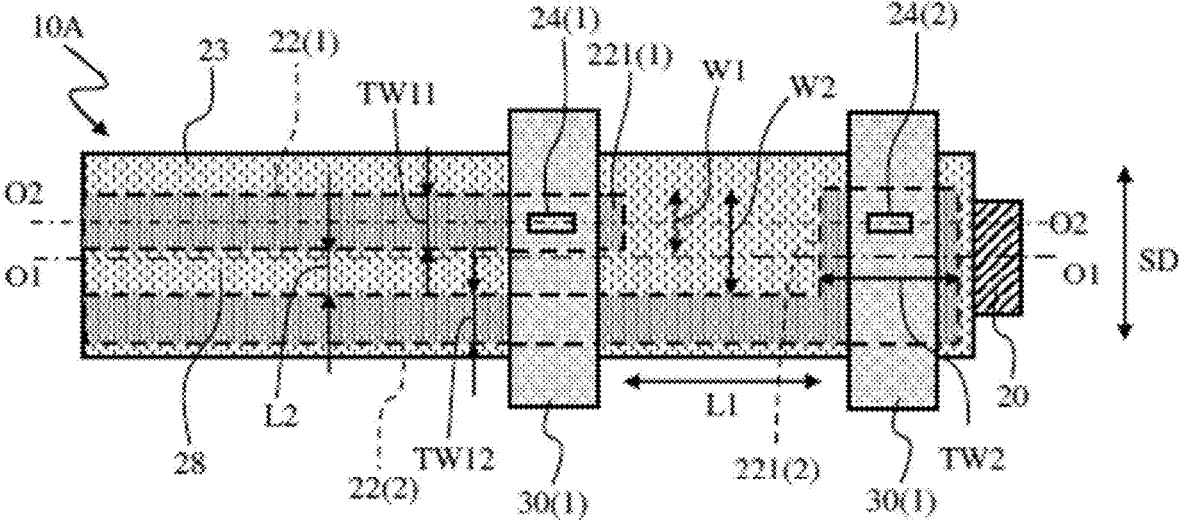
FIG. 6 is a diagram illustrating an arrangement of multiple electrical connection sections aligned in a straight line.

A first insulating layer 21 is disposed on a surface of the guidewire core 20. On the surface of the first insulating layer 21, the multiple conductive traces 22 are formed spaced apart from each other in the side direction of the guidewire core 20. Gaps 28 described below in FIG. 6 are formed between the conductive traces 22 adjacent to each other. To form the gaps 28, e.g. a conductive layer formed on the surface of the first insulating layer 21 is etched into a predetermined shape by a laser beam or the like. The gaps 28 having a desired width dimension can be formed by controlling an output and/or scanning trajectory, or the like of the laser beam. Ordinarily, the gaps 28 are filled with an insulating material. The gaps 28 can also be referred to as insulating space segments.

The multiple electrical connection sections 24 are disposed on either or both the distal end or/and proximal end of each conductive trace 22. The electrical connection section 24 on the distal end side of each conductive trace 22 is to be electrically connected with the sensor 52 via a printed wiring board 60. The electrical connection section 24 on the proximal end side of each conductive trace 22 is to be electrically connected with an external apparatus (not illustrated) such as a measuring device. Each electrical connection section 24 is composed of an inner opening 231 and a conductive connection member 25. The inner opening 231 is formed on a second insulating layer 23 so as to reach the conductive trace 22. The conductive connection member 25 electrically connects the conductive band 30 arranged so as to cover at least a portion of the inner opening 231 with the conductive trace 22. The conductive connection member 25 is disposed in the inner opening 231. In the following example, the conductive connection member 25 is disposed on the inner opening 231 and an outer opening 301 described in FIG. 10.

As described below in FIG. 26, when a second conductive trace 26 is disposed outside the conductive trace 22 with the second insulating layer 23 sandwiched therebetween, a predetermined portion of a third insulating layer 27 that covers the second conductive trace 26 is opened to form the electrical connection section 24. In this case, second inner openings 271 are formed at predetermined positions of the third insulating layer 27, as described later in FIG. 21. Of electrical connection sections 24M, an electrical connection section 24M to be connected to the first conductive trace 22 is electrically connected to the first conductive trace 22 via the conductive connection member 25 disposed on both the first inner opening 231 and the second inner opening 271. The electrical connection sections can be rephrased as openings, i.e. via holes, which are formed at predetermined positions on the insulating layer for the purpose of the electrical connection.

The conductive band 30 is formed from a conductive material in a cylindrical shape, an annular shape, or a C-shape. Each of the conductive bands 30 may be formed in the same shape, or a width dimension of at least one of the conductive bands 30 may be different from width dimensions of the other conductive bands. A thickness dimension of at least one of the conductive bands 30 may be different from thickness dimensions of the other conductive bands 30.

The conductive bands 30 are disposed on the surface of the second insulating layer 23 in correspondence with the respective electrical connection sections 24. Each conductive band 30 is arranged so as to cover at least a portion of the inner opening 231 of each corresponding electrical connection section 24. Each conductive band 30 is electrically connected with each corresponding electrical connection section 24 via the conductive connection member 25.

FIG. 3 illustrates an example in which a predetermined region of the inner circumferential face of the conductive band 30 is electrically connected with the electrical connection section 24 via the conductive connection member 25. That means, the conductive band 30 and the conductive connection member 25 are connected in a plane. To be precise, the conductive band 30 and the conductive connection member 25 are connected in a curved face.

The conductive band 30 and the conductive connection member 25 may be made of different conductive materials or the same conductive material. The conductive band 30 and the conductive connection member 25 may be individually formed as separate components or integrally formed. Examples of the conductive material include a conductive metal material such as copper, silver, and gold, a conductive polymer, and the like. Examples of the conductive polymer includes, but are not limited to, polypyrrole, polythiophene, polyacetylene, and polyaniline.

The guidewire core 20 can be made of a conductive material. When the guidewire core 20 is made of a conductive material such as stainless steel, the guidewire core 20 itself can be used as a ground electrode. A high-conductivity metal layer (not illustrated) may be formed on the surface of the guidewire core 20. The high-conductivity metal layer is not limited to metals such as copper, gold, and silver. The high-conductivity metal layer may be made of a conductive polymer. The high-conductivity metal layer 29 is formed on the surface of the guidewire core 20, so that a return path for using the guidewire core 20 as a ground layer (GND) can be ensured. The guidewire core 20 alone can also be used as a ground electrode.

If the guidewire core 20 is not used as the electrical ground, any of the multiple conductive traces 22 can be used as the electrical ground. The guidewire core 20 and any one of the conductive traces 22 can also be used as the electrical ground.

Figure 4:
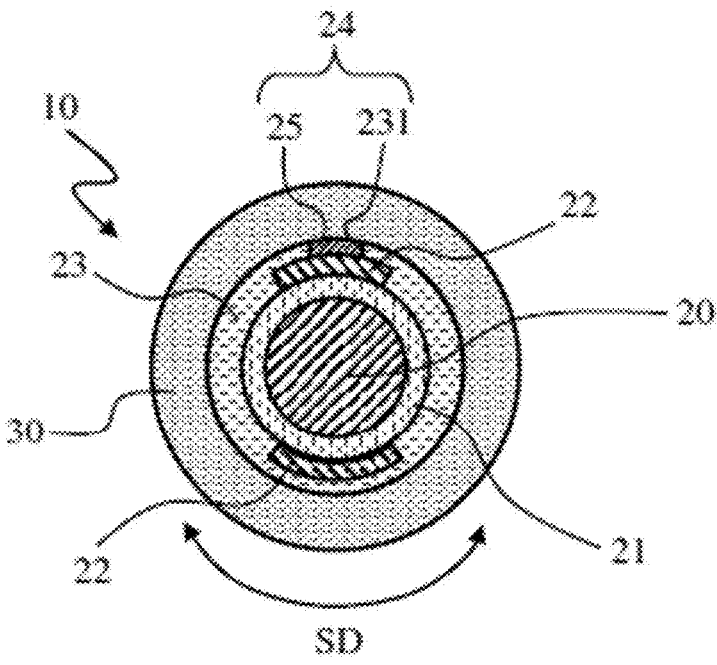
FIG. 4 is a sectional view that is viewed from the arrow IV-IV direction in FIG. 3.
Figure 5:
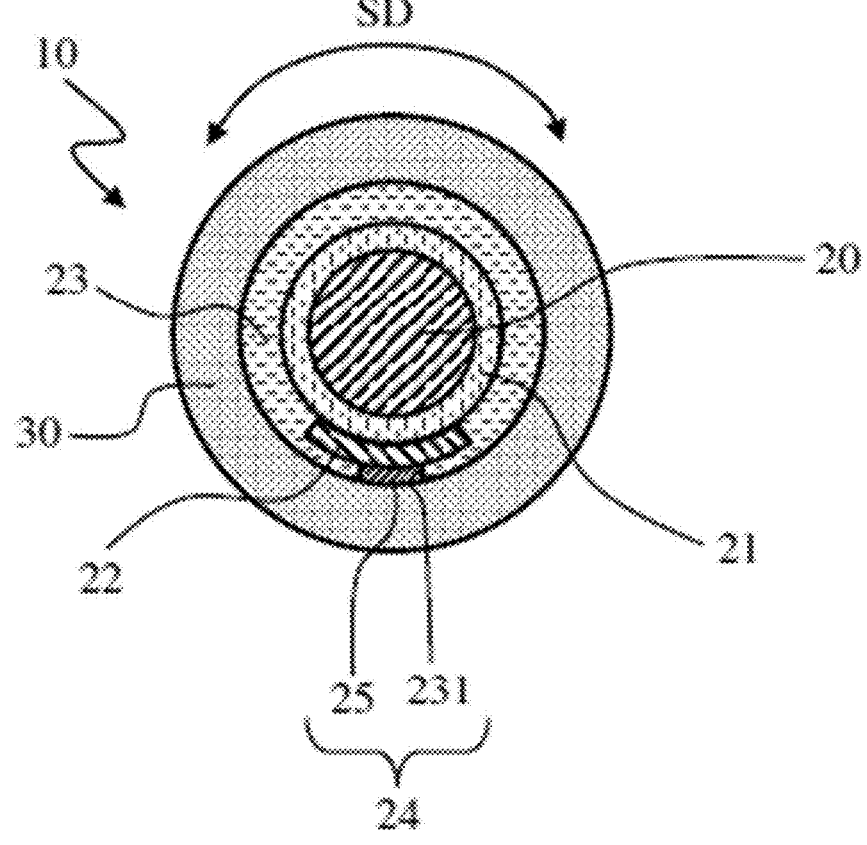
FIG. 5 is a sectional view that is viewed from the arrow V-V direction in FIG. 3.

FIG. 4 is a sectional view that is viewed from the arrow IV-IV direction in FIG. 3. FIG. 5 is a sectional view that is viewed from the arrow V-V direction in FIG. 3. As described above, the first insulating layer 21 is formed over the whole circumference on the surface of the guidewire core 20. On the surface of the first insulating layer 21, the multiple conductive traces 22 are formed spaced apart from each other in the side direction of the guidewire core 20. The second insulating layer 23 is formed so as to cover both the first insulating layer 21 and the multiple conductive traces 22. The first insulating layer 21, the conductive traces 22, and the second insulating layer 23 are formed in a build-up manner. For the first insulating layer 21 and the second insulating layer 23, a material according to properties required for the guidewire 10 can be used. The properties required for these insulating layers 21 and 23 include e.g. electrical insulation, core adhesiveness, dielectric property (low c), heat resistance, sterilization resistance, scratch resistance, abrasion resistance, chemical resistance, good slidability, water and moisture resistance, rust resistance, adhesiveness with hydrophilic coating agents (hyaluronic acid, silicone, etc.), and the like.

The properties of the first insulating layer 21 can be different from those of the second insulating layer 23. In an example, the first insulating layer 21 may be made of a material having a dielectric constant lower than of the second insulating layer 23. When the dielectric constant of the first insulating layer 21 is decreased, a parasitic capacitance between the conductive traces 22 and the guidewire core 20 can be decreased. That means, when the guidewire core 20 is used as an electrical wiring together with the conductive traces 22, the mutual capacitance between the conductive traces 22 and the guidewire core 20 tends to be significantly higher than the mutual capacitance between the conductive traces. When suppressing increase in this mutual capacitance, it is effective that the first insulating layer 21 sandwiched between the conductive traces 22 and the guidewire core 20 is made of a dielectric material having a lower dielectric constant. In another example, the first insulating layer 21 may be made of a material having a higher adhesiveness with the surface of the guidewire core 20 than of the second insulating layer 23. In yet another example, the second insulating layer 23 may be made of a material having a moisture resistance higher than of the first insulating layer 21.

Examples of the material that can be used for the first insulating layer 21 and/or the second insulating layer 23 include an epoxy resin, a glass epoxy resin, a bismaleimide triazine resin, BCB, polyimide, polyamide, polyamideimide, polyurethane, LCP (liquid crystal polymer), PE (polyethylene), PET (polyethylene terephthalate), PFA (perfluoroalkoxy fluororesin), PTFE (polytetrafluoroethylene), ETFE (copolymer of tetrafluoroethylene (C2F4) and ethylene (C2H4)), PEEK (polyetheretherketone), a parylene resin, solder resist, and the like.

As an example, the first insulating layer 21 may be made of a polyimide, and the second insulating layer 23 may be made of a polyimide (filler-containing reinforced grade). As another example, the first insulating layer 21 may be made of an LCP, and the second insulating layer 23 may be made of a polyimide. As yet another example, the first insulating layer 21 may be made of an LCP, and the second insulating layer 23 may be made of a PEEK. As yet another example, the first insulating layer 21 may be made of a polyimide, and the second insulating layer 23 may be made of a PTFE. As another example, the first insulating layer 21 may be made of a polyimide, and the second insulating layer 23 may be made of a parylene.

The width and thickness dimensions of each conductive trace 22 can be set in accordance with the intended use of the conductive trace 22. The width and thickness dimensions of each conductive band 30 can be set in accordance with the intended use of the conductive band 30.

FIG. 6 is a top view of one end side in the length direction of a guidewire 10A, illustrating an arrangement relation between each conductive trace 22, each electrical connection section 24, and each conductive band 30. Although FIG. 6 is explained with reference to two conductive traces 22 (1) and 22 (2) as an example, the number of the conductive traces 22 is not limited to two. The guidewire 10A can also include three or more conductive traces 22. The arrangement illustrated in FIG. 6 can be applied to both end sides in the length direction of the guidewire 10A, i.e. at least either the distal end side or the proximal end side of the guidewire. In FIG. 6, the configuration on the distal end side of the guidewire 10A is explained. That means, the right side in FIG. 6 corresponds to the distal end side of the guidewire 10A. Herein, numbers in parentheses, (1) and (2) are appended accompanying the symbols indicating these configurations, for the purpose of distinguishing the multiple conductive traces 22, the multiple electrical connection sections 24, and the multiple conductive bands 30.

An end 221 (1) of one conductive trace 22 (1) is formed in a straight shape (rectangular shape) extending toward the distal end side of the guidewire core 20. An end 221 (2) of the other one conductive trace 22 (2) extends toward a more distal end side of the guidewire core 20 than the end 221 (1) of the conductive trace 22 (1) and bends at an about 90-degree angle toward the conductive trace 22 (1). Thereby, the distal end side of the conductive trace 22 (2) is formed in an almost L-shape as a whole.

A trace width TW11 of the conductive trace 22 (1) and a trace width TW12 (trace width TW12 in the length direction) of the conductive trace 22 (2) except for the end 221 (2) are set to be substantially the same (TW11=TW12). A trace width TW2 of the end 221 (2) of the conductive trace 22 (2) can be larger than the trace width TW12 in the length direction (TW2>TW12). The end 221 (2) having the width TW2 larger than the trace width TW12 in the length direction can be referred to as e.g. a flag section. Alternatively, the end 221 (2) can be referred to as a large-area section, or a land section. The terms of the flag section, the large-area section, and the like apply to other ends 221.

The ends 221 (1) and 221 (2) of the multiple conductive traces 22 (1) and 22 (2) are arranged in parallel to the length direction of the guidewire core 20. An electrical connection section 24 (1) is disposed on the end 221 (1) of one conductive trace 22 (1). An electrical connection section 24 (2) is disposed on the end 221 (2) of the other one conductive trace 22 (2). A line O2 passing through the center of each of the multiple electrical connection sections 24 (1) and 24 (2) is substantially parallel to the longitudinal axis O1 of the guidewire core 20. Each of the electrical connection sections 24 (1) and 24 (2) need not be arranged exactly in the straight line O2, and may be arranged so as to be somewhat offset from the circumferential direction of the guidewire core 20 (minor axis direction of the guidewire core). In other words, it is only necessary to place each of the electrical connection sections 24 (1) and 24 (2) within a predetermined range where a manufacture tolerance and the like are taken into consideration. Alternatively, a center position (centroid position) of the electrical connection section 24 (1) disposed on one conductive trace 22 (1) only needs to be within a range where a width dimension W1 of the conductive trace 22 (1) and a width dimension W2 in the circumferential direction of the end 221 (2) of the other one conductive trace 22 (2) overlap with each other.

A dimension L1 from the distal end of the end 221 (1) of the conductive trace 22 (1) to the proximal end of the end 221 (2) of the conductive trace 22 (2) can be larger than a dimension L2 of the gap 28 in the circumferential direction (SD direction) between the conductive trace 22 (1) and the conductive trace 22 (2). The dimension L1 and the dimension L2 may be substantially equal, or the dimension L1 may be shorter than the dimension L2. An example in which three or more electrical connection sections 24 are arranged in the longitudinal axis O1 of the guidewire core 20 will be described below.

Each of the electrical connection sections 24 (1) and 24 (2) has conductive bands 30 (1) and 30 (2) respectively. The electrical connection section 24 (1) electrically connects the conductive trace 22 (1) with the conductive band 30 (1) via the conductive connection member 25 (not illustrated in FIG. 6). The electrical connection section 24 (2) electrically connects the conductive trace 22 (2) with the conductive band 30 (2) via the conductive connection member 25 (also not illustrated in FIG. 6).

Figure 7:
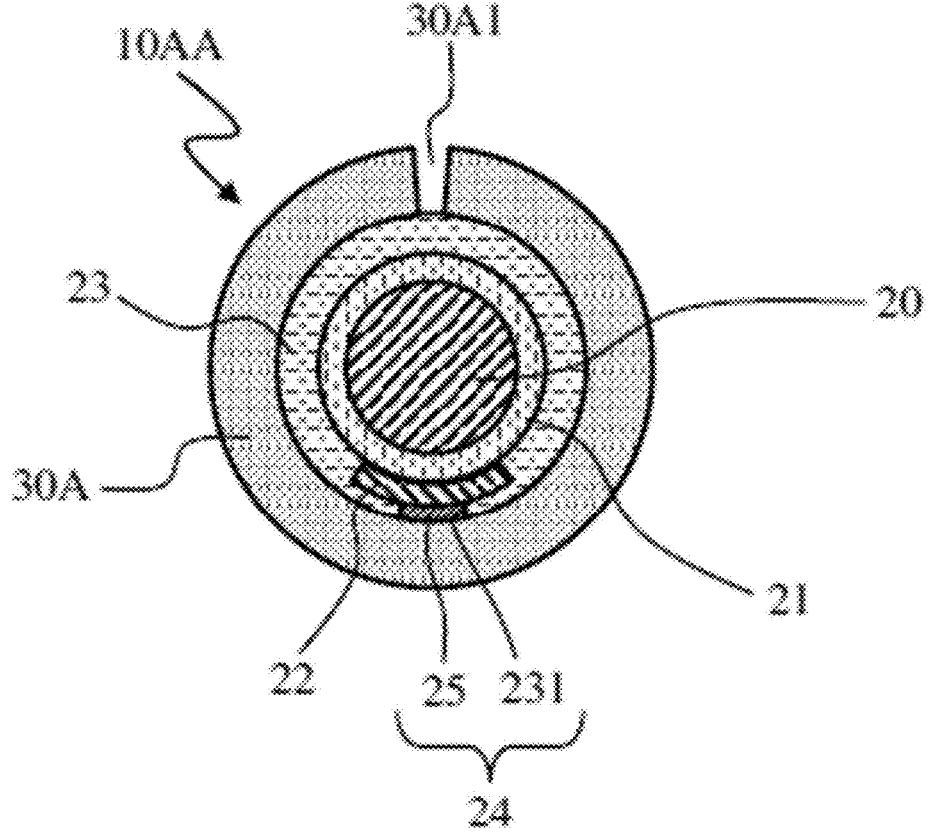
FIG. 7 is a sectional view that is viewed from the same direction as in FIG. 5, illustrating a variation of the conductive band.

FIG. 7 illustrates a variation of FIG. 5. A conductive band 30A of a guidewire 10AA may be formed so as to have a C-shaped cross-section with a gap 30A1 in the circumferential direction. For example, the conductive band 30A can be attached to the guidewire core 20 by covering the second insulating layer 23 from the outside with the conductive band 30A having the C-shaped cross-section and then swaging them.

Some relationships between the multiple conductive traces 22, the multiple electrical connection sections 24, and the multiple conductive bands 30 will be explained with reference to FIG. 8A to FIG. 8C and FIG. 9. FIG. 8A to FIG. 8C and FIG. 9 are diagrams in which the circumferential face of the guidewire is developed in a plane for the purpose of understanding the arrangement relation of the conductive traces 22 and the electrical connection sections 24, and the like. In FIG. 8A to FIG. 8C and FIG. 9, numbers are appended in parentheses accompanying the symbols for the purpose of distinguishing the respective conductive traces 22 and the respective electrical connection sections 24 from each other. In FIG. 8A to FIG. 8C and FIG. 9, the guidewire core 20 and the insulating layers 21 and 23 are not illustrated, and the arrangement of the respective conductive traces 22, the respective electrical connection sections 24, and the respective conductive bands 30 is schematically illustrated. In the following figures, a large alphabetic character accompanying the symbol of the guidewire is also appended to the conductive traces 22, the electrical connection sections 24, and the like to distinguish them from the configurations described in the other examples.

Figure 8A:
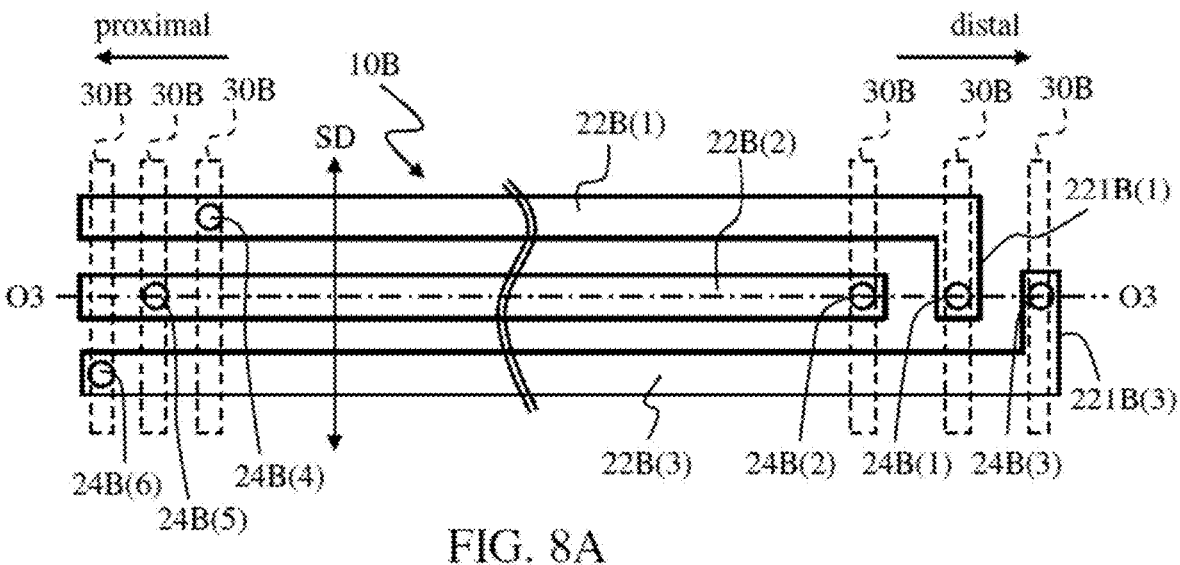
FIG. 8A is a schematic diagram illustrating a relationship between the multiple conductive traces and the multiple electrical connection sections.

FIG. 8A illustrates three conductive traces 22B (1) to 22B (3) as an example of the multiple conductive traces. The conductive trace 22B (2) located in the center of the figure is formed in a straight shape and has no flag section. In contrast, flag sections 221B (1) and 221B (3) extending in the straight line O2 where an end of the conductive trace 22B (2) is located are formed on distal end sides of the conductive traces 22B (1) and 22B (3) that are arranged spaced apart from each other in the circumferential direction of the guidewire core 20 so as to sandwich the conductive trace 22B (2) therebetween. No frag section is formed on proximal end sides of the respective conductive traces 22B (1) to 22B (3).

In the conductive trace 22B (1) on the upper side of the figure, an electrical connection section 24B (1) is disposed on the distal-side end 221B (1), and an electrical connection section 24B (4) is disposed on the proximal end side. In the conductive trace 22B (2) on the center of the figure, an electrical connection section 24B (2) is disposed on the distal end side, and an electrical connection section 24B (5) is disposed on the proximal end side. In the conductive trace 22B (3) on the lower side of the figure, an electrical connection section 24B (3) is disposed on the distal-side end 221B (3), and an electrical connection section 24B (6) is disposed on the proximal end side.

Conductive bands 30B are disposed on each of the electrical connection sections 24B (1) to 24B (6). Thereby, the conductive traces 22B (1) to 22B (6) are electrically connected with the corresponding conductive bands 30B via the electrical connection sections 24B (1) to 24B (6) respectively. The distal end sides of the conductive traces 22B (1) to 22B (6) are electrically connected to the sensor 52 (not illustrated in FIG. 8 and FIG. 9) via the conductive bands 30B. The proximal end sides of the conductive traces 22B (1) to 22B (6) are electrically connected to an external apparatus (not illustrated) via the conductive bands 30. This explanation can also be equally applied to the examples illustrated in FIG. 8B, FIG. 8C, and FIG. 9.

In a guidewire 10B illustrated in FIG. 8A, the multiple electrical connection sections 24B (1) to 24B (3) on the distal end side are arranged in a line O3 parallel to the longitudinal axis O1 (not illustrated) of the guidewire core 20 (not illustrated). The multiple electrical connection sections 24B (4) to 24B (6) on the proximal end side are arranged along an SD direction (also referred to as the side direction SD) that is the circumferential direction of the guidewire core 20. Thus, only the electrical connection sections 24B (1) to 24B (3) on the distal end sides of the multiple first conductive traces 22B (1) to 22B (3) may be arranged along the straight line O3.

Figure 8B:
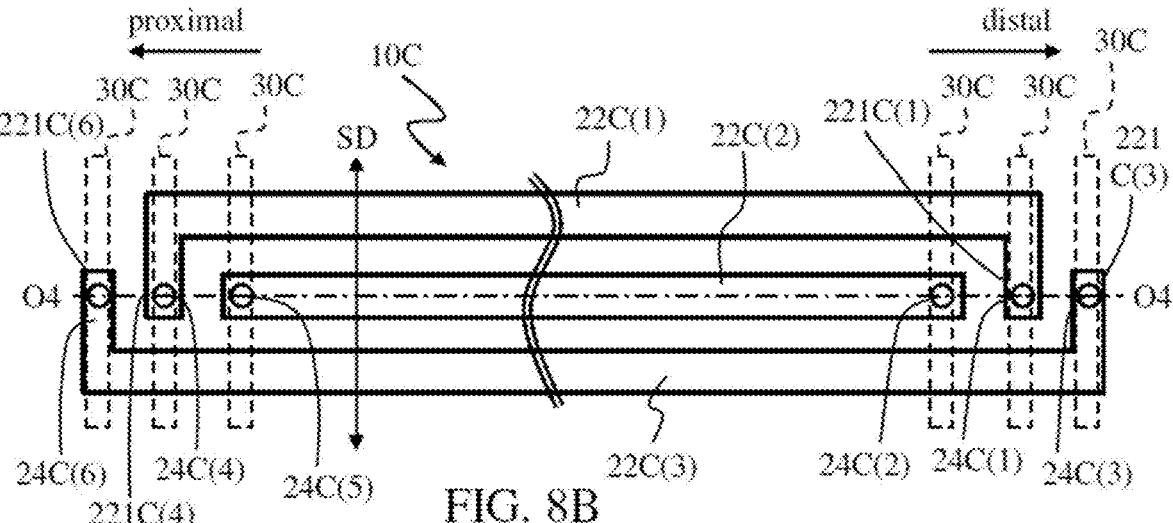
FIG. 8B is a schematic diagram illustrating another relationship between the multiple conductive traces and the multiple electrical connection sections.

A guidewire 10C illustrated in FIG. 8B has three conductive traces 22C (1) to 22C (3) as an example of multiple conductive traces. The conductive trace 22C (2) located in the center of the figure is formed in a straight shape and has no flag section. Flag sections 221C (1) and 221C (3) extending in the straight line O4 where an end of the conductive trace 22C (2) is located are formed on proximal and distal end sides of the conductive traces 22C (1) and 22C (3) that are arranged spaced apart from each other in the circumferential direction of the guidewire core 20 so as to sandwich the conductive trace 22C (2) therebetween. That means, the flag sections 221C (1) and 221C (3) extending while bending at right angle toward the central conductive trace 22C (2) are formed on the proximal and distal end sides of the conductive traces 22C (1) and 22C (3). When the conductive trace 22C (2) is disposed parallel to the longitudinal axis O1 of the guidewire core 20, the straight line O4 connecting between centers of the both longitudinal ends of the conductive trace 22C (2) is substantially parallel to the longitudinal axis O1 of the guidewire core 20.

In the conductive trace 22C (1), an electrical connection section 24C (1) is disposed on the distal-side end 221C (1), and an electrical connection section 24C (4) is disposed on the proximal end side. In the conductive trace 22C (2), an electrical connection section 24C (2) is disposed on the distal end side, and an electrical connection section 24C (5) is disposed on the proximal end side. In the conductive trace 22C (3), an electrical connection section 24C (3) is disposed on the distal-side end 221C (3), and an electrical connection section 24C (6) is disposed on a proximal-side end 221C (6).

In the guidewire 10C illustrated in FIG. 8B, the multiple electrical connection sections 24C (1) to 24C (3) located on the distal end side and the multiple electrical connection sections 24C (4) to 24C (6) located on the proximal end side are arranged in the straight line O4 substantially parallel to the longitudinal axis O1 of the guidewire core 20.

Figure 8C:
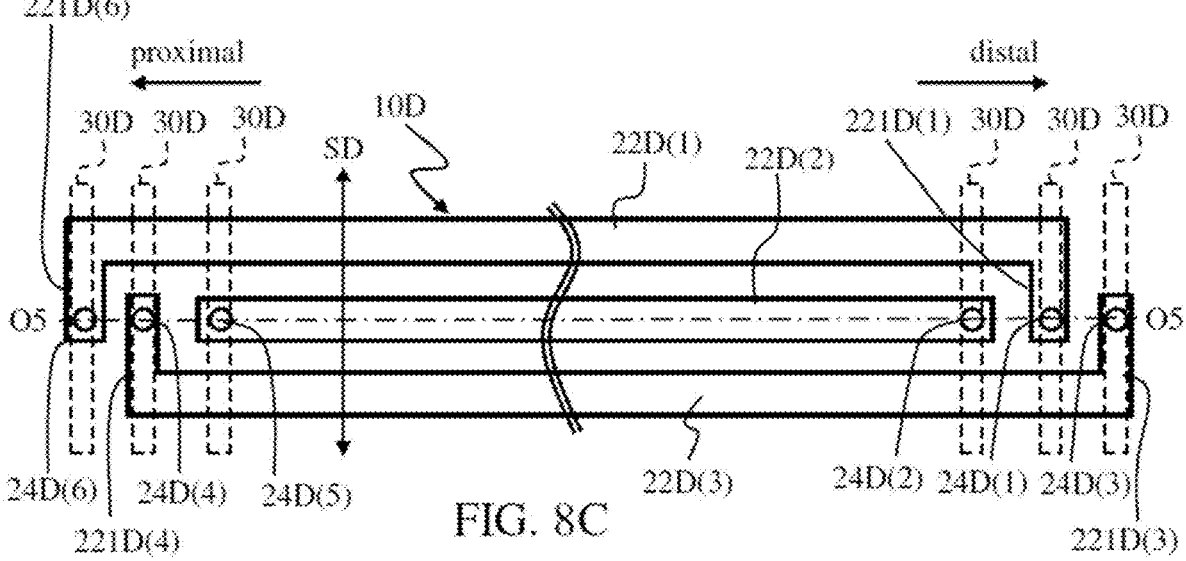
FIG. 8C is a schematic diagram illustrating yet another relationship between the multiple conductive traces and the multiple electrical connection sections.

A guidewire 10D illustrated in FIG. 8C also has three conductive traces 22D (1) to 22D (3) as an example of multiple conductive traces. The conductive trace 22D (2) is formed in a straight shape and has no flag section. Flag sections 221D (1) and 221D (3) extending in a straight line O5 where an end of the conductive trace 22D (2) is located are formed on the distal end sides of the conductive traces 22D (1) and 22D (3) that are arranged spaced apart from each other in the circumferential direction of the guidewire core 20 so as to sandwich the conductive trace 22D (2) therebetween. Flag sections 221D (4) and 221D (6) extending in the straight line O5 where the end of the conductive trace 22D (2) is located are formed on the proximal end sides of the conductive traces 22D (1) and 22D (3). The straight line O5 is a line connecting between centers of the both longitudinal ends of the conductive trace 22D (2) located in the circumferential center of the guidewire 10D. When the conductive trace 22D (2) is arranged parallel to the longitudinal axis O1 of the guidewire core 20, the straight line O5 is substantially parallel to the axis O1.

When comparing the guidewire 10D illustrated in FIG. 8C with the guidewire 10C illustrated in FIG. 8B, the conductive traces 22D (1) and 22D (3) are different from the conductive traces 22C (1) and 22C (3) in length dimension. In the example of FIG. 8B, the both ends 221C (3) and 221C (6) of the conductive trace 22C (3) are located more outside in the length direction of the guidewire core 20 than the both ends 221C (1) and 221C (4) of the conductive trace 22C (1). That means, the length dimension of the conductive trace 22C (3) is larger than the length dimension of the conductive trace 22C (1). In contrast, in the example of FIG. 8C, the length dimensions of the conductive trace 22D (1) and the conductive trace 22D (3) are substantially equal.

In the example of FIG. 8B, the distal-side end 221C (3) of the conductive trace 22C (3) is located on the most distal end side in the length direction of the guidewire core, and the proximal-side end 221C (6) of the conductive trace 22C (3) is located on the proximal end side in the length direction of the guidewire core. The conductive trace 22C (2) is formed so as to have the shortest length dimension. The distal-side end 221C (1) of the conductive trace 22C (1) is located between the distal-side end 221C (3) of the conductive trace 22C (3) and the distal-side end of the conductive trace 22C (2). The proximal-side end 221C (4) of the conductive trace 22C (1) is located between the proximal-side end 221C (6) of the conductive trace 22C (3) and the proximal-side end of the conductive trace 22C (2).

In contrast, in the example of FIG. 8C, on the distal end side of the guidewire core 20, the distal-side end 221D (3) of the conductive trace 22D (3) is located on the most distal end side in the length direction of the guidewire core 20. The distal-side end 221D(1) of the conductive trace 22D (1) is located on the proximal end side with respect to the distal-side end 221D (3). The distal end side of the conductive trace 22D (2) is located on the proximal end side with respect to the distal-side end 221D (1). On the proximal end side of the guidewire core, the proximal-side end 221D (6) of the conductive trace 22D (1) is located on the most proximal end side in the length direction of the guidewire core 20. The proximal-side end 221D (4) of the conductive trace 22D (3) is located on the distal end side with respect to the proximal-side end 221D (6). The proximal-side end of the conductive trace 22D (2) is located on the distal end side with respect to the proximal-side end 221D (4).

As illustrated in FIG. 8C, the length dimensions (wiring length) of the conductive trace 22D (1) and the conductive trace 22D (3) are substantially equal, so that a wiring pair for differential signals can be obtained. Examples of the isometric wiring pair will be further described below.

Figure 9:
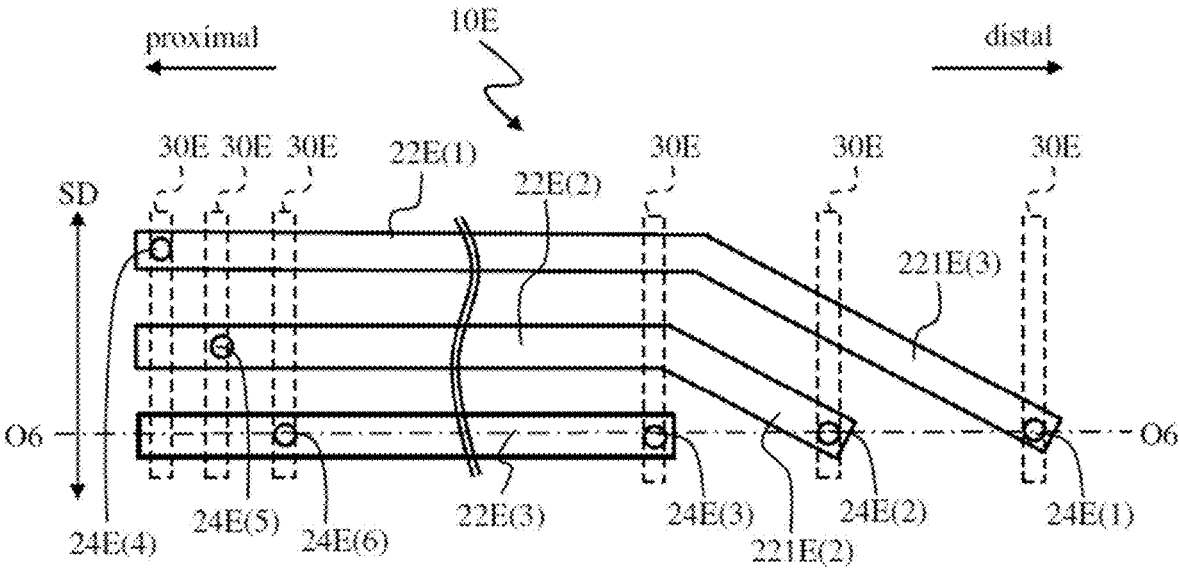
FIG. 9 is a schematic diagram illustrating yet another relationship between the multiple conductive traces and the multiple electrical connection sections.

As illustrated in FIG. 9, distal end sides of the conductive traces 22E (1) to 22E (3) may be bent at an angle other than right angle. In a guidewire 10E in FIG. 9, distal end sides of conductive traces 22E (1) and 22E (2) that are spaced apart from each other in the circumferential direction (SD direction) from a line O6 obliquely extend toward the line O6 such that electrical connection sections 24E (1) to 24E (3) on the distal end side of each of conductive traces 22E (1) to 22E (3) are located in the line O6 substantially parallel to the longitudinal axis O1 of the guidewire core 20 (not illustrated).

The conductive trace 22E (3) is located in the line O6 and formed in a linear (rectangular) shape. The electrical connection section 24E (3) is disposed on the distal end side of the conductive trace 22E (3), and an electrical connection section 24E (6) is disposed on the proximal end side of the conductive trace 22E (3).

The conductive trace 22E (2) is formed spaced apart from the conductive trace 22E (3) in the circumferential direction of the guidewire core 20. The distal end side of the conductive trace 22E (2) extends toward the more distal end side of the guidewire core 20 than the distal end of the conductive trace 22E (3) and up to a position intersecting with the line O6. The electrical connection section 24E (2) is disposed on the distal end side of the conductive trace 22E (2), and an electrical connection section 24E (5) is disposed on the proximal end side of the conductive trace 22E (2).

The conductive trace 22E (1) is formed spaced apart from the conductive trace 22E (2) in the circumferential direction of the guidewire core 20. The distal end side of the conductive trace 22E (1) extends toward the more distal end side of the guidewire core 20 than the distal end of the conductive trace 22E (2) and up to a position intersecting with the line O6. The electrical connection section 24E (1) is disposed on the distal end side of the conductive trace 22E (1). The electrical connection section 24E (4) is disposed on the proximal end side of the conductive trace 22E (1).

Each of the electrical connection sections 24E (1) to 24E (6) has a conductive band 30E. Each of the conductive traces 22E (1) to 22E (6) is electrically connected with each corresponding conductive band 30E via the conductive connection member 25 (not illustrated) disposed on the corresponding electrical connection sections 24E (1) to 24E (6).

Figure 10:
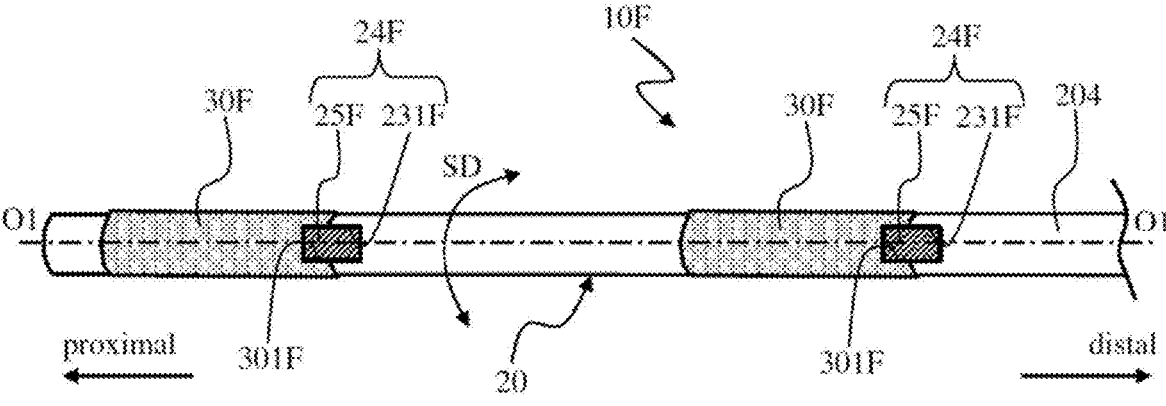
FIG. 10 is a plan view illustrating a state that the multiple electrical connection sections and the multiple conductive bands are electrically connected.

FIG. 10 is a plan view illustrating a state that multiple electrical connection sections 24F are electrically connected with multiple conductive bands 30F. FIG. 10 illustrates a proximal end side of a guidewire 10F (proximal end side of the guidewire core 20).

The conductive band 30F is formed in a cylindrical shape, an annular shape, or an almost C-shape. In the following explanation, a width direction of the conductive band refers to a direction along the longitudinal axis O1 of the guidewire core in a state that the conductive band is attached to the guidewire core. Thus, both ends in the width direction of the conductive band 30F refers to the proximal-side end of the guidewire core 20 and the distal-side end of the guidewire core 20.

An outer opening 301F is formed on the distal-side end of the both ends in the width direction of the conductive band 30F (length direction of the guidewire). The outer opening 301F is formed such that the distal-side end of the both ends in the width direction of the conductive band 30F is notched into a rectangular shape. The outer opening 301F is formed in a rectangular shape in which the distal end side is opened. The outer opening 301F can also be referred to as a notched section 301F.

The outer opening 301F of the conductive band 30F is attached to the guidewire core 20 so as to partially overlap with a first inner opening 231F opened on the second insulating layer 23 (not illustrated). A conductive connection member 25F such as solder is charged into the inner opening 231F from the outer opening 301F, so that the conductive band 30F is electrically and mechanically connected with the conductive trace 22 (not illustrated in FIG. 10). That means, the conductive band 30F is bonded or fixed to the conductive trace 22 and electrically connected with the conductive trace 22 by the conductive connection member 25F disposed inside the outer opening 301F and the first inner opening 231F.

A state that the conductive band 30F illustrated in FIG. 10 is attached to the guidewire core 20 will be explained with reference to FIG. 11A to FIG. 11D.

Figure 11A:
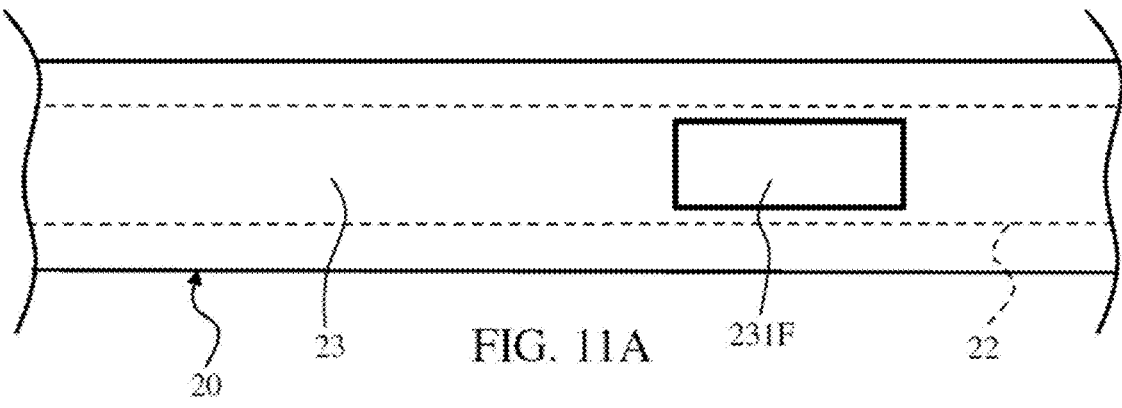
FIG. 11A is an enlarged plan view of one electrical connection section.

FIG. 11A is a plan view of the guidewire core 20. The rectangular first inner opening 231F is formed at a predetermined position of the second insulating layer 23. Since the first inner opening 231F is formed in a rectangular cylindrical shape so as to reach the surface of the first conductive trace 22, a portion of the conductive trace 22 is exposed within the first inner opening 231F.

Figure 11B:
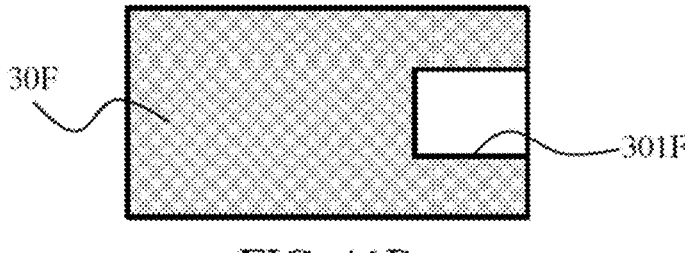
FIG. 11B is an enlarged plan view of one conductive band.

FIG. 11B is a plan view of one conductive band 30F. As described above, the distal end side of the both ends in the width direction of the conductive band 30F is notched into a rectangular shape to form the outer opening 301F.

Figure 11C:
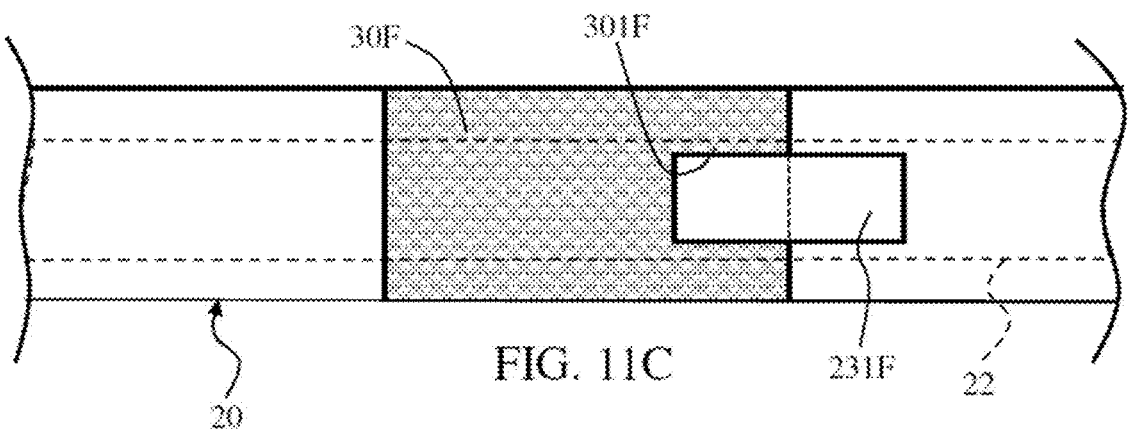
FIG. 11C is a plan view illustrating an arrangement in which a notched section of the conductive band and an opening of an insulating layer partially overlap with each other.

FIG. 11C illustrates a state that the conductive band 30F illustrated in FIG. 11B is attached to the guidewire core 20 illustrated in FIG. 11A. The conductive band 30F is attached to the outside of the guidewire core 20 such that the outer opening 301F overlaps with the proximal end side of the first inner opening 231F. The outer opening 301F can be attached to the guidewire core 20 as to overlap with e.g. almost half of an area of the first inner opening 231F.

Figure 11D:
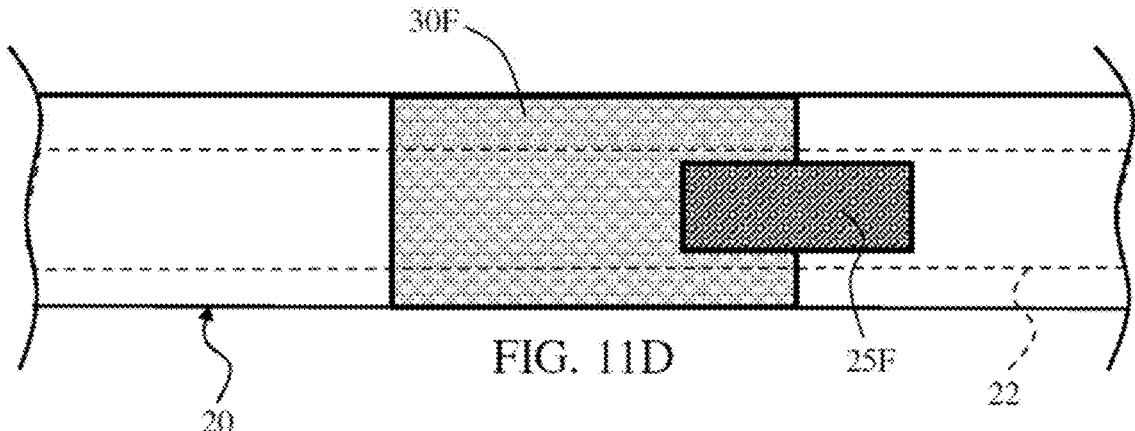
FIG. 11D is a plan view illustrating a state that the notched section is electrically connected with the opening via a conductive connection member.

FIG. 11D illustrates a state that the conductive band 30F is electrically and mechanically connected with the conductive trace 22 by injecting the conductive connection member 25F such as solder into the insides of the outer opening 301F and the first inner opening 231F. When the conductive band 30F is formed from a metal material and the conductive connection member 25F is made of a metal material such as solder, the area where the metal for forming the conductive band 30F and the metal for forming the conductive connection member 25F are joined can be made wider. This makes it possible to improve reliability of the electrical and mechanical connection between the conductive band 30F and the conductive trace 22.

Figure 12:
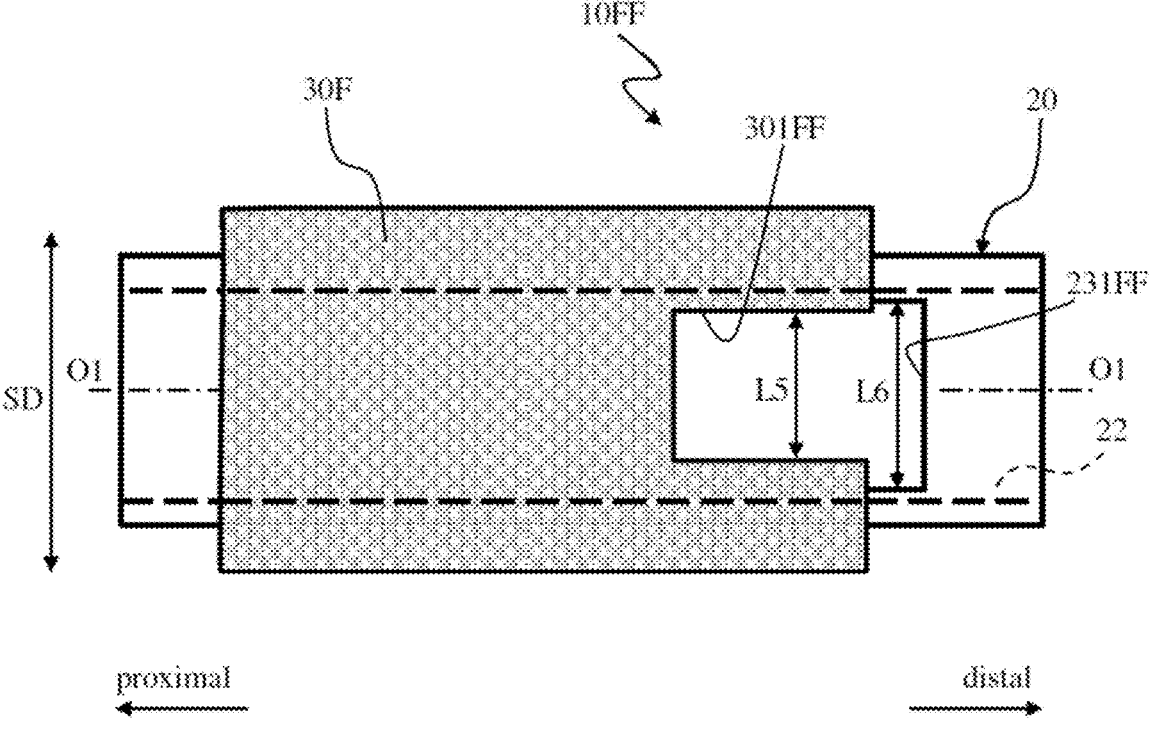
FIG. 12 is a diagram illustrating a relationship between the notched section of the conductive band and the opening of the insulating layer.

As illustrated in FIG. 12, an opening dimension L5 of an outer opening 301FF of a conductive band 30FF can also be set to be slightly smaller than an opening dimension L6 of a first inner opening 231FF. The opening dimensions L5 and L6 refer to circumferential (SD direction) lengths of the openings 301FF and 231FF respectively. The outer opening 301FF can be attached to the guidewire core 20 so as to overlap with almost half or more of an area of the first inner opening 231FF.

Figure 13:
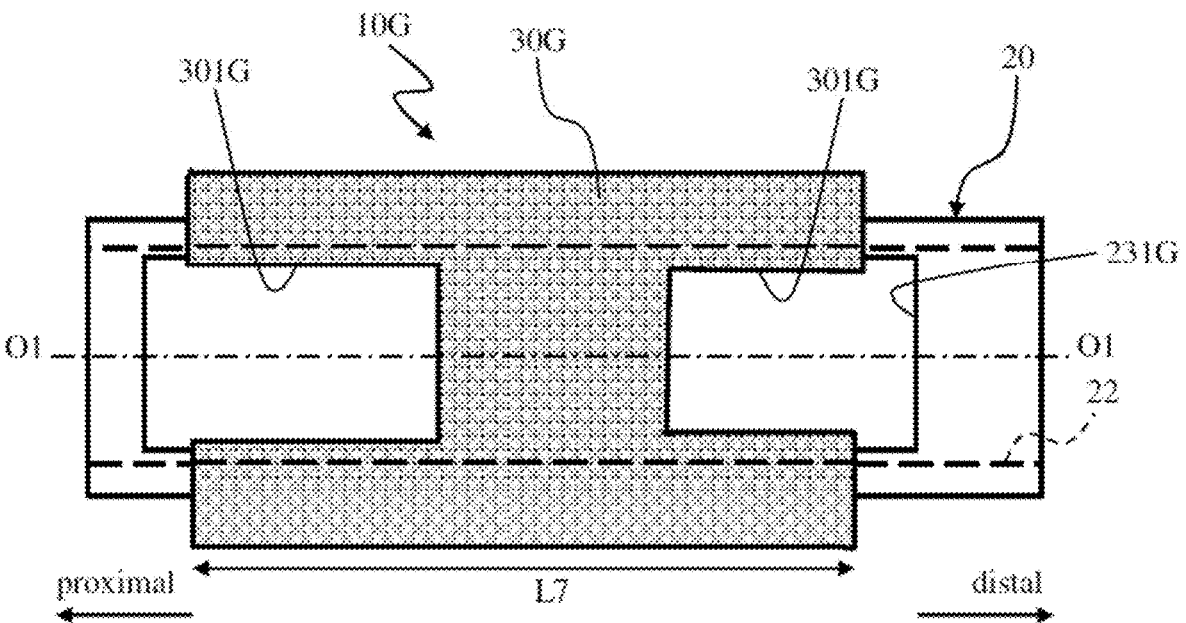
FIG. 13 is a diagram illustrating another relationship between the notched section of the conductive band and the opening of the insulating layer.

In a guidewire 10G illustrated in FIG. 13, an outer opening 301G that is opened on a side in the axis O1 direction is formed on both end sides in a width direction of a conductive band 30G. A first inner opening 231G is formed longer than a width dimension L7 of the conductive band 30G. The conductive band 30G is attached to the guidewire core 20 so as to be located at almost the center of the first inner opening 231G. The conductive connection member 25 (not illustrated) such as solder is charged into the first inner opening 231G from the inside of the outer opening 301G on both sides in the width direction of the conductive band 30G.

In the example illustrated in FIG. 13, a contact area between the conductive band 30G and the conductive connection member 25 can be increased compared to the examples illustrated in FIG. 11 or FIG. 12. Thus, in the guidewire 10G illustrated in FIG. 13, when the conductive band 30G and the conductive connection member 25 are both made of conductive metal materials, reliability of the electrical and mechanical connection between the conductive band 30G and the conductive trace 22 can be further improved.

Figure 14:
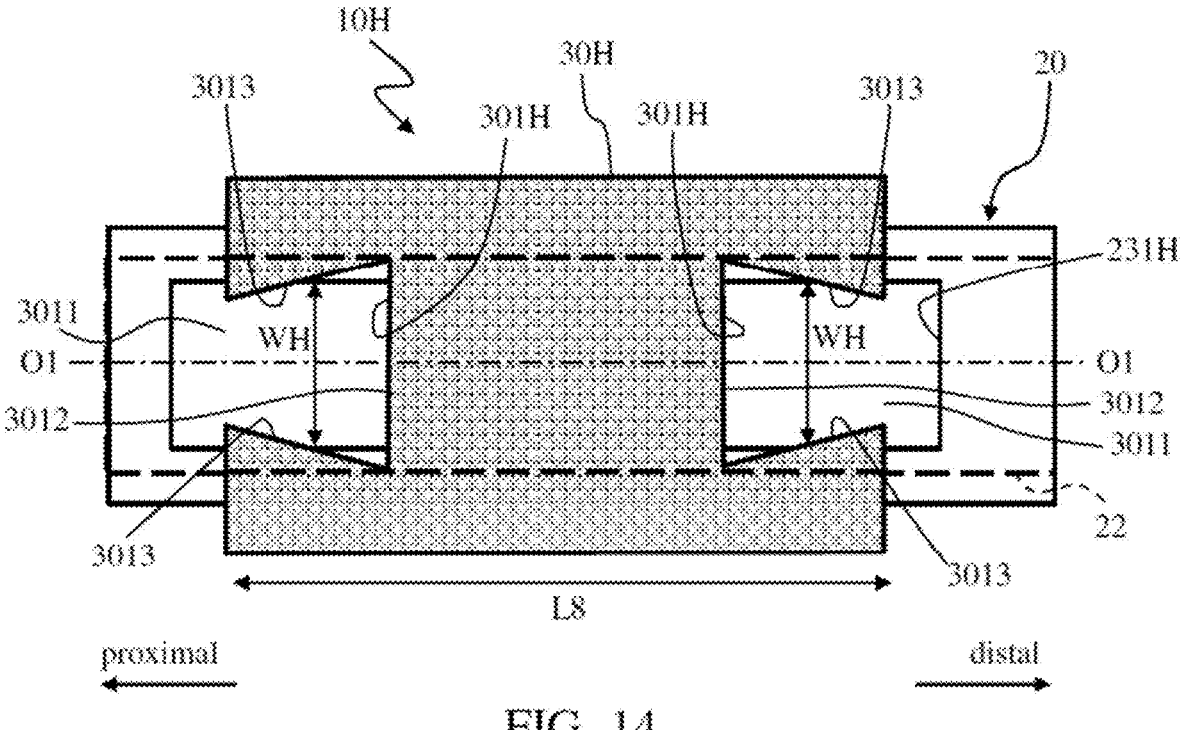
FIG. 14 is a diagram illustrating yet another relationship between the notched section of the conductive band and the opening of the insulating layer.

In a guidewire 10H illustrated in FIG. 14, outer openings 301H that are notched into an almost trapezoidal shape are formed on both sides in a width direction of a conductive band 30H. A first inner opening 231H is formed longer than a width dimension L8 of the conductive band 30H.

The outer opening 301H is formed into, in plan view, a trapezoidal shape that gradually widens from a position 3011 opened on one of the both ends in the width direction of the conductive band 30H toward a side 3012 located at a position deviating in the width direction of the conductive band 30H. The outer opening 301H may also be expressed as being formed in an inverse tapered shape. The inverse tapered shape means a shape in which an opening width WH gradually increases from the opened position 3011 toward the center in the width direction of the conductive band 30H. Conversely, each outer opening 301H is formed in a tapered shape in which the opening width WH gradually decreases from the side 3012 located near the middle in the width direction of the conductive band 30H toward the end (opened position 3011) of the conductive band 30H.

When the outer openings 301H are formed on the both sides in the width direction of the conductive band 30H, reliability of the electrical and mechanical connection between the conductive band 30H and the conductive trace 22 is improved, as described in the example of FIG. 13. Furthermore, the outer opening 301H is formed in the inverse tapered shape or the almost trapezoidal shape, and therefore has a side 3013 that is sloped with respect to the longitudinal axis O1 of the guidewire core 20. Thus, in plan view, the conductive band 30H can have not only the side 3012 orthogonal to the axis O1 but also the sides 3013 and 3013 intersecting with the axis O1 at an angle other than 90 degrees. Thereby, the conductive band 30H is electrically and mechanically connected to the conductive trace 22 via the conductive connection member 25 from multiple directions with different angles. Thus, when the guidewire 10H is inserted into a body tissue such as a blood vessel and moves therethrough, the position of the conductive band 30H can be prevented from being offset.

Figure 15:
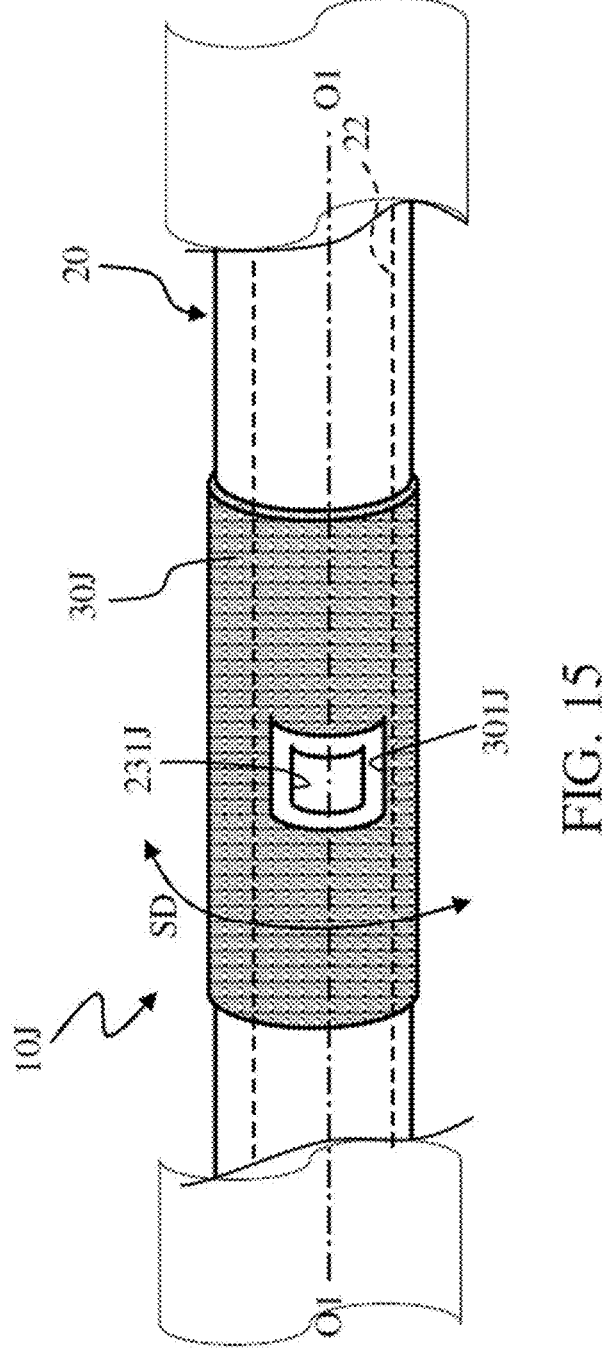
FIG. 15 is a diagram illustrating an example in which the opening of the conductive band is wider than the opening of the insulating layer.
Figure 16:
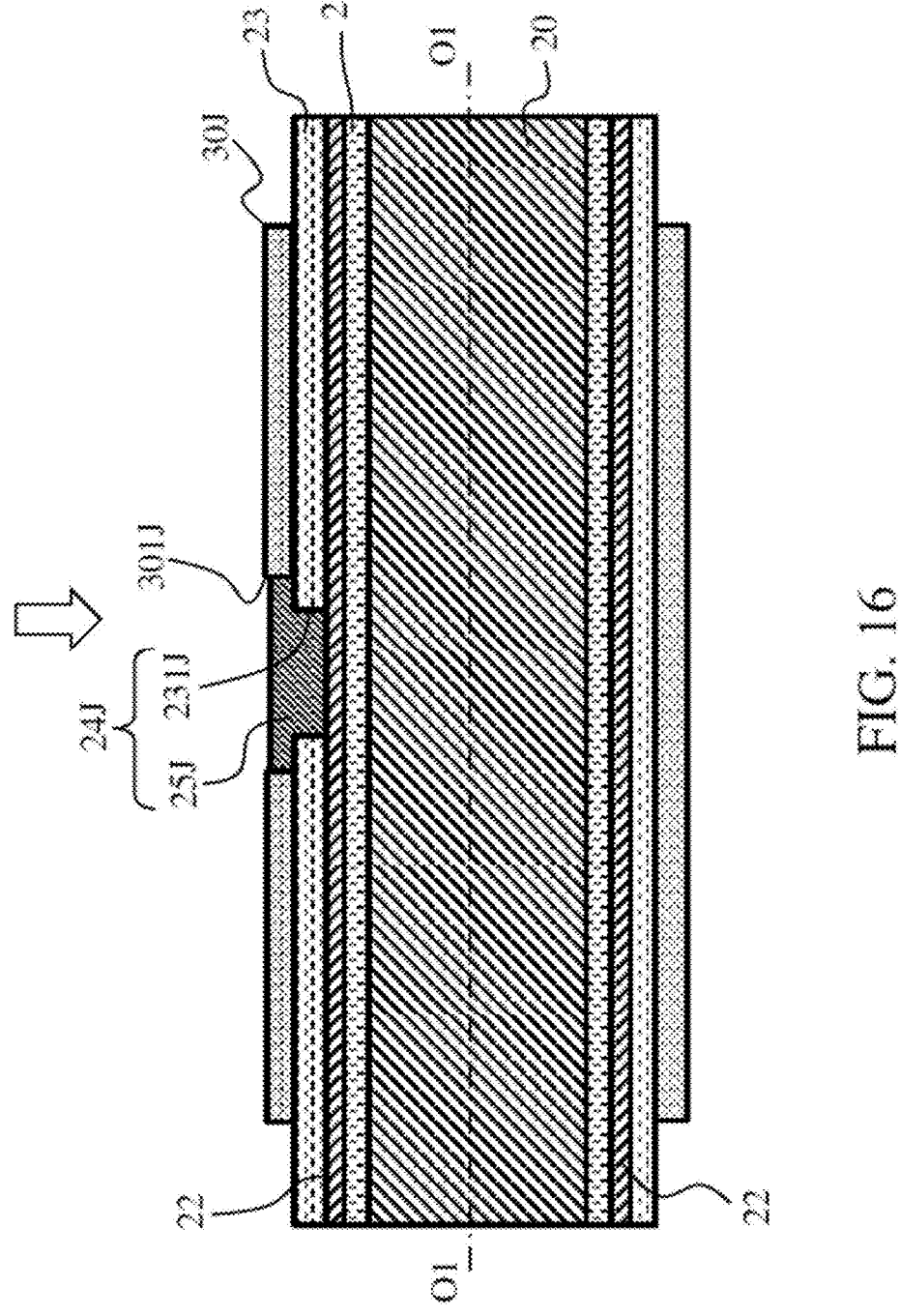
FIG. 16 is a longitudinal sectional view of the example of FIG. 15.
Figure 17:
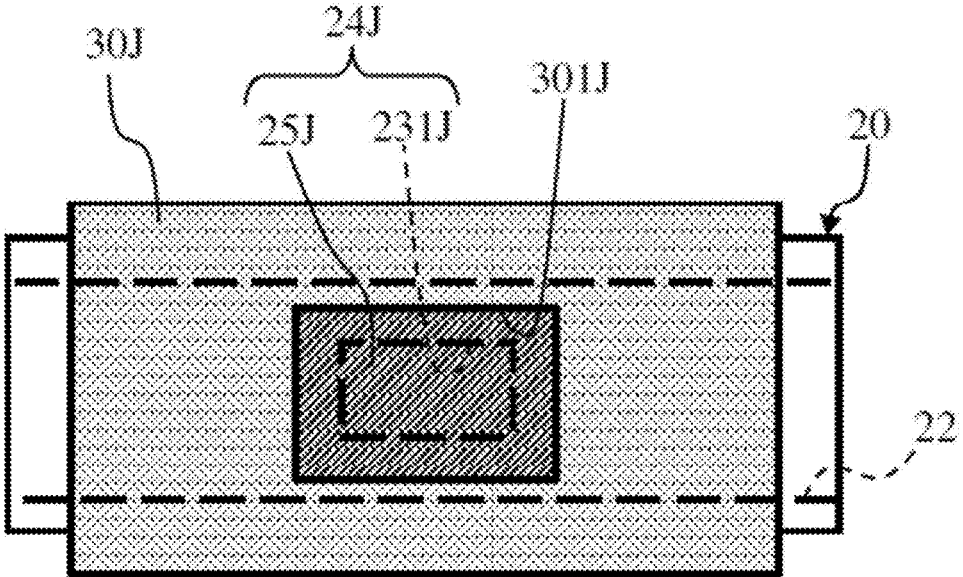
FIG. 17 is a plan view that is viewed from the arrow direction in FIG. 16.

In a guidewire 10J illustrated in FIG. 15 to FIG. 17, an area of an outer opening 301J is larger than an area of a first inner opening 231J. The rectangular outer opening 301J is formed in almost center of a conductive band 30J. For example, the center of the outer opening 301J is located on almost center in a width direction (axis O1 direction) of the conductive band 30J and on almost center of a circumferential direction (SD direction) of the conductive band 30J. However, the outer opening 301J may be located out of the center of the conductive band 30J. Multiple outer openings 301J may be formed on the conductive band 30J.

FIG. 16 is a longitudinal sectional view of the example of FIG. 15. A width dimension (dimension in the axis O1 direction) of the outer opening 301J is longer than a width dimension of the first inner opening 231J. A conductive connection member 25J such as solder is disposed inside the outer opening 301J and the first inner opening 231J.

FIG. 17 is a plan view that is viewed from the arrow direction in FIG. 16. As described above, the area of the outer opening 301J is larger than the area of the first inner opening 231J. In other words, the outer opening 301J is formed in a rectangular shape that is larger than the first inner opening 231J. For example, a shape of the outer opening 301J is similar to a shape of the first inner opening 231J. However, the scope of the present disclosure also includes a case where the outer opening 301J is different from the first inner opening 231J in shape. For example, the outer opening 301J may be different from the first inner opening 231J in aspect ratio. Furthermore, the outer opening 301J may be different from the first inner opening 231J in shape. For example, a case where the outer opening 301J is rectangular and the first inner opening 231J is triangular, or a case where the outer opening 301J is oval and the first inner opening 231J is perfect circle, is allowed. The scope of the present disclosure also includes combinations of shapes other than these combinations.

Figure 18:
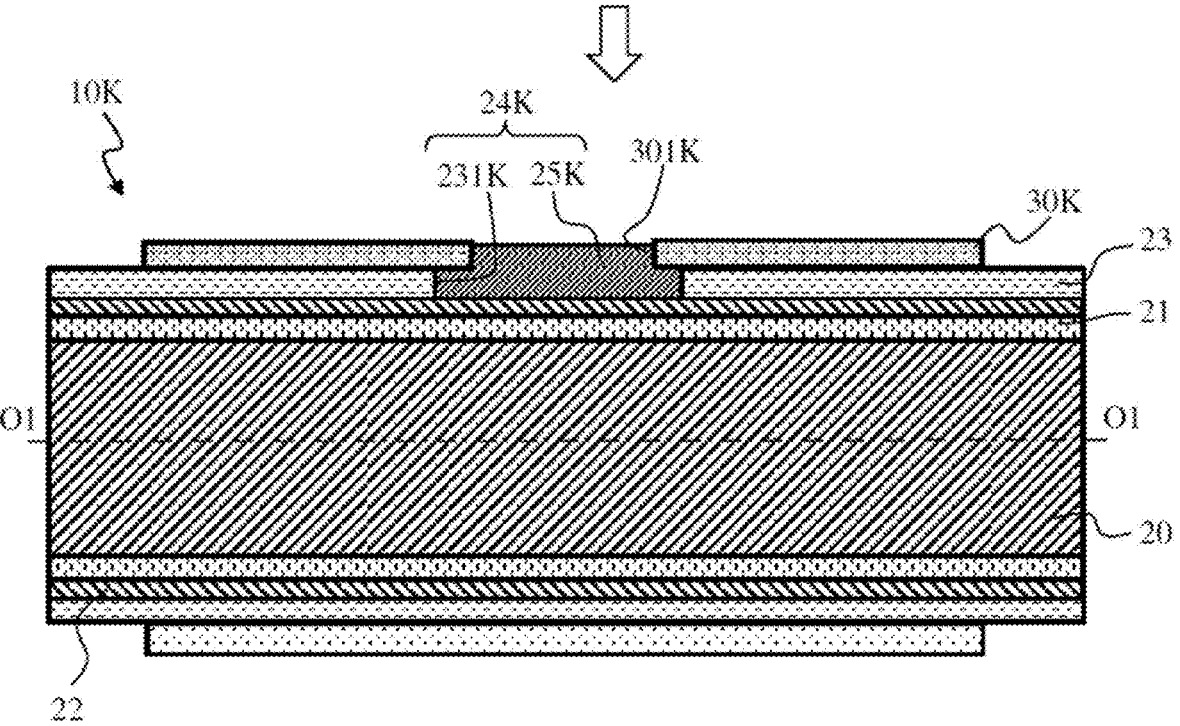
FIG. 18 is a longitudinal sectional view illustrating an example in which the opening of the insulating layer is wider than the opening of the conductive band.
Figure 19:
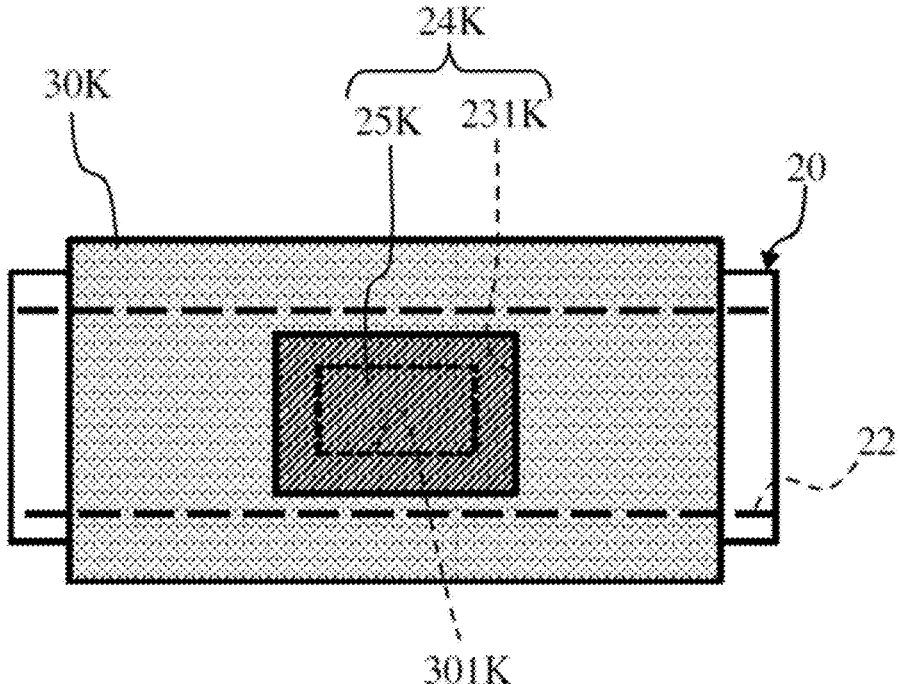
FIG. 19 is a plan view that is viewed from the arrow direction in FIG. 18.

In a guidewire 10K illustrated in FIG. 18 and FIG. 19, an area of a first inner opening 231K is larger than an area of an outer opening 301K. Thereby, a contact area between a conductive connection member 25K and the conductive trace 22 can be increased compared to that in the example of FIG. 16. Thus, reliability of the electrical and mechanical connection between a conductive band 30K and the conductive trace 22 can be improved. Shapes of the outer opening 301K and the first inner opening 231K may be similar to or different from each other.

FIG. 19 is a plan view that is viewed from the arrow direction in FIG. 18. The center of the outer opening 301K coincides with the center of the first inner opening 231K. The outer opening 301K is similar to the first inner opening 231K in shape. However, the scope of the present disclosure also includes a configuration in which the center of the outer opening 301K is offset from the center of the first inner opening 231K.

The conductive band 30K is electrically connected with the conductive trace 22 using solder, a conductive paste, or the like, and then an adhesive is applied on an outer circumference of the conductive band 30K or charged into the outer opening 301K, so that the conductive band 30K can also be mechanically connected to the guidewire core 20. Similarly, in other examples described above, the conductive band may be electrically connected with the conductive trace 22 of the guidewire 20 via the conductive material, and the conductive band may be mechanically connected with the guidewire 20 via a non-conductive material. Alternatively, as described above, the conductive band may be electrically and mechanically connected with the guidewire core 20 by using a material having both conductivity and adhesiveness, such as solder.

Figure 20:
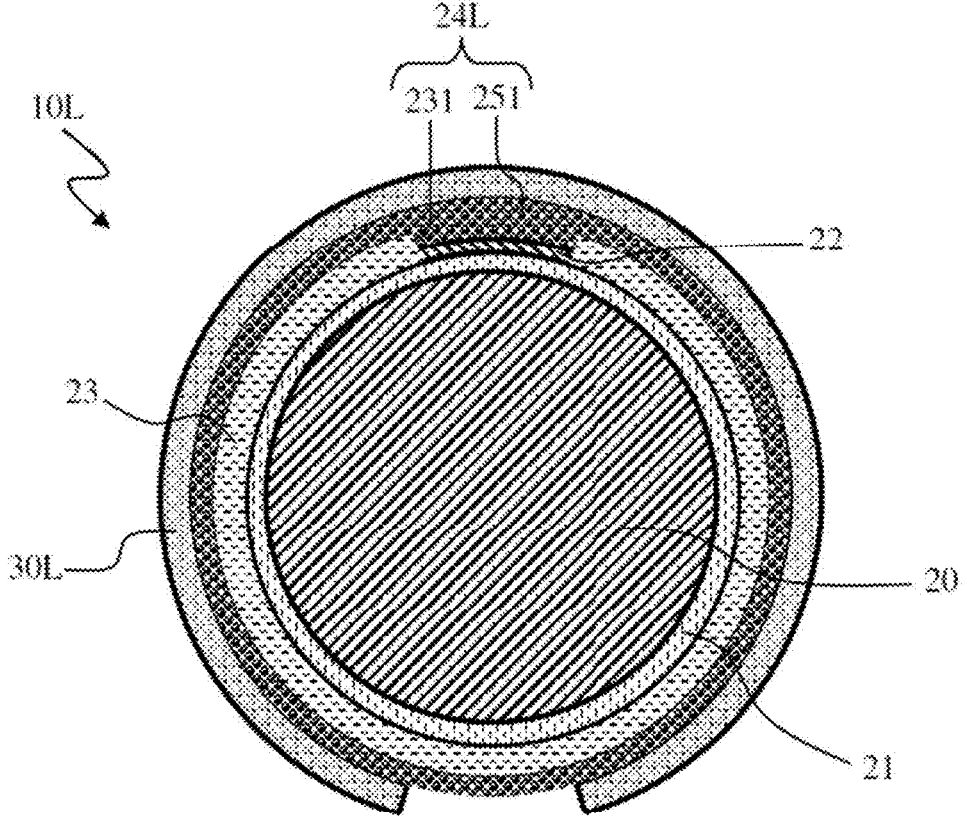
FIG. 20 is a cross-sectional view illustrating an example in which an anisotropic conductive material is used as the conductive connection member.

FIG. 20 is a cross-sectional view of a guidewire 10L, illustrating an example using an anisotropic conductive material as the conductive connection member. An anisotropic conductive layer 251 made of the anisotropic conductive material is disposed between the second insulating layer 23 and a conductive band 30L. An electrical connection section 24L is composed of the first inner opening 231 and the anisotropic conductive material layer 251 that has entered the first inner opening 231.

An anisotropic conductive material is applied or bonded to the surface of the second insulating layer and the inside of the first inner opening 231, and the outside of the anisotropic conductive material is covered with the conductive band 30L, which is pressure-bonded or thermocompression-bonded, so that the conductive band 30L can be electrically connected to the conductive trace 22, and the conductive band 30L can be mechanically attached to the guidewire core 20. This makes it more certain to electrically and mechanically connect the conductive band 30L to the guidewire core 20 compared to the case where the conductive band 30L is electrically connected with the conductive trace 22, which is then filled with an adhesive from the outside of the conductive band 30L for securing.

Examples of the anisotropic conductive material include ACF (Anisotropic Conductive Film), ACP (Anisotropic Conductive Paste), and ACR (Anisotropic Conductive Rubber). ACF is an encapsulated resin formed by dispersing conductive particles in a thermosetting epoxy resin. ACP is a paste formed by dispersing conductive particles in a thermosetting epoxy resin.

When the layer 251 is made of ACF or ACP, the layer 251 is covered with the conductive band 30L and thermocompression-bonded to form an anisotropic conductive path. The conductive path is a semipermanent path, allowing retention of the conductive state even if the conductive band 30L is removed. This makes it possible to achieve reliable adhesion and increased strength between the conductive band 30L and the polyimide constituting the insulating layer. On the other hand, ACR is electrically conducted only during pressurization, and the electrical conduction disappears once the pressurization is stopped.

The anisotropic conductive layer 251 is disposed between the conductive band 30L and the insulating layer 23 and conductive trace 22, so that the conductive band 30L can be electrically and mechanically connected with the insulating layer 23 and the conductive trace 22, resulting in durable electrical and mechanical connection. For example, when the conductive band 30L is connected with the conductive trace 22 and the like using solder or a conductive adhesive, cracks may be caused by mechanical stress applied from outside. The electrical connection section 24L is composed of the flexible anisotropic conductive layer 251 to provide flexibility to the electrical connection section 24L. Even if cracks are temporarily caused on the electrical connection section 24L, the cracks are naturally eliminated by the flexible anisotropic conductive layer 251. Thus, even if an external stress is applied, the electrical connection between the conductive band 30L and the conductive trace 22 can be maintained, so that reliability of the guidewire 10L is improved.

Figure 21:
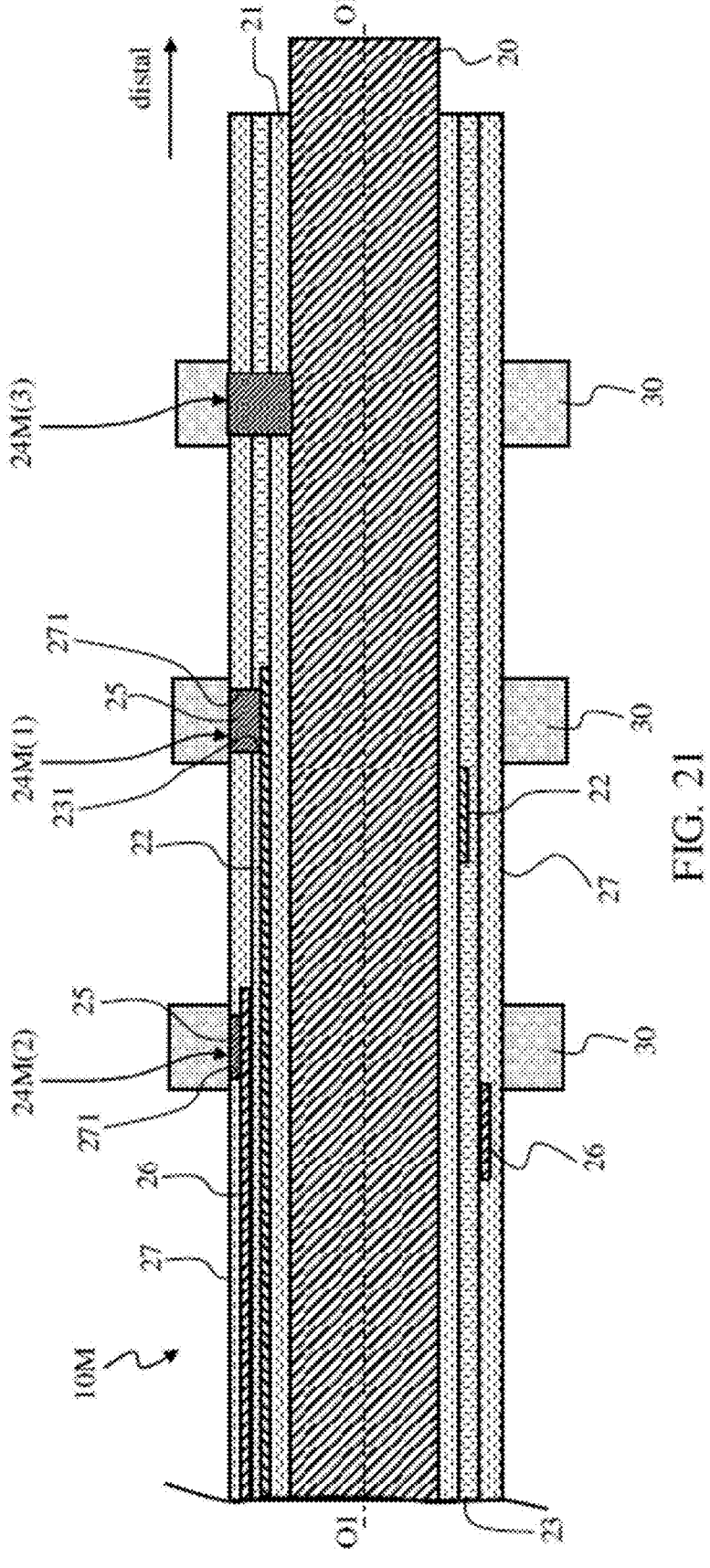
FIG. 21 is a longitudinal sectional view illustrating a distal end side of the guidewire having multiple conductive trace layers.
Figure 22:
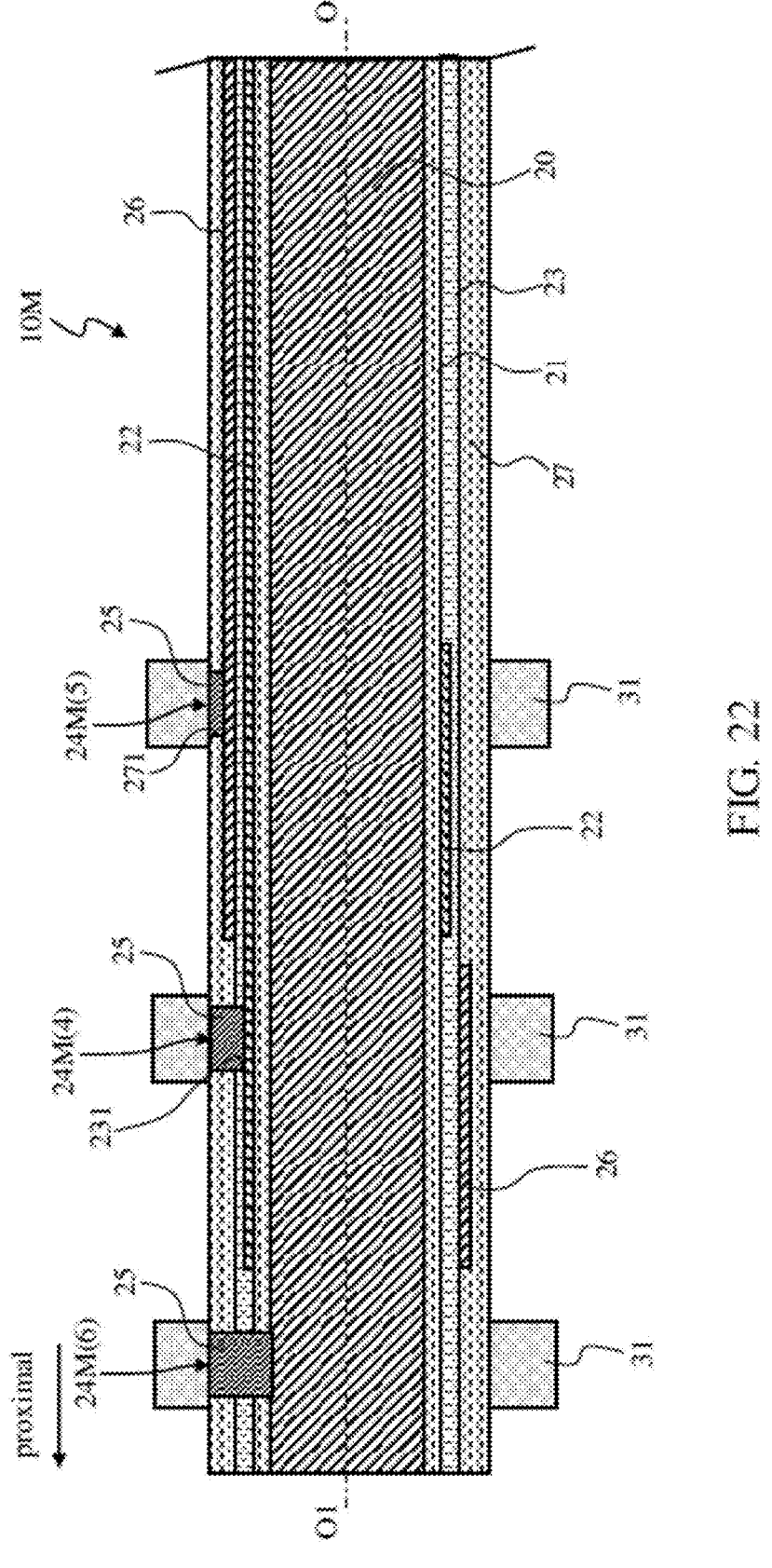
FIG. 22 is a longitudinal sectional view illustrating a proximal end side of the guidewire having multiple conductive trace layers.

FIG. 21 is a longitudinal sectional view illustrating a distal end side of a guidewire 10M having layers of the multiple conductive traces 22 and 26. FIG. 22 is a longitudinal sectional view illustrating a proximal end side of the guidewire 10M having layers of the multiple conductive traces 22 and 26.

In the guidewire 10M, multiple conductive trace layers are formed on the guidewire core 20 in a build-up manner. A first conductive trace layer refers to a conductive layer in which the first conductive traces 22 are formed. A second conductive trace layer refers to a conductive layer in which the second conductive traces 26 are formed. Each of the conductive traces 22 and 26 can also be connected with different sensors (not illustrated) via different printed wiring boards (not illustrated).

The surface of the second conductive trace layer is covered with the third insulating layer 27. The second inner openings 271 are formed at predetermined positions of the third insulating layer 27. An electrical connection section 24M (2) on the second conductive trace layer is composed of the second inner opening 271 and the conductive connection member 25. An electrical connection section 24M (1) on the first conductive trace layer is composed of the first inner opening 231, the second inner opening 271, and the conductive connection member 25. Each of the electrical connection sections 24M (1) and 24M (2) is electrically and mechanically connected to each corresponding conductive band 30 via the conductive connection member 25. As the conductive connection member 25, for example, solder, a conductive adhesive, ACF, ACP, or the like can be used.

Figure 23:
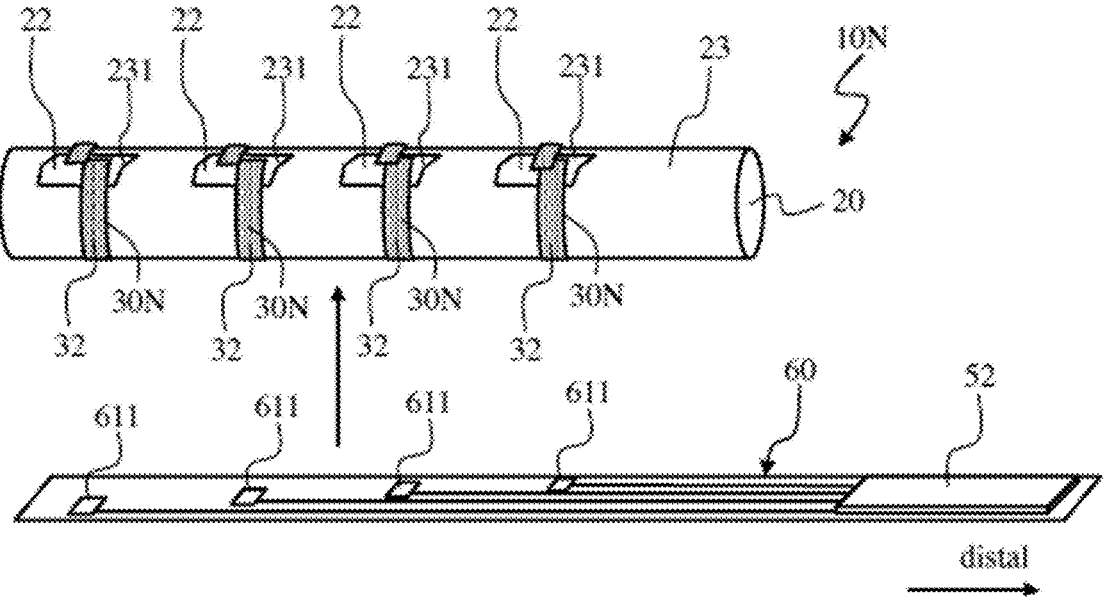
FIG. 23 is a diagram illustrating an example in which a printed wiring board equipped with a sensor is attached to the conductive bands composed of conductive wires.

FIG. 23 illustrates a distal end side of a guidewire 10N before the printed wiring board 60 equipped with the sensor 52 is attached to a conductive band 30N composed of a conductive wire 32. The conductive wire 32 is a fine-diameter wire or ribbon wire made of a conductive metal material such as gold, silver, copper, or a gold alloy. The conductive wire 32 is wound around the guidewire core 20 from above the insulating layer 23 by a so-called wire bonding method and secured to the conductive trace 22 to form the conductive band 30N. That means, the conductive wire 32 is wound around the guidewire core 20 from above the insulating layer 23 at the position of the first inner opening 231, and then the both ends of the conductive wire 32 are bonded and secured to the conductive trace 22 within the first inner opening 231 to obtain the conductive band 30N.

The conductive wire 32 is electrically and mechanically connected to the end 221 (not illustrated in FIG. 23) of the conductive trace 22. The flagged end 221 can be formed as e.g. a metallic multilayer film obtained by plating gold or a nickel-gold alloy on a surface of a copper-plated conductive trace. The conductive wire 32 can be made of gold, a gold alloy, aluminum, or the like. Since gold or gold alloys are electrochemically stable, ion migration between the adjacent conductive bands 30N can be suppressed by forming the conductive wire 32 from gold or a gold alloy.

The sensor 52 is mounted on the distal end side of the printed wiring board 60. On the proximal end side of the printed wiring board 60, multiple pads 611 are disposed in correspondence with the conductive bands 30N. Each of the pads 611 is electrically connected with a terminal (not illustrated) of the sensor 52 via a wiring pattern (not illustrated). Each of the pads 611 is secured to each corresponding conductive band 30N with solder, a conductive adhesive, or the like, so that the conductive traces 22 are electrically connected with the sensor 52.

Figure 24:
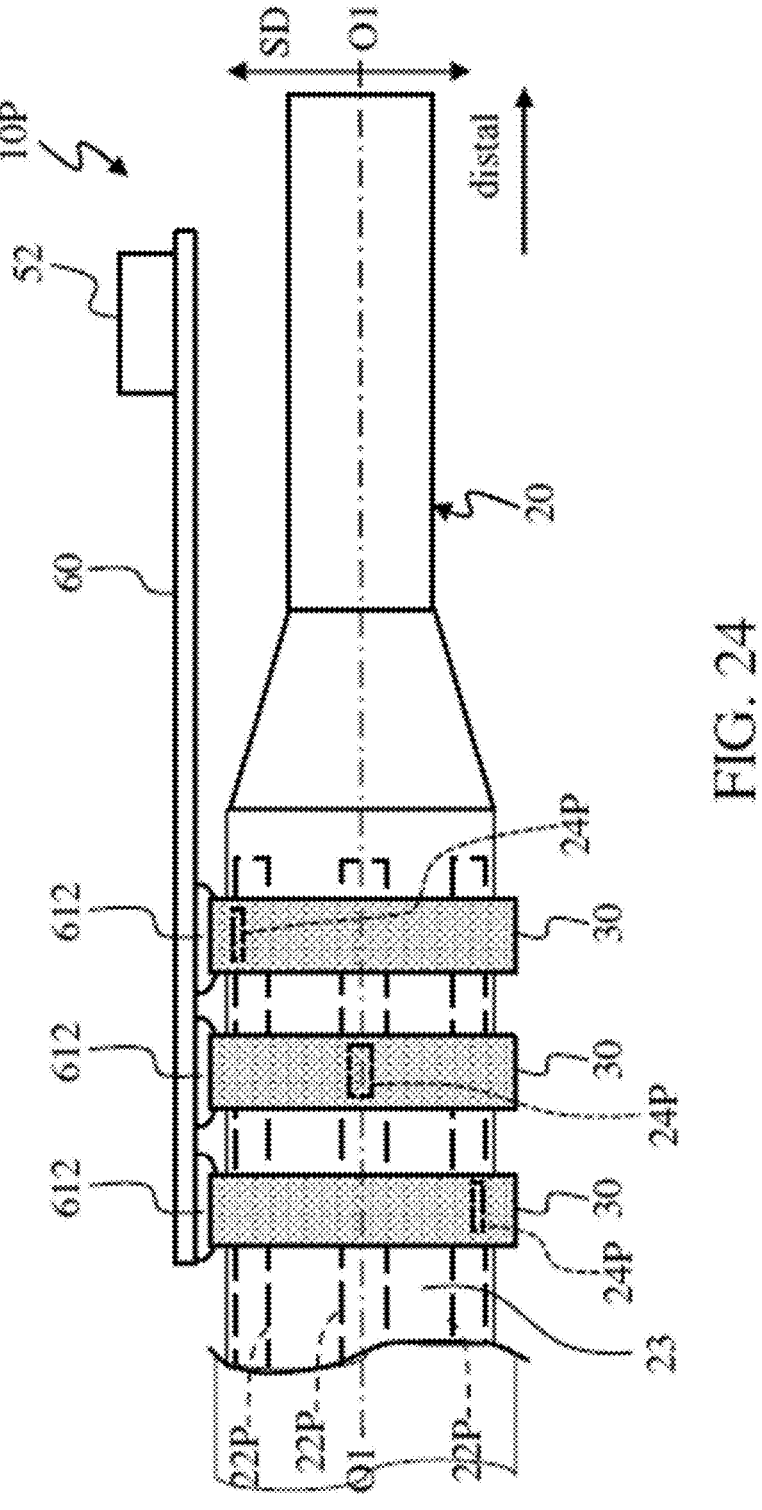
FIG. 24 is a diagram illustrating an example of a structure in which the sensor is attached to a distal end side of the guidewire core.

FIG. 24 illustrates a distal end side of a guidewire 10P. In FIG. 24, the sensor 52 is attached to the distal end side of the guidewire core 20 using the conductive bands 30 and the printed wiring board 60. FIG. 24 is a side view of the guidewire 10P.

Multiple conductive traces 22P are formed spaced apart from each other in the circumferential direction (SD direction or side direction) of the guidewire core 20. Each conductive trace 22P has an electrical connection section 24P. Each conductive trace 22P is electrically connected to the conductive band 30 via the electrical connection section 24P. Positions of the respective electrical connection sections 24P are spaced apart from each other in the circumferential direction of the guidewire core 20 and in the axial O1 direction. Each electrical connection section 24P is electrically connected to each conductive band 30. Thus, the printed wiring board 60 can be electrically connected with the electrical connection sections 24P regardless of the positions of the electrical connection sections 24P. Pads (not illustrated in FIG. 24) of the printed wiring board 60 are electrically and mechanically connected with the conductive bands 30 via the conductive connection members 612 such as solder.

Figure 25:
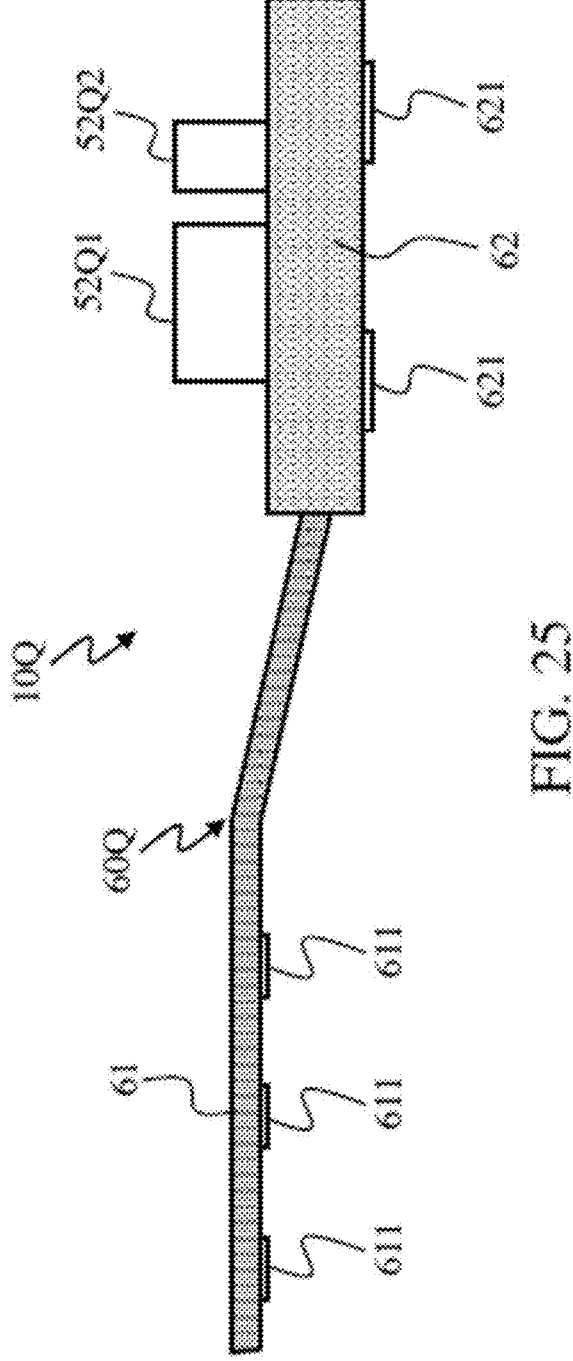
FIG. 25 is a diagram illustrating an example in which a sensor is mounted on a printed wiring board having a flexible substrate member and a rigid substrate member.

FIG. 25 illustrates a sensor portion of a guidewire 10Q, in which the configuration on the guidewire core side is not illustrated. A printed wiring board 60Q has a flexible substrate member 61 and a rigid substrate member 62, and the sensor 52 is mounted on the rigid substrate member 62. The printed wiring board 60Q used for the guidewire 10Q includes the flexible substrate member 61 located on the proximal end side and the rigid substrate member 62 disposed on the distal end side of the flexible substrate member 61. Pads 611 corresponding to the respective conductive bands 30 (not illustrated in FIG. 25) are formed on a face that faces the guidewire core 20 (not illustrated in FIG. 25) among both faces of the flexible substrate member 61. The face that faces the guidewire core 20 refers to a downward face in FIG. 25. Among multiple faces of the rigid substrate member 62, a face that faces the guidewire core 20 has connection sections 621 that are connected to other conductive bands (not illustrated) disposed on the small-diameter section 202 (not illustrated) of the guidewire core 20 (not illustrated).

Figure 26:
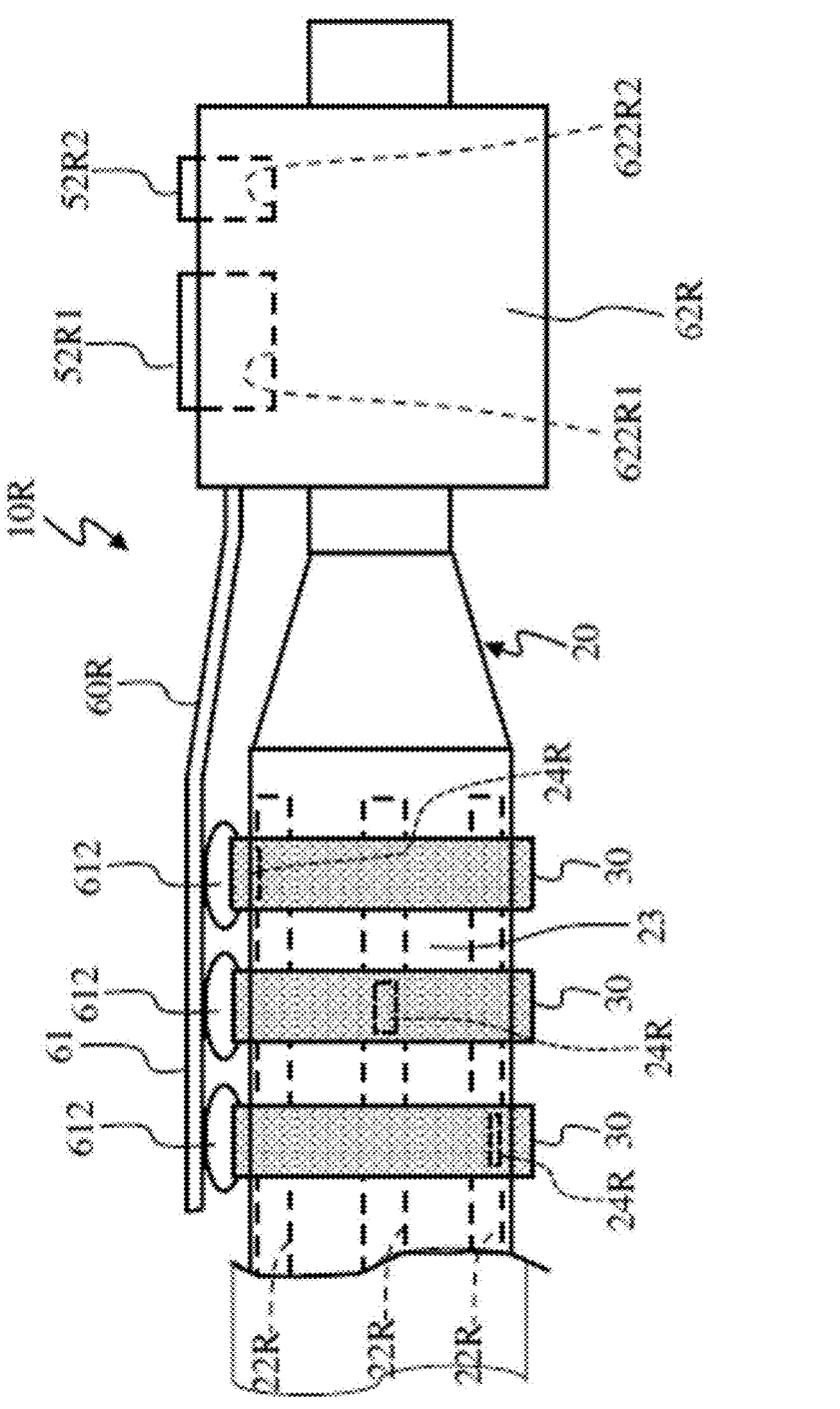
FIG. 26 is a diagram illustrating an example in which an accommodation section for accommodating the sensor is disposed on the rigid substrate member.

FIG. 26 illustrates an example in which multiple sensors 52R1 and 52R2 are accommodated in a rigid substrate member 62R. A printed wiring board 60R used in a guidewire 10R includes the flexible substrate member 61 and the rigid substrate member 62R. The rigid substrate member 62R has multiple sensor accommodation sections 622R1 and 622R2. The sensors 52R1 and 52R2 are attached to the sensor accommodation sections 622R1 and 622R2 respectively. The rigid substrate member 62R having the sensor accommodation sections 622R1 and 622R2 achieves functions as a sensor housing. FIG. 26 illustrates an example of accommodating the multiple sensors 52R1 and 52R2 in the rigid substrate member 62R, but instead, either the sensor 52R1 or the sensor 52R2 may be accommodated in the rigid substrate member 62R. Three or more sensors may be accommodated in the rigid substrate member 62R. The sensors and electronic components other than the sensors may be accommodated in the rigid substrate member 62R. Examples of the electronic components other than the sensors include a signal processing circuit, a transmitting/receiving circuit, and the like. Each of first conductive traces 22R is electrically connected to each corresponding conductive band 30 via electrical connection sections 24R.

Figure 27:
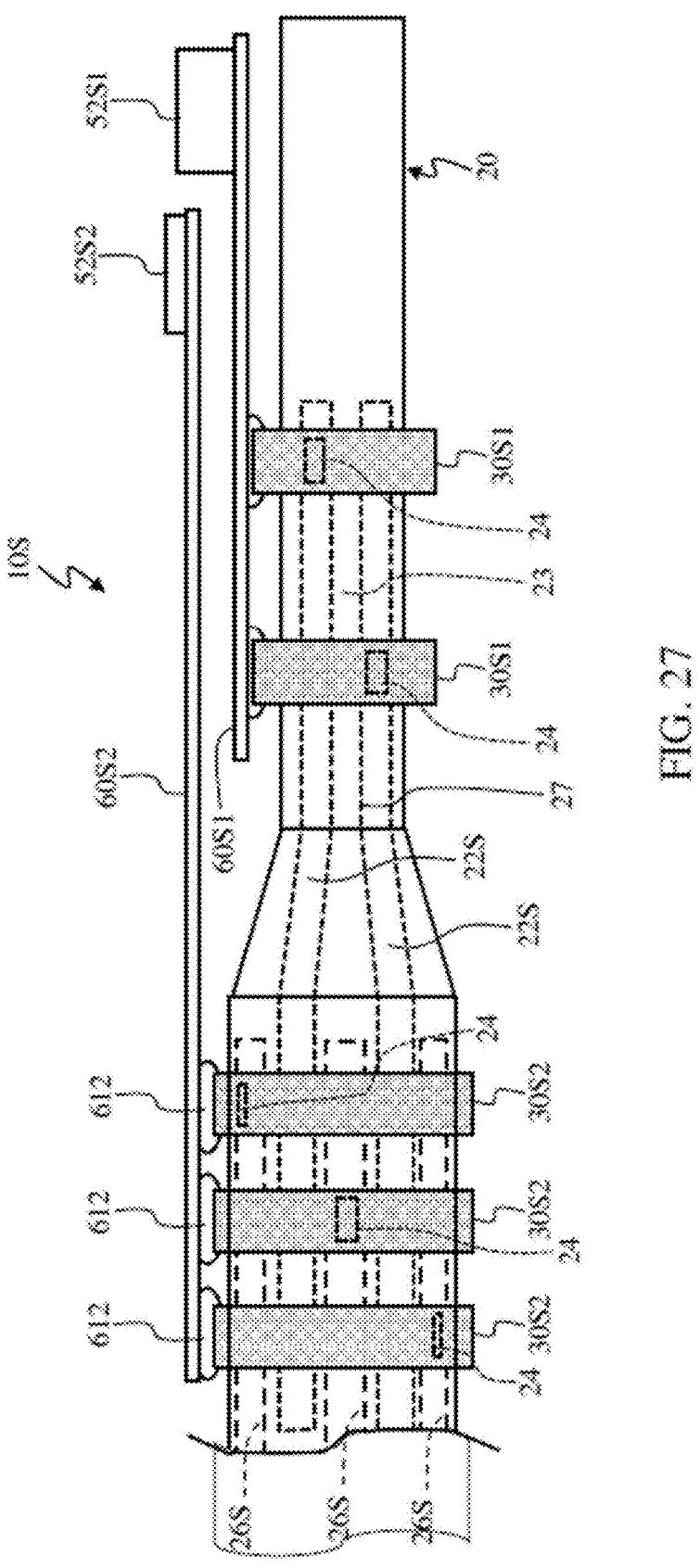
FIG. 27 is a diagram illustrating an example in which the conductive bands are arranged in correspondence with each conductive trace layer.

FIG. 27 illustrates an example in which conductive bands 30S1 and 30S2 are arranged in correspondence with each layer of conductive traces 22S and 26S. FIG. 27 illustrates a distal end side of a guidewire 10S. The multiple first conductive traces 22S are formed extending to the distal end side of the guidewire core 20. Each first conductive trace 22S is electrically connected to a first printed wiring board 60S1 via the conductive bands 30S1. A first sensor 52S1 is mounted on the first printed wiring board 60S1.

Figure 28:
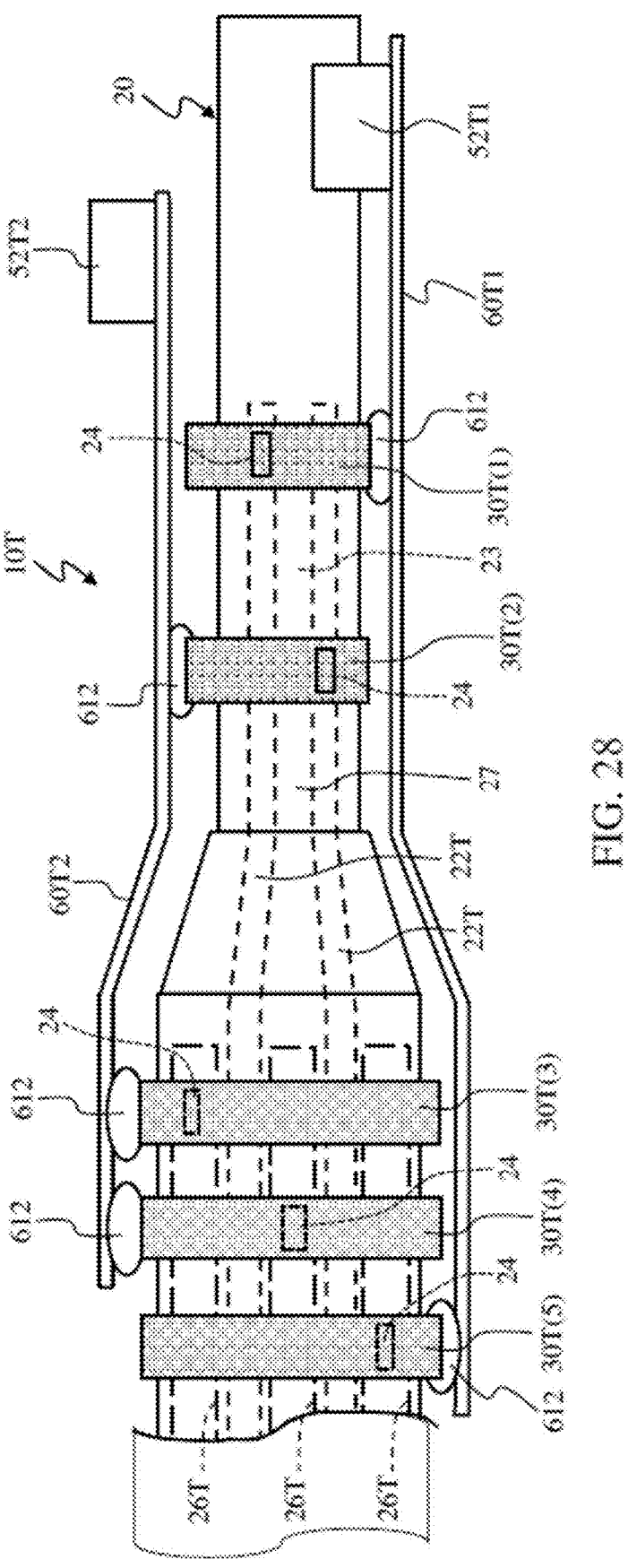
FIG. 28 is a diagram illustrating an example in which each conductive band is electrically connected with the conductive trace of each layer.

Each of the second conductive trace 26S disposed outside the first conductive trace 22S is formed such that a distal end of the second conductive trace 26S extends to a position on a more proximal end side than the distal end side of the first conductive trace 22S. Each second conductive trace 26S is electrically connected to a second printed wiring board 60S2 via the conductive band 30S2. A second sensor 52S2 is mounted on the second printed wiring board 60S2. In this way, the printed wiring boards can be connected to each conductive trace layer via conductive bands FIG. 28 illustrates an example of a guidewire 10T in which one printed wiring board is connected to multiple conductive traces. A printed wiring board 60T1 is electrically connected to a first conductive trace 22T via a conductive band 30T (1) and also electrically connected to a second conductive trace 26T via a conductive band 30T (5). Although not illustrated, a wiring pattern to be connected to the first conductive traces 22T and a wiring pattern to be connected to the second conductive traces 26T are formed on the first printed wiring board 60T1.

A second printed wiring board 60T2 is electrically connected to the first conductive trace 22T via a conductive band 30T (2) and also electrically connected to the multiple second conductive traces 26T via conductive bands 30T (3) and 30T (4). Although not illustrated, a wiring pattern to be connected to the first conductive traces 22T and a wiring pattern to be connected to the second conductive traces 26T are formed on the second printed wiring board 60T2.

Figure 29:
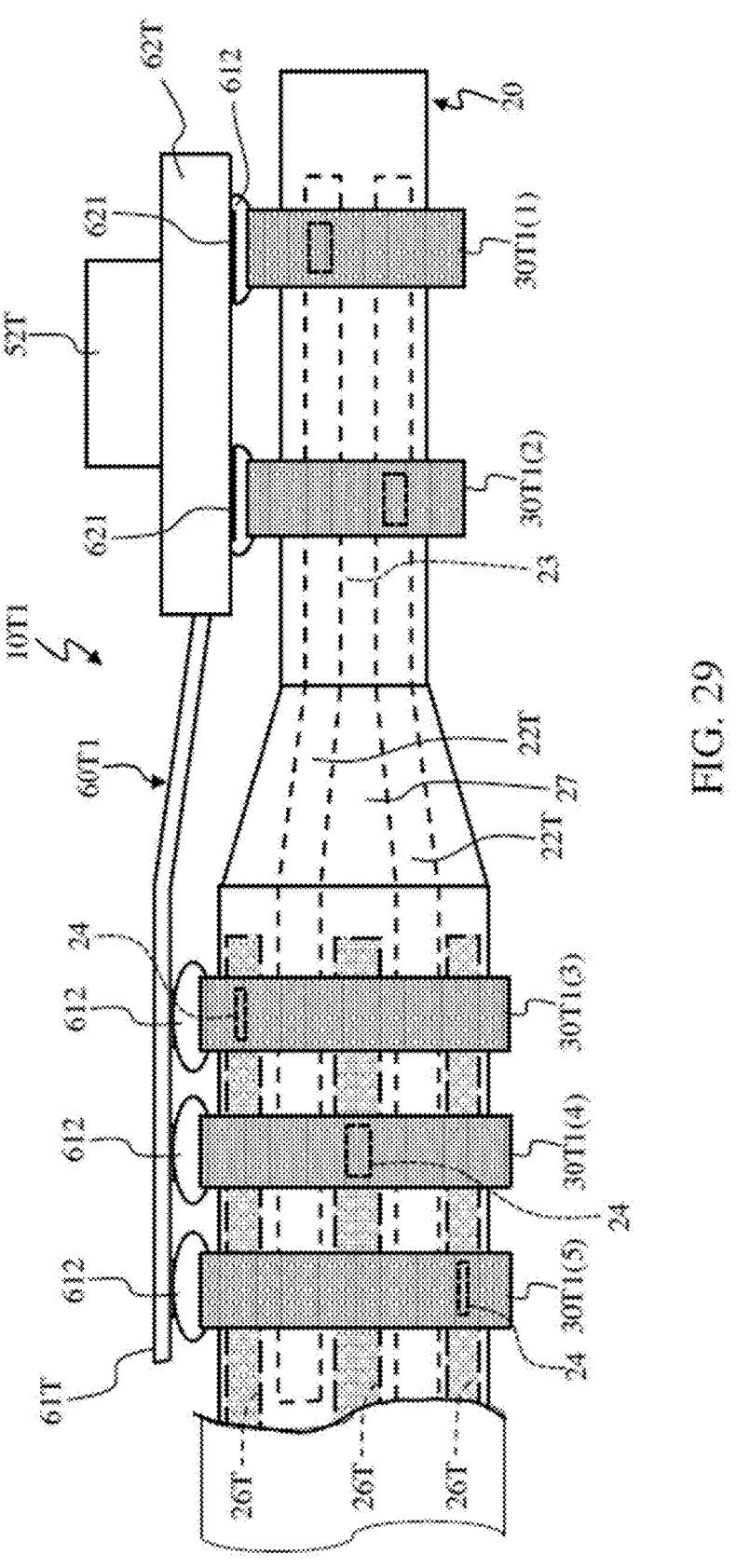
FIG. 29 is a diagram illustrating an example of using a flexible substrate including a flexible substrate member and a rigid substrate member in a case where the conductive bands correspond to each conductive trace layer.

FIG. 29 illustrates an example using a flexible substrate including a flexible substrate member and a rigid substrate member in a case where the conductive bands correspond to each conductive trace layer. A printed wiring board 60T1 used in a guidewire 10T1 includes a flexible substrate member 61T and a rigid substrate member 62T. The flexible substrate member 61T is electrically connected to the multiple second conductive traces 26T via conductive bands 30T1 (3), 30T1 (4), and 30T1 (5). The rigid substrate member 62T is electrically connected to the multiple first conductive traces 22T via conductive bands 30T1 (1) and 30T1 (2).

Multiple wiring patterns (not illustrated) are formed inside the rigid substrate member 62T, and the first conductive trace 22T is electrically connected to a sensor 52T via the wiring patterns. The multiple wiring patterns (not illustrated) are also formed inside the flexible substrate member 61T, and the second conductive trace 26T is electrically connected with the sensor 52T via the wiring patterns.

Figure 30:
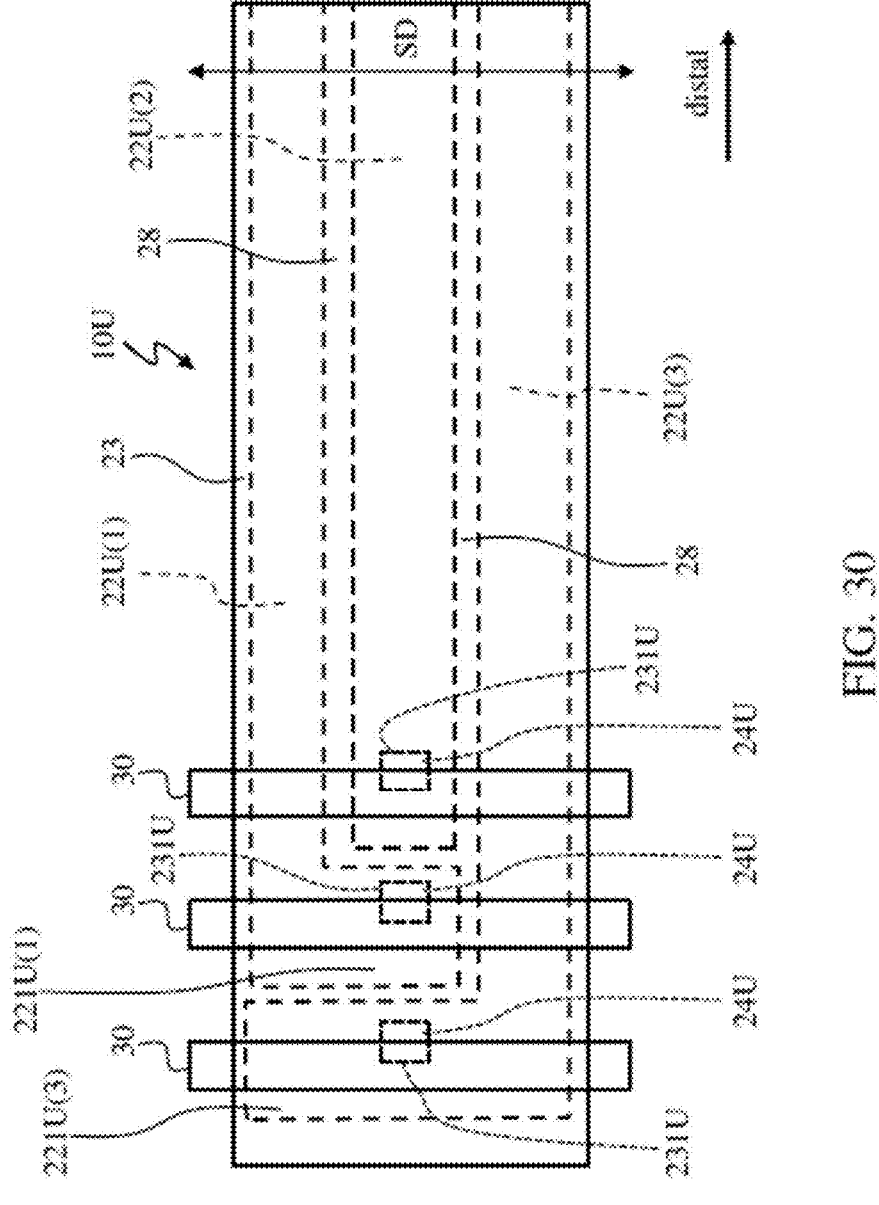
FIG. 30 is a diagram illustrating an example of an arrangement relation between the conductive bands, the conductive traces, and the electrical connection sections.

Arrangement examples of conductive traces, electrical connection sections, and conductive bands (that may also be ring electrodes) on the proximal end side of the guidewire will be explained with reference to FIG. 30 to FIG. 32. In a guidewire 10U illustrated in FIG. 30, conductive traces 22U (1) and 22U (3) are arranged such that a conductive trace 22U (2) located in the center of the circumferential direction (SD direction) of the guidewire core 20 (not illustrated) is sandwiched therebetween from the both sides in the circumferential direction. An end 221U (1) of the conductive trace 22U (1) and an end 221U (3) of the conductive trace 22U (3) are formed so as to bend at almost right angle toward the center in the circumferential direction of the guidewire core 20 such that the ends 221U (1) and 221U (3) are located on the more proximal end side of the guidewire core 20 than a proximal end of the conductive trace 22U (2).

Each conductive band 30 is attached to the surface of the second insulating layer 23 on the guidewire core so as to cover a portion of each corresponding electrical connection section 24U. That means, a portion of a first inner opening 231U of each electrical connection section 24U is exposed and is not hidden by the conductive band 30.

Figure 31:
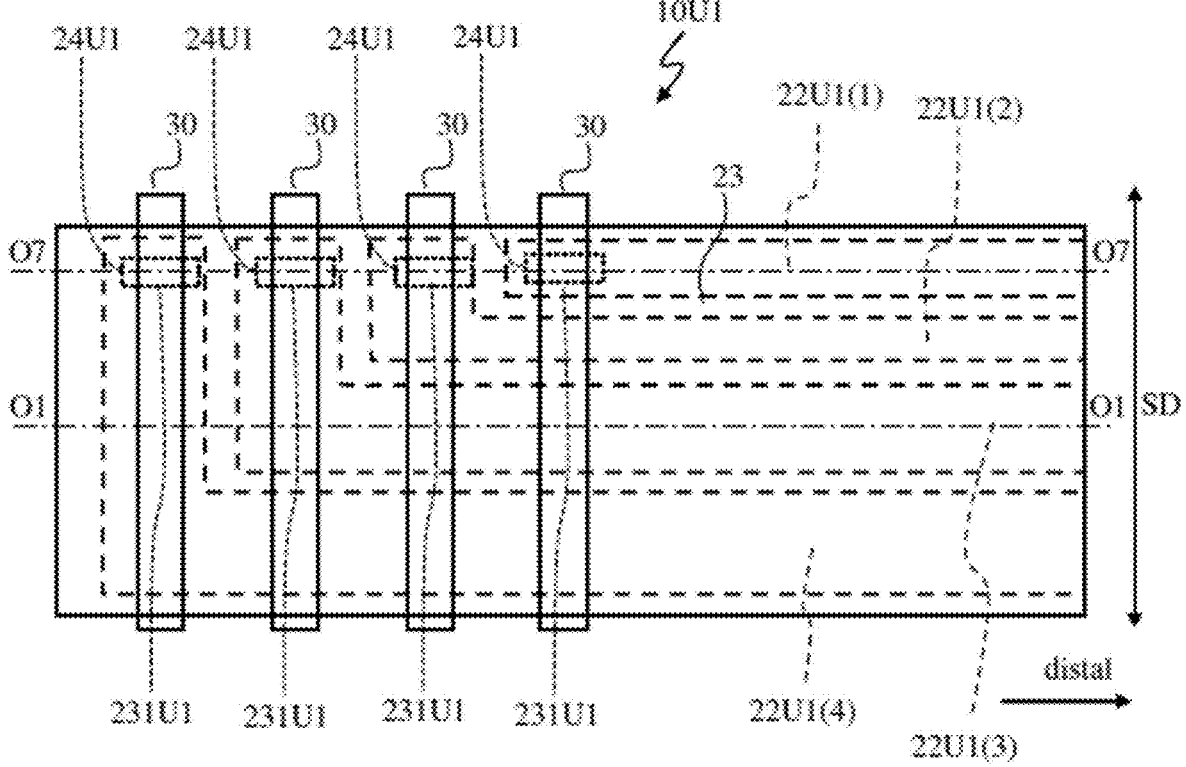
FIG. 31 is a diagram illustrating another example of an arrangement relation between the conductive bands, the conductive traces, and the electrical connection sections.

In a guidewire 10U1 illustrated in FIG. 31, respective electrical connection sections 24U1 are aligned in a straight line O7. The straight line O7 is parallel to the longitudinal axis O1 of the guidewire 20. Both width-direction end sides of the first inner opening section 231U1 of each electrical connection section 24U1 are exposed from the conductive band 30. The width direction of the first inner opening section 231U1 refers to the axis O1 direction.

A width direction of the first inner opening section 231U1 is set to be longer than the width dimension of the conductive band 30. The conductive band 30 is attached onto the second insulating layer that covers the guidewire core 20 (both not illustrated) such that the center of the conductive band 30 substantially coincides with the width-direction center of the first inner opening section 231U1. Accordingly, the both end sides of the first inner opening section 231U1 protrude from the conductive band 30. Conductive traces 22U1 (1) to 22U1 (4) are electrically connected to the conductive bands 30 via each corresponding electrical connection section 24U1.

Figure 32:
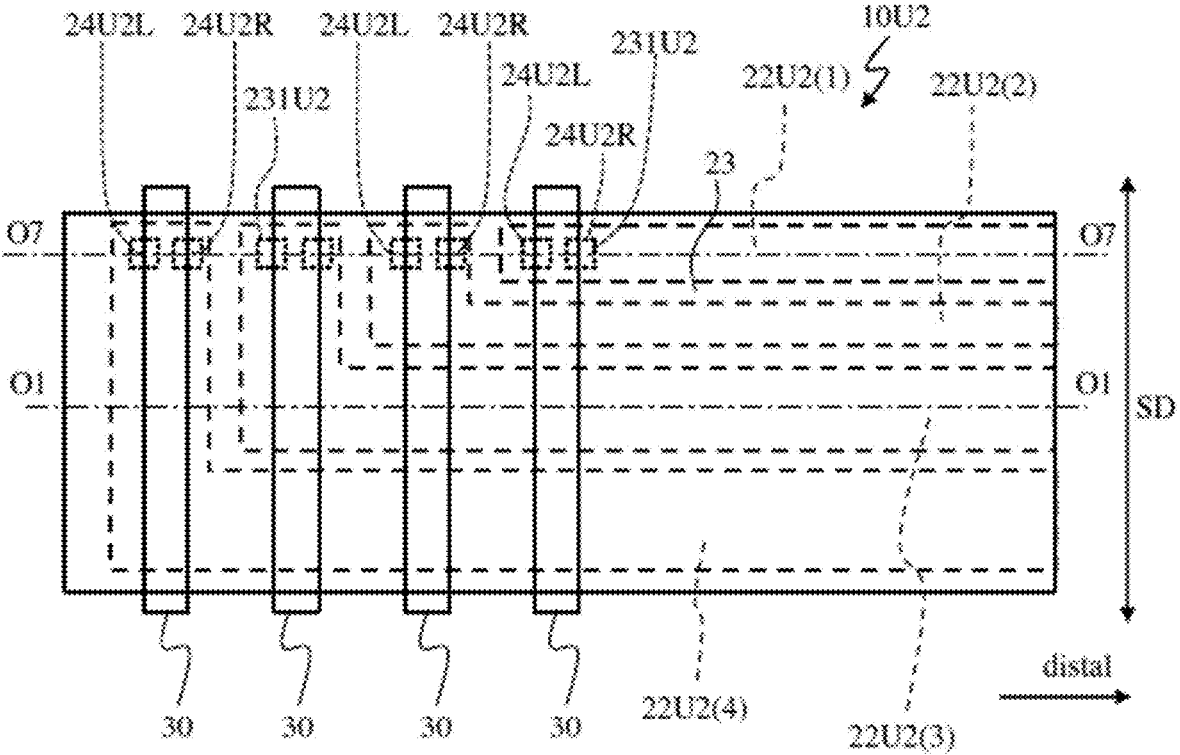
FIG. 32 is a diagram illustrating even another example of an arrangement relation between the conductive bands, the conductive traces, and the electrical connection sections.

In a guidewire 10U2 illustrated in FIG. 32, each of electrical connection sections 24U2L and 24U2R is disposed on each of both width-direction sides of each conductive band 30. The electrical connection section 24U2L on the proximal end side is exposed from the proximal-side end of the both width-direction ends of the conductive band 30. The electrical connection section 24U2R on the distal end side is exposed from the distal-side end of the both width-direction ends of the conductive band 30. That means, each conductive band 30 is attached onto the second insulating layer covering the guidewire core 20 (both not illustrated) such that the corresponding electrical connection sections 24U2L and 24U2R partially protrude. Conductive traces 22U2 (1) to 22U2 (4) are electrically connected to the conductive bands 30 via the corresponding electrical connection sections 24U2L and 24U2R.

Figure 33:
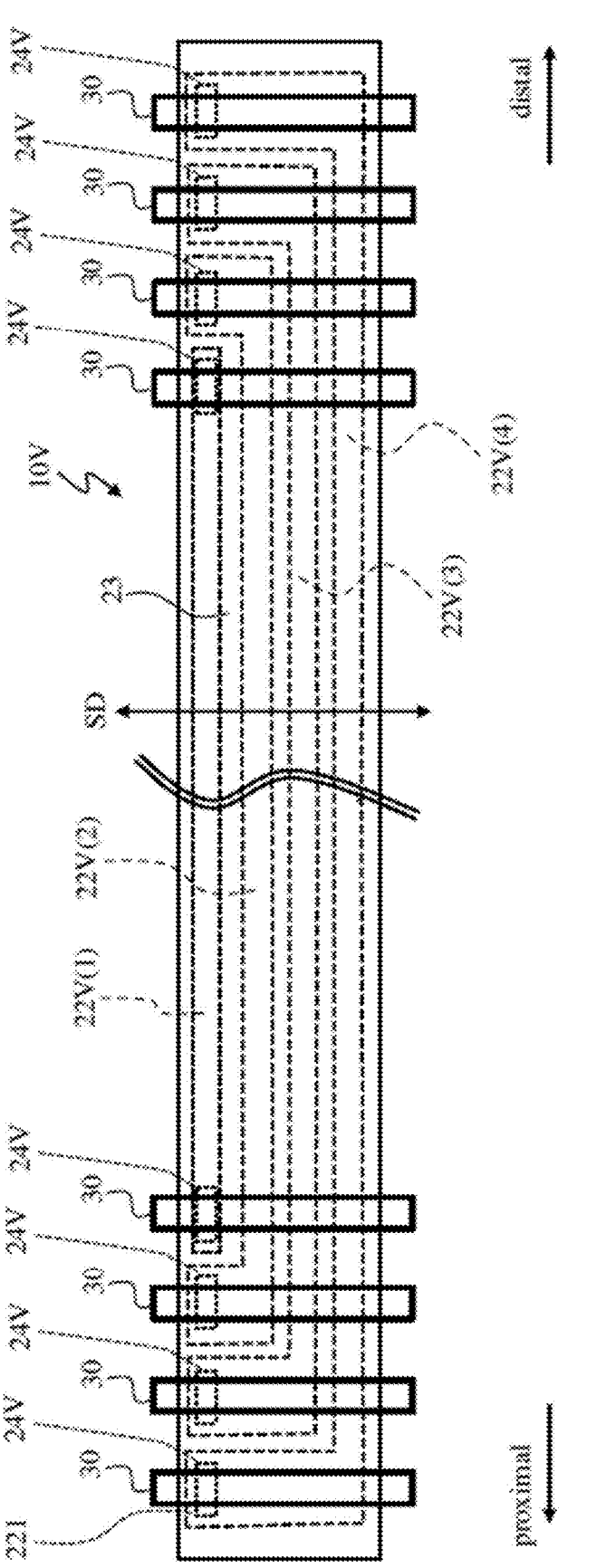
FIG. 33 is a diagram illustrating an example in which the respective conductive traces having different lengths are arranged.

FIG. 33 illustrates an arrangement example of conductive traces 22V. In a guidewire 10y, multiple first conductive traces 22V(1) to 22V(4) are formed spaced apart from each other in the circumferential direction (SD direction). The first conductive trace 22V (1) is the shortest and the first conductive trace 22V (2) is longer than the first conductive trace 22V (1). The first conductive trace 22V (3) is longer than the first conductive trace 22V (2). The first conductive trace 22V (4) is the longest. As illustrated in FIG. 33, the first conductive traces 22V (1) to 22V (4) can be different from each other in length. Electrical connection sections 24V are disposed on both end sides of each of the first conductive traces 22V (1) to 22V (4).

Figure 34:
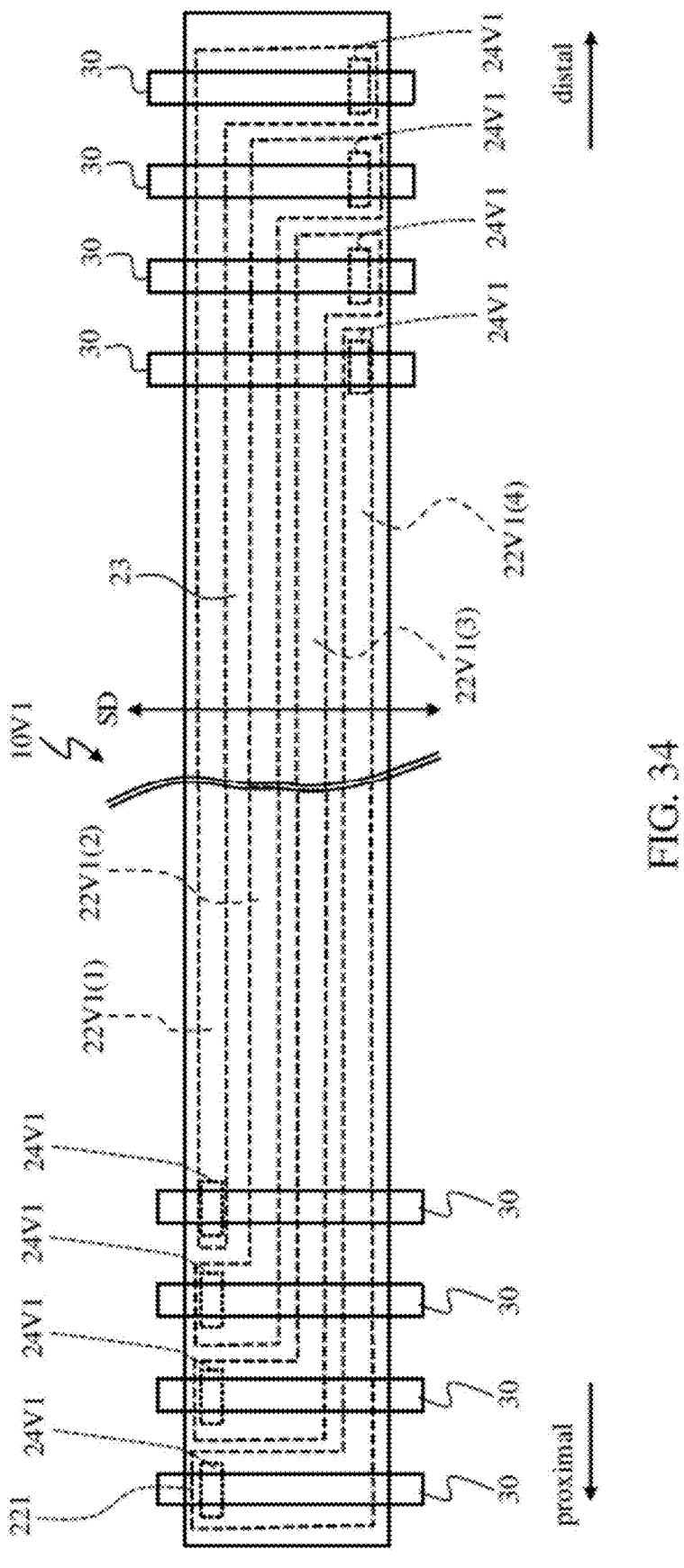
FIG. 34 is a diagram illustrating an example in which pairs of the conductive traces having same lengths are arranged.

FIG. 34 illustrates an example in which multiple first conductive traces 22V1 (1) to 22V (4) include at least one group consisting of the first conductive traces having same lengths. FIG. 34 illustrates a guidewire 10V1 including a first group consisting of the first conductive traces 22V1 (1) and 22V1 (4) and a second group consisting of the first conductive traces 22V1 (2) and 22V1 (3). Each of the first and second groups consists of the conductive traces having same wiring lengths, which can also be referred to as an isometric wiring pair. The pair consisting of the conductive traces having same wiring lengths can be used e.g. as wiring for differential signals.

The first conductive traces 22V1 (1) and 22V1 (4) constituting the first group are a point-symmetrical pair. Also, the first conductive traces 22V1 (2) and 22V1 (3) constituting the second group are a point-symmetrical pair. That means, when one first conductive trace belonging to one group is turned 180 degrees around its centroid, the first conductive trace overlaps with the other first trace belonging to the same group. Thus, the lengths of the first conductive traces belonging to the same group are equal.

An electrical connection section 24V1 is disposed on both end sides of each of the first conductive traces 22V1 (1) to 22V1 (4). Each of the first conductive traces 22V1 (1) to 22V1 (4) is electrically connected to the conductive band 30 via each corresponding electrical connection section 24V1.

Figure 35:
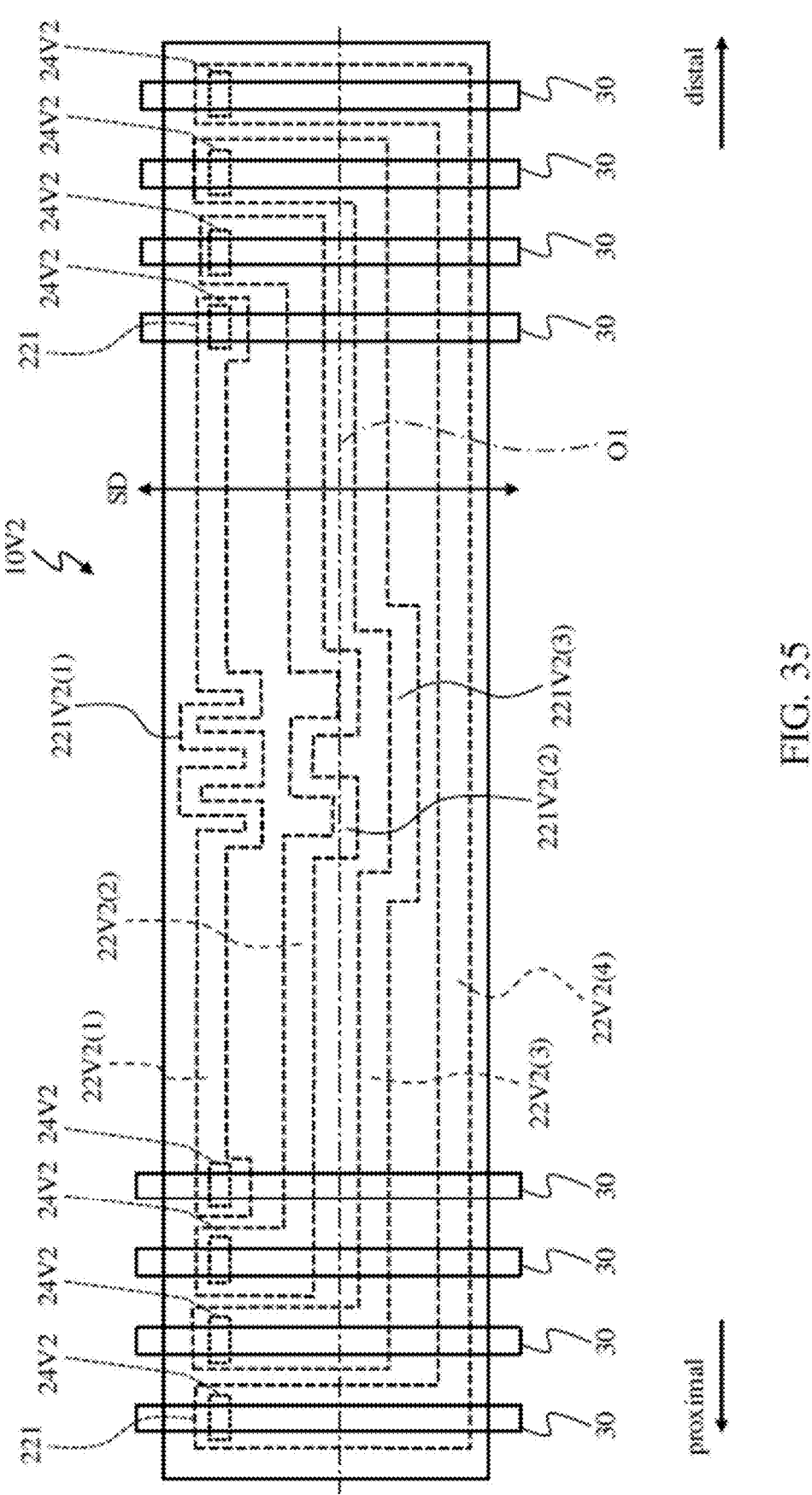
FIG. 35 is a diagram illustrating another example in which pairs of the conductive traces having same lengths are disposed.

FIG. 35 illustrates an example in which at least one conductive trace of the first conductive traces belonging to the same group has a meandering section 221V so as to have the same length as those of the other conductive traces. In a guidewire 10V2 of FIG. 35, multiple first conductive traces 22V2 (1) to 22V2 (4) have same lengths and belong to the same group. An electrical connection section 24V2 is disposed on both end sides of each of the conductive traces 22V2 (1) to 22V2 (4).

The both ends of the first conductive trace 22V2 (1) are located on the innermost side in the axis O1 direction compared to the both ends of the other first conductive traces 22V2 (2) to 22V2 (4), and the both ends of the first conductive trace 22V2 (2) are located outside of the first conductive trace 22V2 (1) in the axis O1 direction. The both ends of the first conductive trace 22V2 (3) are located outside of the first conductive trace 22V2 (2) in the axis O1 direction. The both ends of the first conductive trace 22V2 (4) are located outside of the first conductive trace 22V2 (3) in the axis O1 direction. Thus, if the middle of each of the conductive traces 22V2 (1) to 22V2 (4) illustrated in FIG. 35 is simply rectangular, the arrangement of the conductive traces is the same as the example described in FIG. 33.

However, a portion of the multiple first conductive traces illustrated in FIG. 35 includes a meandering section 221V2. That means, the first conductive traces 22V2 (1) to 22V2 (3) of the multiple first conductive traces have meandering sections 221V2 (1) to 221V2 (3) respectively, on an almost middle portion in the length direction thereof. The meandering section 221V2 can also be referred to as a meander wiring. The first conductive trace 22V2 (4) does not have the meandering section 221V2 because both ends of the trace are located on the outermost sides in the axis O1 direction. The other first conductive traces 22V2 (1) to 22V2 (3) whose both ends are located inside the both ends of the first conductive trace 22V2 (4) include the meandering sections 221V2 (1) to 221V2 (3) respectively, so as to have the same length as of the first conductive trace 22V2 (4) having no meandering section.

All of the first conductive traces 22V2 (1) to 22V2 (4) may have the meandering sections 221V2 such that all of the first conductive traces 22V2 (1) to 22V2 (4) have the same length. Although FIG. 35 illustrates the meandering sections

221V2 bending at right angle, the meandering sections 221V2 can also be formed so as to curve smoothly.

Figure 36:
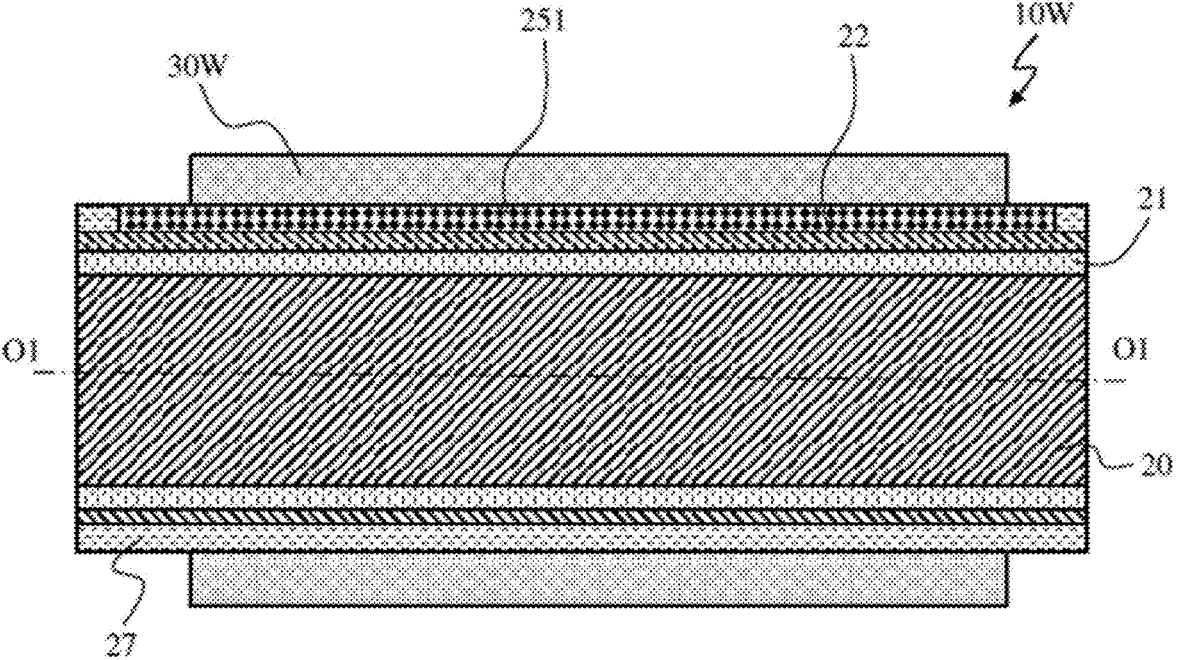
FIG. 36 is a diagram illustrating an example in which the conductive band is electrically connected with the conductive trace using an anisotropic conductive elastomer as the anisotropic conductive material.

In a guidewire 10W of FIG. 36, the first conductive trace 22 is connected with a conductive band 30W via the anisotropic conductive material layer 251. The anisotropic conductive material is e.g. ACR. A material other than ACR may be used. For example, the anisotropic conductive material layer 251 is arranged so as to cover the whole surface of the end 221 (flag section) having a relatively large area in the first conductive trace 22.

Figure 37:
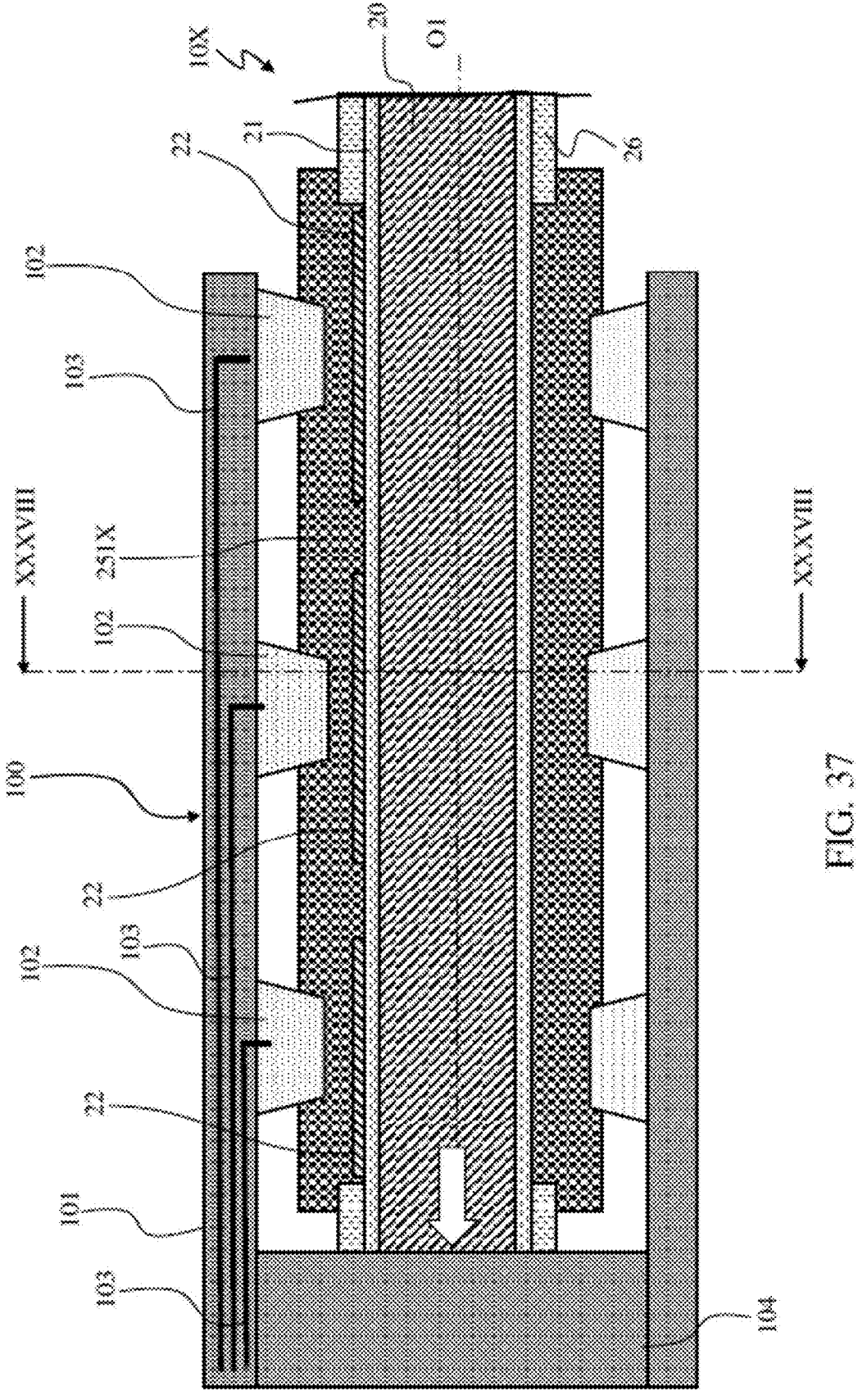
FIG. 37 is a diagram illustrating an example in which the anisotropic conductive elastomer as the anisotropic conductive material is used for a member having functions of both the conductive band and the electrical connection section.

Examples in which an anisotropic conductive material layer 251X is used instead of the electrical connection section and the conductive band will be explained with reference to FIG. 37 to FIG. 39. For example, ACR is used as the anisotropic conductive material. FIG. 37 illustrates a proximal end side of a guidewire 10X. When using the guidewire 10X, the proximal end side of the guidewire 10X is attached to a connector member 100. The connector member 100 is a member for electrically connecting an external apparatus (not illustrated) such as a measuring device or a controller with the guidewire 10X. The connector member 100 includes a bottom section 104, a clip section 101 rotatably attached to the bottom section 104, multiple pressing pins 102 that protrudes from an inner face side of the clip section 101, and wiring 103 connected to each of the pressing pins 102. Each pressing pin 102 is arranged in correspondence with each conductive trace 22.

The proximal end of the guidewire 10X is inserted into the connector member 100 so as to abut on the bottom section 104 of the connector member 100. Then, the clip section 101 pinches the guidewire 10X, so that the pressing pins 102 disposed on the inner face side of the clip section 101 press predetermined positions of the anisotropic conductive material layer 251X. When the anisotropic conductive layer 251X is pressed in the radial direction by the pressing pins 102, conductive paths connecting from the pressing pins 102 to the conductive traces 22 are formed. Thereby, a sensor (not illustrated) on the distal end side of the guidewire 10X is electrically connected with an external apparatus via the conductive traces 22 and the connector member 100.

Figure 38:
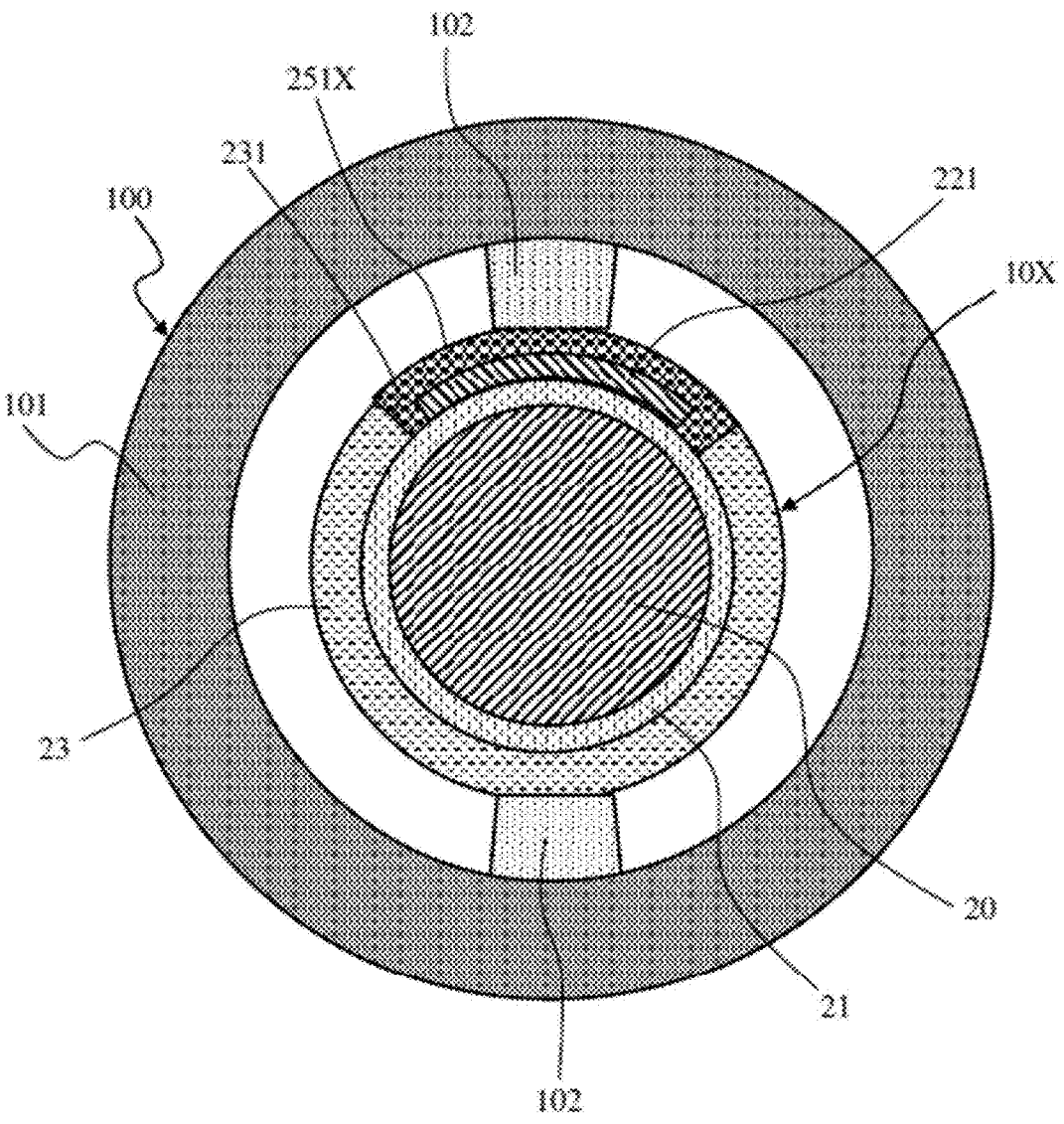
FIG. 38 is a sectional view that is viewed from the arrow XXXVIII-XXXVIII direction in FIG. 37.

FIG. 38 is a sectional view that is viewed from the XXXVIII direction indicated in FIG. 37. The anisotropic conductive material layer 251X is arranged so as to fill the inside of the first inner opening 231 formed on the second insulating layer 23 in correspondence with the end 221 of the first conductive trace 22. In FIG. 38, the wiring 103 is not illustrated.

Figure 39:
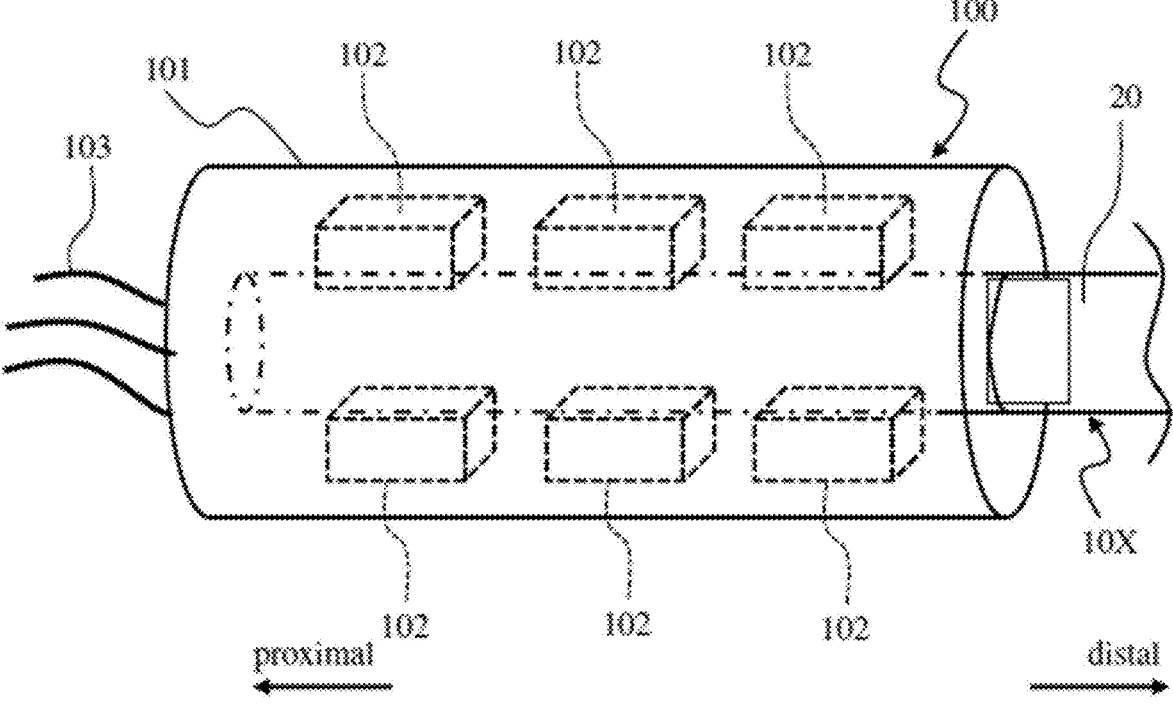
FIG. 39 is an explanatory diagram schematically illustrating a connector member for electrically connecting the guidewire with an external apparatus.

FIG. 39 is a schematic perspective view of the connector member 100.

Multiple approaches to incorporating multiple conductors on a guidewire by building the multiple conductor traces of variable sizes and material compositions on separate insulating layers are described. The approaches described in the invention facilitate ease of assembly of sensors to the guidewire or catheter element. This approach is particularly useful in scenarios where electrical or mechanical properties of the device need to be altered in specific sections to either enhance device performance and reliability (e.g. selective abrasion resistance), or facilitate ease of assembly (e.g. soldering or connection ease), or in some instances achieve desired electrical characteristics (e.g. impedance). The desired properties are incorporated into the same device requiring an innovative approach to forming signal wires in an otherwise tight space without impacting the primary mechanical performance of the devices.

Incorporating conductive elements on a core wire of a typical 0.014" guidewire without impacting its desired mechanical properties such a trackability, torque response etc. maybe challenging. Using a layered manufacturing approach such as the one described in a patent application 63/090,487 (incorporated here) it is possible to form conductive elements directly on a core to retain the basic mechanical performance of the guidewire device. However, incorporating a larger number of conductive elements, for example more than 4, on a core wire of a typical 0.014" or smaller guidewire diameter can be very challenging. When there is a need to incorporate more than one type of sensors on the same device or incorporate sensors that need more than four discrete communicating channels, it may be beneficial to have more than four disparate signal carrying elements on the same device. This can be achieved by using a layered approach described below. Note that the present disclosure is applied not only to the 0.014" guidewire core 20 but also to another guidewire 10 having a typical diameter dimension.

Figure 40A:
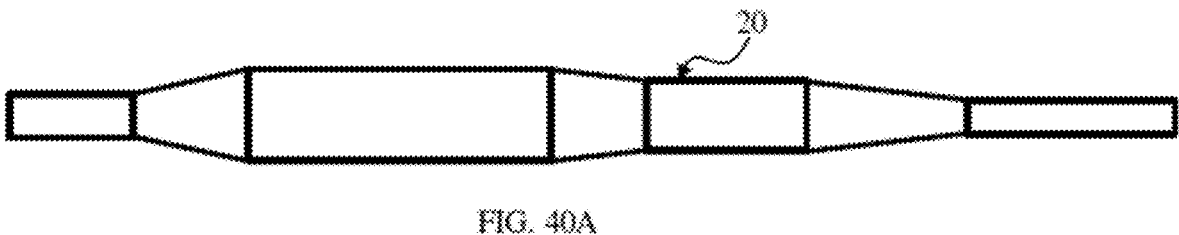
FIG. 40A is a plan view of the guidewire core.

The typical guidewire core 20 is illustrated in FIG. 40A. It has multiple diameters and tapers with the diameters at the distal end of the device typically being smaller than other sections of the device. The core material is typically Stainless Steel (SS) or Nitinol or a combination.

Figure 40B:
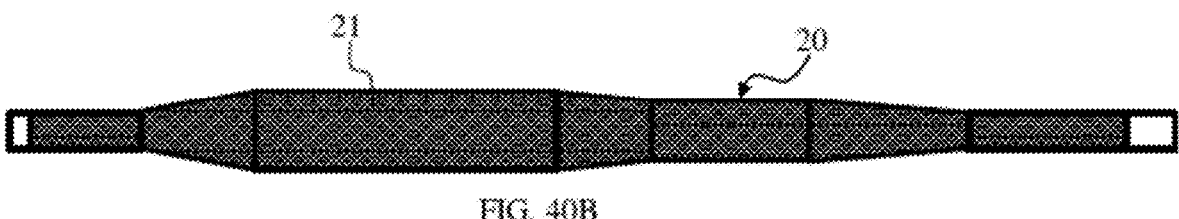
FIG. 40B is a plan view of the guidewire core having a first insulating layer formed on the surface.

The insulating layer 21 is created on the metallic core 20, as illustrated in FIG. 40B. The insulating layer 21 can be formed using various methods such as a dip coating, spray coating, Physical Vapor Deposition (PVD), Chemical Vapor Deposition (CVD), printing, melt reflow etc. The polymer can be polyimide, PET, Nylon, Pebax etc.

Figure 40C:
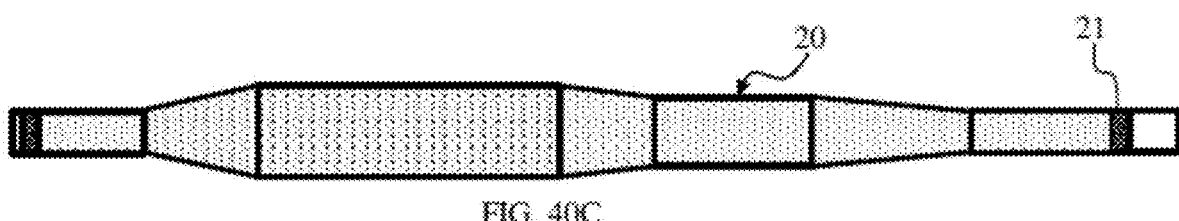
FIG. 40C is a plan view of the guidewire core in which a conductive layer is formed on the surface of the first insulating layer.

A conductive layer is then deposited on the insulating layer 21, as illustrated in FIG. 40C. One approach is to first apply a conductive layer such as palladium or silver as a seed and then to use electroless plating or electroplating, to apply a layer of copper, gold or other highly conductive metal.

The conductive layer is then processed to form the individual electrically isolated conductive elements 22 by selectively etching the conductor. One approach to achieve this is by using a laser to ablate the conductor away to form individual traces.

Often times a substrate on which the conductive elements need to be incorporated do not have a constant dimensional profile. For e.g. a typical core of a coronary guidewire is ground such that the distal end tapers down to smaller OD so that stiffness of the device is reduced and the distal end is more trackable and atraumatic as it traverses the blood vessels. Prior art describes embedding (U.S. Ser. No. 10/791,991 B1) a conductive element such as a flat wire ribbon into a polymeric insulating layer. This approach has limitations as it is difficult to vary the conductor profile over the entire device length (which can vary from 180 cm to 300 cm).

Figure 41:
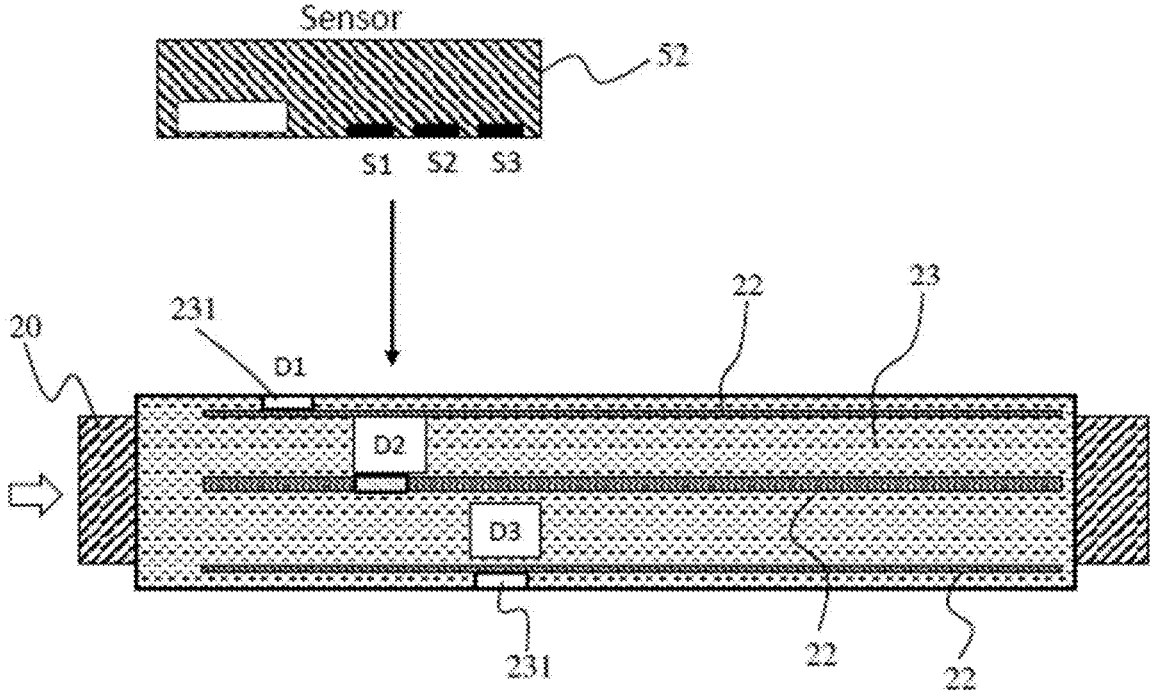
FIG. 41 is a diagram illustrating an example of a method for connecting a pad of the sensor with the electrical connection section.
Figure 42:
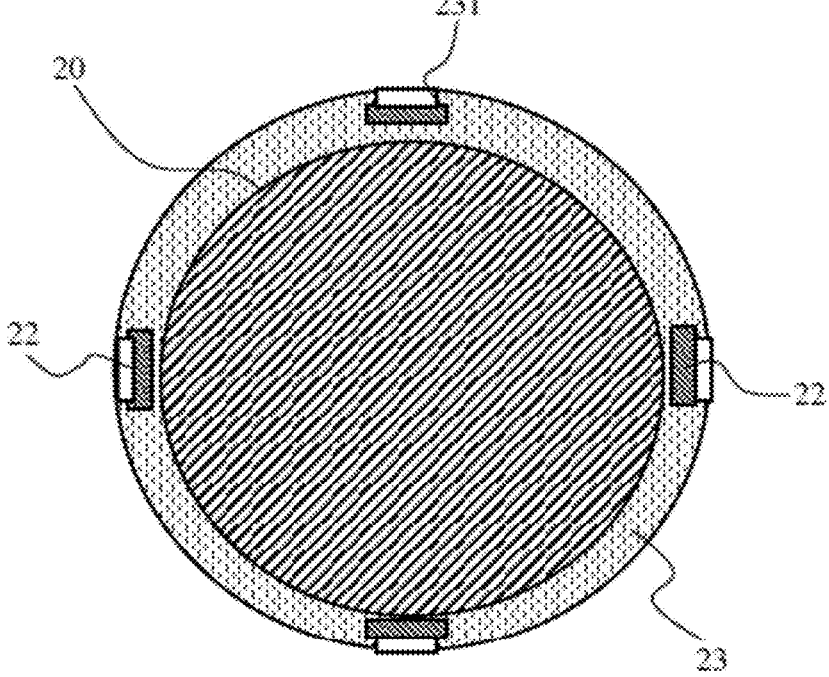
FIG. 42 is a front view that is viewed from the arrow direction in FIG. 41.
Figure 43:
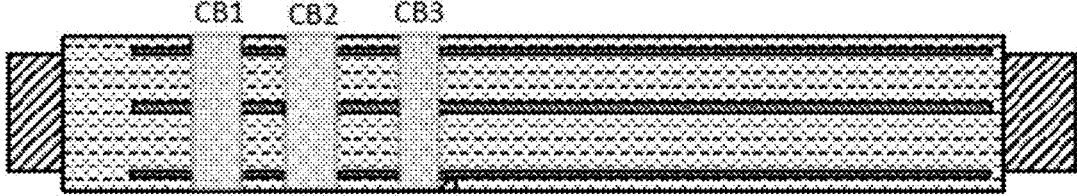
FIG. 43 is a diagram illustrating an example of connecting the pad of the sensor with the electrical connection section using the conductive bands.

Additionally, at the distal end where the conductors have to be electrically interfaced with sensors it necessitates the need for forming or layering conductive bands over openings in an insulation to connect to the embedded conductors. FIG. 41 to FIG. 43 below illustrate the challenges. Exposed sections are radially separated making it impossible to connect to sensor pads that are typically in one plane. Therefore, additional process are required to form the conductive bands so that the sensor can be connected to the traces. FIG. 42 is a front view that is viewed from the arrow direction in FIG. 41.

As is evident from FIG. 41 and FIG. 42, it is not possible to connect sensor pads 51, S2, and S3 to embedded conductors C1, C2, and C3 through exposed sections D1, D2, and D3 because the openings D1, D2, and D3 are radially separated. Formation of conductive bands CB1, CB2, and CB3 on the exposed sections facilitates the connection of the sensor (FIG. 43).

Figure 40D:
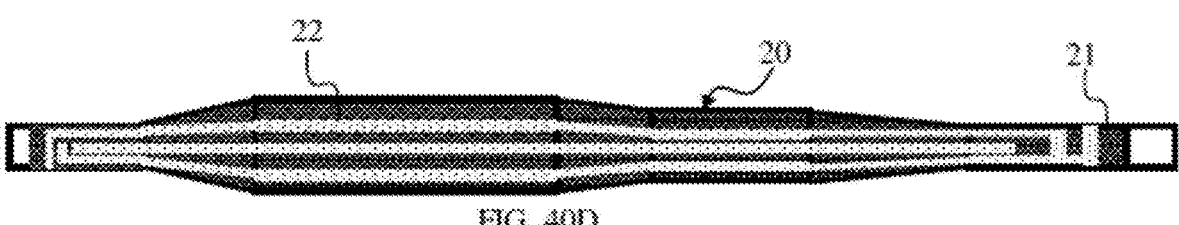
FIG. 40D is a plan view of the guidewire core in which the multiple conductive traces are formed by selectively etching the conductive layer.
Figure 44:
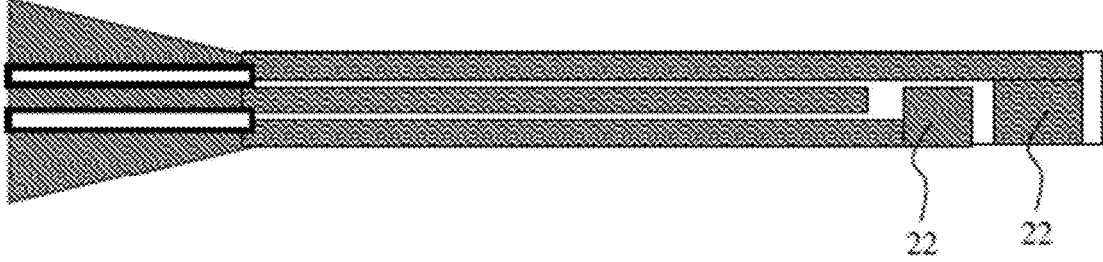
FIG. 44 is a diagram illustrating an example in which a flag section having an area larger than of the other portions can be formed on at least one of the distal end side and the proximal end side of the conductive traces.
Figure 45:
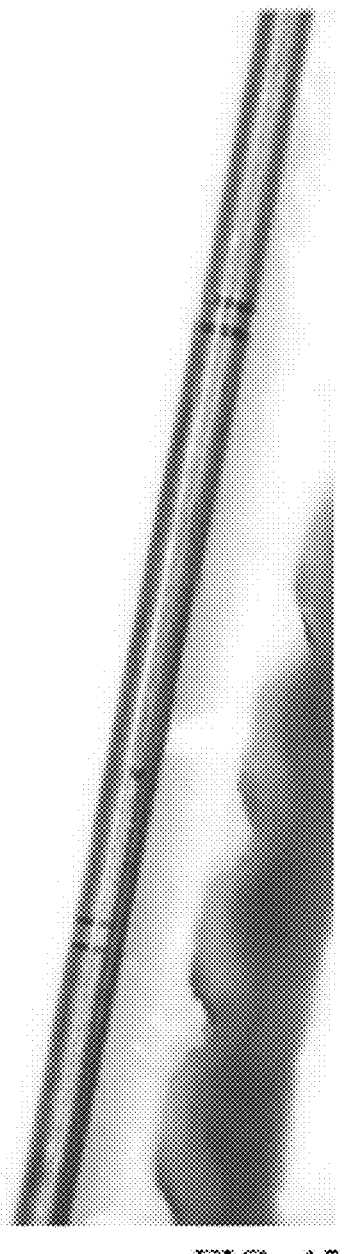
FIG. 45 is an external view of the guidewire core having the conductive traces formed on the surface.
Figure 46:
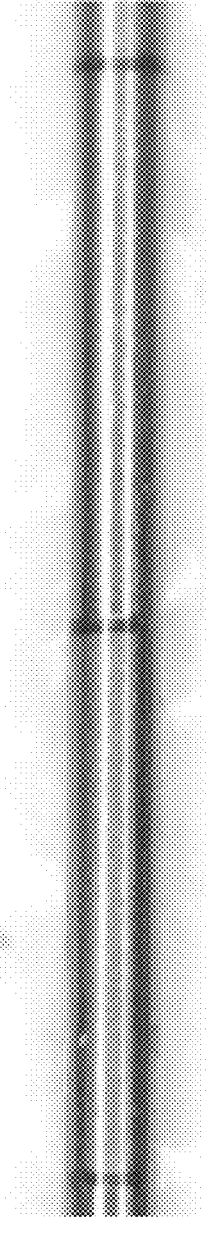
FIG. 46 is an external view of the guidewire core having the conductive traces formed on the surface, which is viewed from another direction.

An approach to mitigate the above challenges, is to apply a conductive layer over the insulating layer such that the conductive layer follows the contours of the substrate as illustrated in FIG. 40B. As described above and illustrated in FIG. 40D individual conductive traces can be formed by laser ablation for example. In this approach a pattern of ablation can be controlled to form "flags" at distal and proximal ends as show in FIG. 44 to FIG. 46.

Additionally, in this approach the trace widths can be varied along the length of the device. Therefore, at the distal end where the core wire length is significantly reduced, the trace width can be accordingly significantly smaller. This method thus allows for a large amount of flexibility in processing over other methods that embed the conductors in an insulated material. Additionally, the conductive material itself can be varied along the length at specific locations to impart desired properties. E.g. the conductive traces can be copper all along the length and then a gold flash can be added via plating to both the ends to enhance electrical connection quality.

Figure 47:
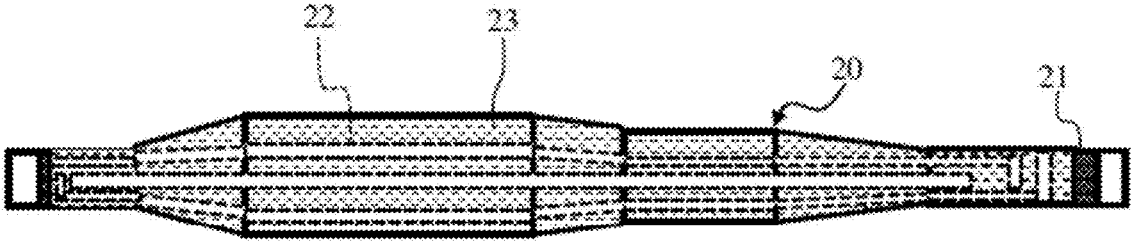
FIG. 47 is a plan view of the guidewire core in which a second insulating layer is formed so as to cover the first insulating layer and the conductive traces.

A second insulating layer is then applied over the, now electrically isolated, conductive elements, as illustrated in FIG. 47. The insulating polymer can be polyimide, PET, Nylon, Pebax etc. The method allows for have a different insulating layer than the 1st base insulation layer to impart different desired properties. Example, the insulating layer can be impregnated with nanoized silica to improve abrasive resistance of the coating.

Figure 48:
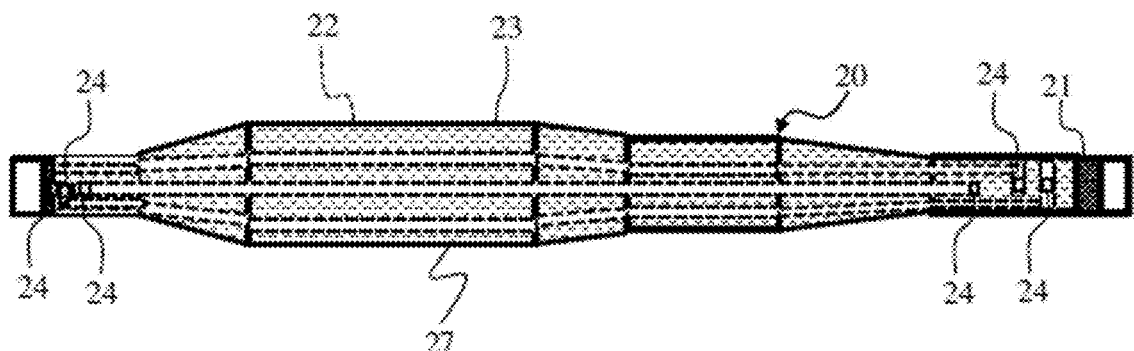
FIG. 48 is a plan view of the guidewire core having the electrical connection sections aligned in a straight line.

Openings in the second insulating layer 23 and the third insulating layer 27 are then created, for example through etching and/or laser ablation, to form vias to access corresponding conductive traces lying immediately below the insulating layers, as illustrated in FIG. 48. These vias form connecting pads to connect or couple the so formed conductive elements to the exterior of the guidewire, for example to one or more sensors on the distal end of the guidewire and connection terminals on the proximal end as suitable.

As seen, all the vias or exposed surfaces on the outer insulation to access the formed conductive elements are all in one longitudinal axis unlike FIG. 41, and, therefore, can easily be connected directly to the sensor pads or through a flex circuit element.

What is claimed is:
1. A guidewire comprising:
a guidewire core,
a first insulating layer disposed on a surface of the guidewire core,
multiple first conductive traces arranged spaced apart from each other in a circumferential direction of the guidewire core and disposed on a surface of the first insulating layer and along a length direction of the guidewire core,
multiple connection sections disposed on at least one of distal and proximal end sides in a length direction of the multiple first conductive traces and electrically connected with an electronic component, and
a second insulating layer that covers the multiple first conductive traces and the first insulating layer, wherein:
ends of the multiple first conductive traces having the multiple connection sections are arranged in parallel to the length direction of the guidewire core,
the multiple connection sections are arranged in a straight line parallel to a longitudinal axis of the guidewire core, the multiple connection sections each comprise an inner opening that is opened on the second insulating layer so as to reach a corresponding first conductive trace, a respective conductive band made of a conductive material is arranged so as to cover at least a portion of each respective inner opening of the multiple connection sections, a respective conductive connection member is disposed on each respective inner opening, each respective connection section of the multiple connection sections is electrically connected with each respective conductive band via the respective conductive connection member, each respective conductive band is made of a different conductive material than each respective conductive connection member, each respective conductive band has an outer opening penetrating the conductive band in a thickness direction and each respective outer opening is arranged so as to overlap with each respective inner opening, the respective conductive connection member for electrically connecting each respective conductive band with each respective connection section is disposed inside each respective outer opening, and each respective outer opening and each respective inner opening are arranged so as to overlap with each other while being offset from each other in the length direction of the guidewire core.

2. The guidewire according to claim 1, wherein an area of each respective inner opening is larger than an area of each respective outer opening.

3. The guidewire according to claim 2, wherein each respective outer opening is formed into a rectangular shape.

4. A guidewire comprising:

a guidewire core, a first insulating layer disposed on a surface of the guidewire core, multiple first conductive traces arranged spaced apart from each other in a circumferential direction of the guidewire core and disposed on a surface of the first insulating layer and along a length direction of the guidewire core, multiple connection sections disposed on at least one of distal and proximal end sides in a length direction of the multiple first conductive traces and electrically connected with an electronic component, and a second insulating layer that covers the multiple first conductive traces and the first insulating layer, wherein:

ends of the multiple first conductive traces having the multiple connection sections are arranged in parallel to the length direction of the guidewire core, the multiple connection sections are arranged in a straight line parallel to a longitudinal axis of the guidewire core, the multiple connection sections each comprise an inner opening that is opened on the second insulating layer so as to reach a corresponding first conductive trace, a respective conductive band made of a conductive material is arranged so as to cover at least a portion of each respective inner opening of the multiple connection sections, a respective conductive connection member is disposed on each respective inner opening, each respective connection section of the multiple connection sections is electrically connected with each respective conductive band via the respective conductive connection member, each respective conductive band is made of a different conductive material than each respective conductive connection member, each respective conductive band has an outer opening penetrating the conductive band in a thickness direction and each respective outer opening is arranged so as to overlap with each respective inner opening, the respective conductive connection member for electrically connecting each respective conductive band with each respective connection section is disposed inside each respective outer opening, and each respective outer opening is formed into an inverse tapered shape that gradually widens from a position opened on one of both ends in a width direction of each respective conductive band toward a side located at a position deviating in the width direction of the respective conductive band.

5. The guidewire according to claim 3, wherein each respective outer opening is formed on both end sides in a width direction of the respective conductive band.

6. A guidewire comprising:

a guidewire core, a first insulating layer disposed on a surface of the guidewire core, multiple first conductive traces arranged spaced apart from each other in a circumferential direction of the guidewire core and disposed on a surface of the first insulating layer and along a length direction of the guidewire core, multiple connection sections disposed on at least one of distal and proximal end sides in a length direction of the multiple first conductive traces and electrically connected with an electronic component, and a second insulating layer that covers the multiple first conductive traces and the first insulating layer, wherein:

ends of the multiple first conductive traces having the multiple connection sections are arranged in parallel to the length direction of the guidewire core, the multiple connection sections are arranged in a straight line parallel to a longitudinal axis of the guidewire core, the multiple connection sections each comprise an inner opening that is opened on the second insulating layer so as to reach a corresponding first conductive trace, a respective conductive band made of a conductive material is arranged so as to cover at least a portion of each respective inner opening of the multiple connection sections, a respective conductive connection member is disposed on each respective inner opening, each respective connection section of the multiple connection sections is electrically connected with each respective conductive band via the respective conductive connection member, each respective conductive band is made of a different conductive material than each respective conductive connection member, each respective conductive band has an outer opening penetrating the conductive band in a thickness direction and each respective outer opening is arranged so as to overlap with each respective inner opening, the respective conductive connection member for electrically connecting each respective conductive band with each respective connection section is disposed inside each respective outer opening, and each respective conductive band comprises the respective conductive connection member that is made of an anisotropic conductive material and arranged so as to fill insides of the respective outer opening and the respective inner opening and cover the second insulating layer, and a C-shaped member that is made of a conductive material and disposed outside the respective conductive connection member.

7. A guidewire comprising:
a guidewire core,
a first insulating layer disposed on a surface of the guidewire core,
multiple first conductive traces arranged spaced apart from each other in a circumferential direction of the guidewire core and disposed on a surface of the first insulating layer and along a length direction of the guidewire core,
multiple connection sections disposed on a distal end side in a length direction of the multiple first conductive traces and electrically connected with an electronic component, and
a second insulating layer that covers the multiple first conductive traces and the first insulating layer, wherein:
ends of the multiple first conductive traces having the multiple connection sections are arranged in parallel to the length direction of the guidewire core,
the multiple connection sections are arranged in a straight line parallel to a longitudinal axis of the guidewire core,
the multiple connection sections each comprise an inner opening that is opened on the second insulating layer so as to reach a corresponding first conductive trace,
a respective conductive band made of a conductive material is arranged so as to cover at least a portion of each respective inner opening of the multiple connection sections,
each respective connection section of the multiple connection sections is electrically connected with each respective conductive band via a respective conductive connection member disposed in each respective inner opening,
each respective conductive band is electrically connected with a printed wiring board equipped with the electronic component via a conductive connection member for a substrate, and
the printed wiring board has a flexible substrate member located on the conductive band side and a rigid substrate member located on a distal end side of the flexible substrate member, and
the electronic component is disposed on the rigid substrate member.

8. The guidewire according to claim 7, wherein
the rigid substrate member has an accommodation section for accommodating and mounting the electronic component, and the rigid substrate member is disposed on the distal end side of the guidewire core.

9. A guidewire comprising:
a guidewire core,
a first insulating layer disposed on a surface of the guidewire core,
multiple first conductive traces arranged spaced apart from each other in a circumferential direction of the guidewire core and disposed on a surface of the first insulating layer and along a length direction of the guidewire core,
a second insulating layer that covers the multiple first conductive traces and the first insulating layer,
multiple connection sections disposed on at least one of distal and proximal end sides in a length direction of the multiple first conductive traces and electrically connected with an electronic component, and comprising an inner opening that is opened on the second insulating layer so as to reach a corresponding first conductive trace,
conductive bands formed in a circumferential direction so as to cover the multiple connection sections and the second insulating layer,
an outer opening penetrating the conductive bands in a thickness direction and arranged so as to overlap with the inner opening, and
a conductive connection member disposed inside the outer opening and the inner opening to electrically connect the conductive bands with the connection sections,
wherein the outer opening and the inner opening are arranged so as to overlap with each other while being offset from each other in the length direction of the guidewire core.

10. The guidewire according to claim 9, wherein
an area of the inner opening is larger than an area of the outer opening.

11. A guidewire comprising:
a guidewire core,
a first insulating layer disposed on a surface of the guidewire core,
multiple first conductive traces arranged spaced apart from each other in a circumferential direction of the guidewire core and disposed on a surface of the first insulating layer and along a length direction of the guidewire core,
a second insulating layer that covers the multiple first conductive traces and the first insulating layer,
multiple connection sections disposed on at least one of distal and proximal end sides in a length direction of the multiple first conductive traces and electrically connected with an electronic component, and comprising an inner opening that is opened on the second insulating layer so as to reach a corresponding first conductive trace,
conductive bands formed in a circumferential direction so as to cover the multiple connection sections and the second insulating layer,
an outer opening penetrating the conductive bands in a thickness direction and arranged so as to overlap with the inner opening, and
a conductive connection member disposed inside the outer opening and the inner opening to electrically connect the conductive bands with the connection sections,
wherein the outer opening is formed into a rectangular shape.

12. A guidewire comprising:
a guidewire core,
a first insulating layer disposed on a surface of the guidewire core,
multiple first conductive traces arranged spaced apart from each other in a circumferential direction of the guidewire core and disposed on a surface of the first insulating layer and along a length direction of the guidewire core,
a second insulating layer that covers the multiple first conductive traces and the first insulating layer,
multiple connection sections disposed on at least one of distal and proximal end sides in a length direction of the multiple first conductive traces and electrically connected with an electronic component, and comprising an inner opening that is opened on the second insulating layer so as to reach a corresponding first conductive trace, conductive bands formed in a circumferential direction so as to cover the multiple connection sections and the second insulating layer, an outer opening penetrating the conductive bands in a thickness direction and arranged so as to overlap with the inner opening, and a conductive connection member disposed inside the outer opening and the inner opening to electrically connect the conductive bands with the connection sections, wherein the outer opening is formed into an inverse tapered shape where a width dimension on the end side of the conductive bands is small, and the width dimension gradually increases in a width direction of the conductive bands.

13. The guidewire according to claim 10, wherein each outer opening is formed on distal and proximal end sides in a width direction of the conductive bands.

14. The guidewire according to claim 10, wherein the conductive bands and the conductive connection member are made of conductive metal materials.

15. The guidewire according to claim 10, wherein the conductive connection member is made of an anisotropic conductive material that forms a conductive path in the thickness direction of the conductive bands by a pressure applied in the thickness direction of the conductive bands.

16. The guidewire according to claim 10, further comprising multiple second conductive traces disposed on a surface of the second insulating layer, a third insulating layer arranged so as to cover the multiple second conductive traces and the second insulating layer, multiple second connection sections arranged in a straight line parallel to a longitudinal axis of the guidewire core on at least one of distal and proximal end sides in a length direction of the multiple second conductive traces and electrically connected with an electronic component, and comprising a second inner opening opened on the third insulating layer so as to reach a corresponding second conductive trace, and a second conductive band formed in the circumferential direction of the guidewire core so as to cover at least one of the multiple second connection sections, wherein the at least one second connection section covered by the second conductive band is electrically connected with the second conductive band via the conductive connection member disposed on the second inner opening.

17. The guidewire according to claim 10, wherein the multiple first conductive traces include at least one group consisting of the multiple first conductive traces whose lengths are equal.

18. The guidewire according to claim 17, wherein the multiple first conductive traces constituting the group are formed as a point-symmetrical pair.

19. The guidewire according to claim 17, wherein at least one of the multiple first conductive traces constituting the group has a meandering section so as to have the same length as of the other first conductive trace in the group.

* * * * *